US012799504B2

(12) United States Patent
Marson et al.

(10) Patent No.: US 12,799,504 B2
(45) Date of Patent: Nov. 17, 2026

(54) COMPOSITIONS AND METHODS FOR MODIFYING A TARGET NUCLEIC ACID

(71) Applicant: The Regents of the University of California, Oakland, CA (US)

(72) Inventors: Alexander Marson, Oakland, CA (US); Brian Shy, Oakland, CA (US); Jonathan Esensten, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 1038 days.

(21) Appl. No.: 17/911,391

(22) PCT Filed: Mar. 12, 2021

(86) PCT No.: PCT/US2021/022058

§ 371 (c)(1),
(2) Date: Sep. 13, 2022

(87) PCT Pub. No.: WO2021/183850

PCT Pub. Date: Sep. 16, 2021

(65) Prior Publication Data

US 2023/0159957 A1 May 25, 2023

Related U.S. Application Data

(60) Provisional application No. 62/989,501, filed on Mar. 13, 2020.

(51) Int. Cl.

| | |
|---|---|
| ***C12N 15/11*** | (2006.01) |
| ***C12N 9/22*** | (2006.01) |
| ***C12N 15/90*** | (2006.01) |

(52) U.S. Cl.

CPC ............ *C12N 15/907* (2013.01); *C12N 9/22* (2013.01); *C12N 15/11* (2013.01); *C12N 2310/20* (2017.05); *C12N 2800/80* (2013.01)

(58) Field of Classification Search
None
See application file for complete search history.

(56) References Cited

U.S. PATENT DOCUMENTS

2019/0345479 A1 11/2019 Mello et al.

FOREIGN PATENT DOCUMENTS

| | | | |
|---|---|---|---|
| WO | 2018081728 | A1 | 5/2018 |
| WO | 2019226998 | A1 | 11/2019 |
| WO | 2019232251 | A1 | 12/2019 |
| WO | 2020123871 | A1 | 6/2020 |

OTHER PUBLICATIONS

Nguyen et al., Nature Biotechnology, vol. 38, Jan. 2020, pp. 44-49 (Year: 2020).*
Nguyen et al., Supplementary Information, Nature Biotechnology, vol. 38, Jan. 2020, 36 pages (Year: 2020).*
Nguyen , et al., "Polymer-Stabilized Cas9 Nanoparticles and Modified Repair Templates Increase Genome Editing Efficiency", Nature Biotechnology, vol. 38, Issue 1, Jan. 2020, 16 pages.
PCT/US2021/022058 , "International Search Report and Written Opinion", Jul. 12, 2021, 11 pages.

* cited by examiner

*Primary Examiner* — Evelyn Y Pyla
(74) *Attorney, Agent, or Firm* — Kilpatrick Townsend & Stockton LLP

(57) ABSTRACT

The disclosure provides compositions and methods for modifying a target nucleic acid that use a donor construct including at least one donor template comprising a single-stranded homology directed repair template (ssHDRT) and one or more DNA-binding protein target sequences, in which at least one DNA-binding protein target sequence forms a double-stranded duplex with a complementary polynucleotide sequence.

27 Claims, 28 Drawing Sheets

Specification includes a Sequence Listing.

CD5-HA
2708 bp

IL2RA-
tNGFR
1300 bp

IL2RA-
CD25-
GFP
2267 bp

COMPOSITIONS AND METHODS FOR MODIFYING A TARGET NUCLEIC ACID

CROSS-REFERENCE TO RELATED APPLICATIONS

The present application is a 371 U.S. National Phase of PCT International Application No. PCT/US2021/022058 filed Mar. 12, 2021, which claims benefit of priority to U.S. Provisional Patent Application No. 62/989,501, filed Mar. 13, 2020, which are incorporated by reference for all purposes.

STATEMENT AS TO RIGHTS TO INVENTIONS MADE UNDER FEDERALLY SPONSORED RESEARCH AND DEVELOPMENT

This invention was made with government support under grant no. P50 GM082250 awarded by The National Institutes of Health. The government has certain rights in the invention.

BACKGROUND OF THE DISCLOSURE

The application of clustered regularly interspaced short palindromic repeats (CRISPR) and CRISPR-associated (Cas) proteins has revolutionized molecular biology by making genome editing possible. CRISPR-mediated gene editing is a powerful and practical tool with potential for creating new scientific tools, correcting clinically relevant mutations, and engineering new cell-based immunotherapies.

BRIEF SUMMARY OF THE DISCLOSURE

In one aspect, the disclosure features a donor construct comprising at least one donor template comprising a single-stranded homology directed repair template (HDRT) and one or more DNA-binding protein target sequences, wherein at least one DNA-binding protein target sequence forms a double-stranded duplex with a complementary polynucleotide sequence.

In some embodiments, the donor construct comprises (a) a first polynucleotide comprising a single donor template, and (b) at least one second polynucleotide comprising a complementary polynucleotide sequence, wherein the donor template is a single-stranded linear template. In some embodiments, the donor template comprises only one DNA-binding protein target sequence, and wherein the DNA-binding protein target sequence hybridizes to the complementary polynucleotide sequence. In certain embodiments, the DNA-binding protein target sequence is located at or proximal to the 5' terminus of the donor template. In other embodiments, the DNA-binding protein target sequence is located at or proximal to the 3' terminus of the donor template.

In some embodiments of this aspect, the donor template comprises:

a first DNA-binding protein target sequence located at or proximal to the 5' terminus of the donor template; a second DNA-binding protein target sequence located at or proximal to the 3' terminus of the donor template; a first complementary polynucleotide sequence; and a second complementary polynucleotide sequence, wherein the first DNA-binding protein target sequence hybridizes to the first complementary polynucleotide sequence and the second DNA-binding protein target sequence hybridizes to the second complementary polynucleotide sequence.

In some embodiments of this aspect, the donor construct comprises (a) a first donor template comprising a first DNA-binding protein target sequence located at or proximal to the 3' terminus of the first donor template, and (b) a second donor template comprising a second DNA-binding protein target sequence located at or proximal to the 3' terminus of the second donor template, wherein the first DNA-binding protein target sequence hybridizes to the second DNA-binding protein target sequence. In some embodiments, the second donor template further comprises a third DNA-binding protein target sequence located at or proximal to the 5' terminus of the second donor template, and the donor construct further comprises (c) a third donor template comprising a fourth DNA-binding protein target sequence located at or proximal to the 5' terminus of the third template, wherein the third DNA-binding protein target sequence hybridizes to the fourth DNA-binding protein target sequence.

In some embodiments of this aspect, the DNA-binding protein target sequence and the complementary polynucleotide sequence form a hairpin. In certain embodiments, the donor construct comprises a single donor template and the donor template comprises a single hairpin formed by a first DNA-binding protein target sequence and a second DNA-binding protein target sequence as the complementary polynucleotide sequence. In some embodiments, the donor construct comprises a single donor template, and the donor template comprises two hairpins and: (a) a first DNA-binding protein target sequence; (b) a second DNA-binding protein target sequence as a first complementary polynucleotide sequence; (c) a third DNA-binding protein target sequence; and (d) a fourth DNA-binding protein target sequence as a second complementary polynucleotide sequence, wherein the first DNA-binding protein target sequence hybridizes to the second DNA-binding protein target sequence to form a first hairpin at or proximal to the 5' terminus of the donor template, and the third DNA-binding protein target sequence hybridizes to the fourth DNA-binding protein target sequence to form a second hairpin at or proximal to the 3' terminus of the donor template.

In certain embodiments, the donor template further comprises a third DNA-binding protein target sequence, and the donor construct further comprises a polynucleotide comprising a second complementary polynucleotide sequence, wherein the third DNA-binding protein target sequence hybridize to the second complementary polynucleotide sequence.

In some embodiments, the donor construct comprises a first donor template and a second donor template, each comprising a first DNA-binding protein target sequence and a second DNA-binding protein target sequence as the complementary polynucleotide sequence, and wherein a portion of the first donor template and a portion of the second donor template hybridize to each other.

In some embodiments, the donor construct comprises a single donor template and the donor template comprises: (a) a first fragment comprising a first hairpin formed by a first DNA-binding protein target sequence and a second DNA-binding protein target sequence as the complementary polynucleotide sequence; (b) a second fragment comprising a second hairpin formed by a third DNA-binding protein target sequence and a fourth DNA-binding protein target sequence as the complementary polynucleotide sequence; and (c) a third fragment comprising the HDRT, wherein a portion of the first fragment hybridize to a 5' portion of the third fragment, and a portion of the second fragment hybridize to a 3' portion of the third fragment.

In some embodiments of this aspect, the DNA-binding protein target sequence is bound by a donor guide RNA (gRNA), which is bound by an RNA-guided nuclease. In particular embodiments, the RNA-guide nuclease is a Cas protein. Examples of Cas proteins include, but are not limited to, Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, and a variant thereof.

In some embodiments, the DNA-binding protein target sequence comprises a sequence of any one of SEQ ID NOS:30-35. In some embodiments, the donor template comprises one or more protospacer adjacent motifs (PAMs). In particular embodiments, the PAM is located at the 5' terminus of the DNA-binding protein target sequence. In particular embodiments, the PAM is located at the 3' terminus of the DNA-binding protein target sequence.

In another aspect, the disclosure provides a composition for modifying a target nucleic acid, comprising: (a) a targetable nuclease; (b) a DNA-binding protein; (c) a donor construct described herein. In some embodiments, the targetable nuclease and DNA-binding protein are the same and comprise an RNA-guided nuclease (e.g., a Cas protein). Examples of Cas proteins include, but are not limited to, Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, and a variant thereof.

In some embodiments of this aspect, the composition comprises a target guide RNA (gRNA) and a donor gRNA. In certain embodiments, the target gRNA is complementary to the target nucleic acid. In certain embodiments, the DNA-binding protein target sequence is complementary to an equal length portion of the sequence of the donor gRNA. Further, the composition can include an anionic polymer, e.g., a polyglutamic acid (PGA), a polyaspartic acid, or a polycarboxyglutamic acid.

In another aspect, the disclosure provides a method for modifying a target nucleic acid in a cell, comprising introducing into the cell a composition described above, wherein the HDRT is integrated into the target nucleic acid. In some embodiments of the method, the introducing comprises electroporation. In particular embodiments, the cell is a primary cell, such as a primary T cell. In some embodiments, an exogenous nucleotide sequence is introduced into the cell and the modifying comprises inserting the exogenous nucleotide sequence into the target nucleic acid. In other embodiments, the modifying comprises excising the target nucleic acid. In some embodiments, the modifying comprises targeting an exogenous protein to the target nucleic acid. For example, the exogenous protein can be a transcription activator or repressor. In some embodiments, the method is performed in vivo, in vitro, or ex vivo. In some embodiments, the method enables the use of a lower concentration or amount of a donor construct described herein relative to the concentration or amount of a corresponding HDRT to achieve the same or higher gene editing (e.g., knock-in) efficiency. In some embodiments, an amount of HDRT used is less than 1 pmol (e.g., less than 0.8 pmol, less than 0.6 pmol, less than 0.4 pmol, less than 0.2 pmol, less than 0.1 pmol, less than 0.08 pmol, less than 0.06 pmol, less than 0.04 pmol, less than 0.02 pmol, or less than 0.01 pmol).

Definitions

As used in this specification and the appended claims, the singular forms "a," "an," and "the" include plural reference unless the context clearly dictates otherwise.

As used herein, the "CRISPR-Cas" system refers to a class of bacterial systems for defense against foreign nucleic acid. CRISPR-Cas systems are found in a wide range of eubacterial and archaeal organisms. CRISPR-Cas systems include type I, II, and III sub-types. Wild-type type II CRISPR-Cas systems utilize an RNA-mediated nuclease, for example, Cas9 protein, in complex with guide and activating RNA (e.g., single-guide RNA or sgRNA) to recognize and cleave foreign nucleic acids, i.e., foreign nucleic acids including natural or modified nucleotides.

As used herein, the term "targetable nuclease" refers to a protein that can recognize a sequence of a target nucleic acid (e.g., a target gene within a genome) and bind to the target nucleic acid. In some embodiments, the targetable nuclease can modify the target nucleic acid. In some embodiments, a targetable nuclease can be an RNA-guided nuclease, e.g., a Cas protein. In other embodiments, a targetable nuclease can be a fusion protein that includes a protein that can bind to the target nucleic acid (e.g., a transcription activator-like (TAL) effector DNA-binding protein or a zinc finger DNA-binding protein) and a protein that can modify the target nucleic acid (e.g., a nuclease, a transcription activator or repressor). In some embodiments, the targetable nuclease has nuclease activity. In other embodiments, the targetable nuclease does not have nuclease activity. In some embodiments, the targetable nuclease can modify the target nucleic acid by cleaving the target nucleic acid. The cleaved target nucleic acid can then undergo homologous recombination with a nearby a homology directed repair (HDR) template. In other embodiments, the targetable nuclease (e.g., a targetable nuclease without any nuclease activity) can regulate the expression of the target nucleic acid. For example, a targetable nuclease can be a fusion protein containing a TAL effector DNA-binding protein and a transcription activator.

As used herein, the term "DNA-binding protein" refers to a protein that can directly or indirectly bind to a DNA-binding protein target sequence within a donor template (which includes an HDR template). Without being bound by any theory, the DNA-binding protein serves to transport or shuttle the donor template to a cellular location close to the target nucleic acid. Thus, the DNA-binding protein can improve the delivery of the HDR template into target cells, especially to the cell nucleus, and increase knock-in efficiencies. In some embodiments, the DNA-binding protein can be a transcription activator-like (TAL) effector DNA-binding protein or a zinc finger DNA-binding protein. Each of the transcription activator-like (TAL) effector DNA-binding protein and zinc finger DNA-binding protein can directly bind to a DNA-binding protein target sequence within a donor template. In some embodiments, the DNA-binding protein can be an RNA-guided nuclease, e.g., a Cas protein, which can indirectly bind to a DNA-binding protein target sequence within a donor template via a donor gRNA.

As used herein, the term "donor template" refers one or more strands polynucleotides that together form a homology directed repair template (HDRT) and one or more DNA-binding protein target sequences. An HDRT can include a 5' homology arm, a nucleotide insert (e.g., an exogenous sequence and/or a sequence that encodes a heterologous protein or fragment thereof), and a 3' homology arm. In some embodiments, the donor template can also include one or more edge sequences at one or both termini of the donor template. In some embodiments, the donor template can be formed from a single polynucleotide molecule (e.g., "half loop" and "hairpin" as shown in FIG. 1). In other embodiments, the donor template can be formed from two or more polynucleotide molecules (e.g., "cap" as shown in FIG. 1). In certain embodiments, the donor template is a linear template (e.g., the donor template in "primer" as shown in FIG. 1), which means that the donor template does not have any hairpin regions. In other embodiments, the donor template can contain a hairpin region (e.g., the donor template in "half loop" as shown in FIG. 1).

As used herein, the term "donor construct" refers a molecule containing one or more donor templates. In some embodiments, when the donor construct contains two or more donor templates, the HDRT in each donor template can have the same sequence or different sequences.

As used herein, the term "single-stranded" refers to a polynucleotide in which more than 80% (e.g., more than 85/6, 90%, or 95%) of its nucleotides do not hybridize to other nucleotides (e.g., other complementary nucleotides). In some instances, a few nucleotides in a singled-stranded polynucleotide can hybridize to other nucleotides (e.g., other complementary nucleotides), but the majority (e.g., more than 80%) of the nucleotides in the single-stranded polynucleotide do not hybridize to other nucleotides (e.g., other complementary nucleotides).

As used herein, the term "double-stranded duplex" refers to two regions of polynucleotides that are complementary to each other and hybridize to each other via hydrogen bonding to form a double-stranded region. In some embodiments, the two regions of complementary polynucleotides can be within the same strand polynucleotide molecule. In other embodiments, the two regions of complementary polynucleotides can be from separate strands of polynucleotide molecules.

As used herein, the term "hairpin" refers to a nucleotide structure that is formed when two polynucleotide regions within the same polynucleotide strand hybridize to form a double helix or a double-stranded duplex region that ends in an unpaired loop. In some embodiments, the unpaired loop in the hairpin has between 4 and 200 (e.g., between 4 and 180, between 4 and 160, between 4 and 140, between 4 and 120, between 4 and 100, between 4 and 80, between 4 and 60, between 4 and 40, between 4 and 20, between 4 and 10, between 4 and 8, between 8 and 200, between 10 and 200, between 20 and 200, between 40 and 200, between 60 and 200, between 80 and 200, between 100 and 200, between 120 and 200, between 140 and 200, between 160 and 200, or between 180 and 200) nucleotides. In some embodiments, each of the two polynucleotide regions that hybridize in a hairpin is between 10 and 50 (e.g., between 10 and 45, between 10 and 40, between 10 and 35, between 10 and 30, between 10 and 25, between 10 and 20, between 10 and 15, between 15 and 50, between 20 and 50, between 25 and 50, between 30 and 50, between 35 and 50, between 40 and 50, or between 45 and 50) nucleotides.

As used herein, the term "DNA-binding protein target sequence" refers to a nucleotide sequence that is recognized and bound by a DNA-binding protein. In some embodiments, the DNA-binding protein, e.g., a transcription activator-like (TAL) effector DNA-binding protein or zinc finger DNA-binding protein, can directly recognize and bind a DNA-binding protein target sequence. In other embodiments, a DNA-binding protein, e.g., an RNA-guided nuclease, can indirectly recognize and bind a DNA-binding protein target sequence via a donor gRNA. The DNA-binding protein, e.g., the RNA-guided nuclease, binds to the donor gRNA, which hybridizes to the DNA-binding protein target sequence. In some embodiments, the DNA-binding protein target sequence is a portion of the target nucleic acid. In some embodiments, a DNA-binding protein target sequence has between 15 and 40 (e.g., between 15 and 35, between 15 and 30, between 15 and 25, between 15 and 20, between 20 and 35, between 25 and 35, or between 30 and 35) nucleotides.

As used herein, the "RNA-guided nuclease" refers to a nuclease that binds to a guide RNA (gRNA) and utilizes the gRNA to search for regions within a DNA polynucleotide that it can target. In general, an RNA-guided nuclease can target nearly any sequence within the DNA polynucleotide that is complementary to the gRNA. In some embodiments, the RNA-guided nuclease has nuclease activity and can cleave the linkage (e.g., phosphodiester bonds) between nucleotides in the DNA polynucleotide. In other embodiments, the RNA-guided nuclease does not have nuclease activity and can be used to target or localize other proteins (e.g., transcritional activator or repressors) that are fused to the RNA-guided nuclease to the region of interest within the DNA polynucleotide.

As used herein, the term "guide RNA" or "gRNA" refers to a DNA-targeting RNA that can guide an RNA-guided nuclease (e.g., a Cas protein) to a target nucleic acid by hybridizing to the target nucleic acid. In some embodiments, a guide RNA can be a single-guide RNA (sgRNA), which contains a guide sequence (i.e., crRNA equivalent portion of the single-guide RNA) that targets the RNA-guided nuclease to the target nucleic acid and a scaffold sequence (i.e., tracrRNA equivalent portion of the single-guide RNA) that interacts with the RNA-guided nuclease. In other embodiments, a guide RNA can contain two components, a guide sequence (i.e., crRNA equivalent portion of the single-guide RNA) that targets the RNA-guided nuclease to the target nucleic acid and a scaffold sequence (i.e., tracrRNA equivalent portion of the single-guide RNA) that interacts with the RNA-guided nuclease. A portion of the guide sequence can hybridize to a portion of the scaffold sequence to form the two-component guide RNA.

As used herein, the term "target guide RNA" or "target gRNA" refers to a gRNA that can hybridize to the target nucleic acid, e.g., at a location in the target nucleic acid where integration of the HDR template happens.

As used herein, the term "donor guide RNA" or "donor gRNA" refers to a gRNA that can hybridize a DNA-binding protein target sequence within a donor template. In some embodiments, a DNA-binding protein target sequence can be complementary (e.g., partially complementary or completely complementary) to an equal length portion of the sequence of a donor gRNA.

As used herein, the term "single-guide RNA" or "sgRNA" refers to a DNA-targeting RNA containing a guide sequence (i.e., crRNA equivalent portion of the single-guide RNA) that targets the Cas protein to the target DNA and a scaffold sequence (i.e., tracrRNA equivalent portion of the single-guide RNA) that interacts with the Cas protein.

As used herein, the term "proximal" refers to within 20 (e.g., 20, 19, 18, 17, 16, 15, 14, 13, 12, 11, 10, 9, 8, 7, 6, 5, 4, 3, 2, or 1) nucleotides from a certain specified location. For example, a sequence that is proximal to the 5' terminus of a polynucleotide means that the sequence is within 20 nucleotides from the 5' terminus of the polynucleotide.

As used herein, the term "hybridize" or "hybridization" refers to the annealing of complementary nucleic acids through hydrogen bonding interactions that occur between complementary nucleobases, nucleosides, or nucleotides. The hydrogen bonding interactions may be Watson-Crick hydrogen bonding or Hoogsteen or reverse Hoogsteen hydrogen bonding. Examples of complementary nucleobase pairs include, but are not limited to, adenine and thymine, cytosine and guanine, and adenine and uracil, which all pair through the formation of hydrogen bonds.

As used herein, the term "complementary" or "complementarity" refers to the capacity for base pairing between nucleobases, nucleosides, or nucleotides, as well as the capacity for base pairing between one polynucleotide to another polynucleotide. In some embodiments, one polynucleotide can have "complete complementarity," or be "completely complementary," to another polynucleotide, which means that when the two polynucleotides are optionally aligned, each nucleotide in one polynucleotide can engage in Watson-Crick base pairing with its corresponding nucleotide in the other polynucleotide. In other embodiments, one polynucleotide can have "partial complementarity," or be "partially complementary," to another polynucleotide, which means that when the two polynucleotides are optionally aligned, at least 60% (e.g., 65%, 70%, 75%, 80%, 85%, 90%, 95%, or 97%) but less than 100% of the nucleotides in one polynucleotide can engage in Watson-Crick base pairing with their corresponding nucleotides in the other polynucleotide. In other words, there is at least one (e.g., one, two, three, four, five, six, seven, eight, nine, or ten) mismatched nucleotide base pair when the two polynucleotides are hybridized. Pairs of nucleotides that engage in Watson-Crick base pairing includes, e.g., adenine and thymine, cytosine and guanine, and adenine and uracil, which all pair through the formation of hydrogen bonds. Examples of mismatched bases include a guanine and uracil, guanine and thymine, and adenine and cytosine pairing.

As used herein, the term "Cas protein" refers to a Clustered Regularly Interspaced Short Palindromic Repeats-associated protein or nuclease. A Cas protein can be a wild-type Cas protein or a Cas protein variant. Cas9 protein is an example of a Cas protein that belongs in the type II CRISPR-Cas system (e.g., Rath et al., *Biochimie* 117:119, 2015). Other examples of Cas proteins are described in detail further herein. A naturally-occurring Cas protein requires both a crRNA and a tracrRNA for site-specific DNA recognition and cleavage. The crRNA associates, through a region of partial complementarity, with the tracrRNA to guide the Cas protein to a region homologous to the crRNA in the target DNA called a "protospacer". A naturally-occurring Cas protein cleaves DNA to generate blunt ends at the double-strand break at sites specified by a guide sequence contained within a crRNA transcript. In some embodiments of the compositions and methods described herein, a Cas protein associates with a target gRNA or a donor gRNA to form a ribonucleoprotein (RNP) complex. In some embodiments of the compositions and methods described herein, the Cas protein has nuclease activity. In other embodiments, the Cas protein does not have nuclease activity.

As used herein, the term "Cas protein variant" refers to a Cas protein that has at least one amino acid substitution (e.g., one, two, three, four, five, six, seven, eight, nine, ten, or more amino acid substitutions) relative to the sequence of a wild-type Cas protein and/or is a truncated version or fragment of a wild-type Cas protein. In some embodiments, a Cas protein variant has at least 75% sequence identity (e.g., at least 75%, 80%, 85%, 90%, 91%, 92%, 93%, 94% 95%, 96%, 97%, 98%, 99%, or 100% sequence identity) to the sequence of a wild-type Cas protein. In some embodiments, a Cas protein variant is a fragment of a wild-type Cas protein and has at least one amino acid substitution relative to the sequence of the wild-type Cas protein. A Cas protein variant can be a Cas9 protein variant. In some embodiments, a Cas protein variant has nuclease activity. In other embodiments, a Cas protein variant does not have nuclease activity.

As used herein, the term "ribonucleoprotein complex" or "RNP complex" refers to a complex comprising a Cas protein or variant (e.g., a Cas9 protein or variant) and a gRNA.

As used herein, the term "modifying" in the context of modifying a target nucleic acid in the genome of a cell refers to inducing a change (e.g., cleavage) in the target nucleic acid. In some embodiments, the change can be a structural change in the sequence of the target nucleic acid. For example, the modifying can take the form of inserting a nucleotide sequence into the target nucleic acid. For example, an exogenous nucleotide sequence can be inserted into the target nucleic acid. The target nucleic acid can also be excised and replaced with an exogenous nucleotide sequence. In another example, the modifying can take the form of cleaving the target nucleic acid without inserting a nucleotide sequence into the target nucleic acid. For example, the target nucleic acid can be cleaved and excised. Such modifying can be performed, for example, by inducing a double stranded break within the target nucleic acid, or a pair of single stranded nicks on opposite strands and flanking the target nucleic acid. Methods for inducing single or double stranded breaks at or within a target nucleic acid include the use of a targetable nuclease (e.g., a Cas protein) as described herein directed to the target nucleic acid. In other embodiments, modifying a target nucleic acid includes targeting another protein to the target nucleic acid and does not include cleaving the target nucleic acid.

As used herein, the term "anionic polymer" refers to a molecule composed of multiple subunits or monomers that has an overall negative charge. Each subunit or monomer in a polymer can, independently, be an amino acid, a small organic molecule (e.g., an organic acid), a sugar molecule (e.g., a monosaccharide or a disaccharide), or a nucleotide. An anionic polymer can contain multiple amino acids, small organic molecules (e.g., organic acids), nucleotides (e.g., natural or non-natural nucleotides, or analogues thereof), or a combination thereof. An anionic polymer can be an anionic homopolymer where all subunits or monomers in the polymer are the same. An anionic polymer can be an anionic heteropolymer where the subunits and monomers in the polymer are different. An anionic polymer does not refer to a nucleic acid, such as a deoxyribonucleic acid (DNA), ribonucleic acid (RNA), that is composed entirely of nucleotides. However, an anionic polymer can include one or more nucleobases (e.g., guanosine, cytidine, adenosine, thymidine, and uridine) together with other subunits or monomers, such as amino acids and/or small organic molecules (e.g., an organic acid). In some embodiments, at least 50% (e.g. 55%, 60%, 65%, 70%, 75%, 80%, 85%, 90%, 95%, or 100%) of the subunits or monomers in the polymer are not nucleotides or do not contain nucleobases. An anionic polymer can be an anionic polypeptide or an anionic polysaccharide. An anionic polymer can contain at least two subunits or monomers (e.g., at least 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 subunits or monomers; between 100 and 400, between 120 and 400, between 140 and 400, between 160 and 400, between 180 and 400, between 200 and 400, between 220 and 400, between 240 and 400, between 260 and 400, between 280 and 400, between 300 and 400, between 320 and 400, between 340 and 400, between 360 and 400, between 380 and 400, between 100 and 380, between 100 and 360, between 100 and 340, between 100 and 320, between 100 and 300, between 100 and 280, between 100 and 260, between 100 and 240, between 100 and 220, between 100 and 200, between 100 and 180, between 100 and 160, between 100 and 140, or between 100 and 120 subunits or monomers).

As used herein, the term "anionic polypeptide" refers to an anionic polymer that has at least 50% (e.g., 55%, 60%, 65%, 70%, 75%, 80%, 85%, 90%, 95%, or 100%) of its subunits or monomers being amino acids, such as acidic amino acids (e.g., glutamic acids and aspartic acids), or derivatives thereof. Aside from amino acids, an anionic polypeptide can also contain small organic molecules (e.g., organic acids), sugar molecules (e.g., monosaccharides or disaccharides), or nucleotides. In some embodiments, an anionic polypeptide can be a homopolymer where all of its subunits are the same. In other embodiments, an anionic polypeptide can be a heteropolymer that contains two or more different subunits. For example, an anionic polypeptide can be polyglutamic acid (PGA) (e.g., poly-gamma-glutamic acid), polyaspartic acid, and polycarboxyglutamic acid. In another example, an anionic polypeptide can contain a mixture of glutamic acids and aspartic acids. In some embodiments, at least 50% (e.g., 55%, 60%, 65%, 70%, 75%, 80%, 85%, 90%, 95%, or 100%) of the subunits or monomers in an anionic polypeptide can be glutamic acids and/or aspartic acids. An anionic polypeptide can contain at least two subunits or monomers (e.g., at least 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 subunits or monomers; between 100 and 400, between 120 and 400, between 140 and 400, between 160 and 400, between 180 and 400, between 200 and 400, between 220 and 400, between 240 and 400, between 260 and 400, between 280 and 400, between 300 and 400, between 320 and 400, between 340 and 400, between 360 and 400, between 380 and 400, between 100 and 380, between 100 and 360, between 100 and 340, between 100 and 320, between 100 and 300, between 100 and 280, between 100 and 260, between 100 and 240, between 100 and 220, between 100 and 200, between 100 and 180, between 100 and 160, between 100 and 140, or between 100 and 120 subunits or monomers).

As used herein, the term "anionic polysaccharide" refers to an anionic polymer that has at least 50% (e.g., 55%, 60%, 65%, 70%, 75%, 80%, 85%, 90%, 95%, or 100%) of its subunits or monomers being sugar molecules, such as monosaccharides (e.g., fructose, galactose, and glucose) and disaccharides (e.g., hyaluronic acid, lactose, maltose, and sucrose), or derivatives thereof. Aside from sugar molecules, an anionic polysaccharide can also contain small organic molecules (e.g., organic acids), amino acids (e.g., glutamic acids or aspartic acids), or nucleotides. In some embodiments, an anionic polysaccharide can be a homopolymer where all of its subunits are the same. In other embodiments, an anionic polysaccharide can be a heteropolymer that contains two or more different subunits. For example, an anionic polysaccharide can be hyaluronic acid (HA), heparin, heparin sulfate, or glycosaminoglycan. In some embodiments, at least 50% (e.g., 55%, 60%, 65%, 70%, 75%, 80%, 85%, 90%, 95%, or 100%) of the subunits or monomers in an anionic polysaccharide can be HA. An anionic polysaccharide can contain at least two subunits or monomers (e.g., at least 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 subunits or monomers; between 100 and 400, between 120 and 400, between 140 and 400, between 160 and 400, between 180 and 400, between 200 and 400, between 220 and 400, between 240 and 400, between 260 and 400, between 280 and 400, between 300 and 400, between 320 and 400, between 340 and 400, between 360 and 400, between 380 and 400, between 100 and 380, between 100 and 360, between 100 and 340, between 100 and 320, between 100 and 300, between 100 and 280, between 100 and 260, between 100 and 240, between 100 and 220, between 100 and 200, between 100 and 180, between 100 and 160, between 100 and 140, or between 100 and 120 subunits or monomers).

BRIEF DESCRIPTION OF THE DRAWINGS

The present application includes the following figures. The figures are intended to illustrate certain embodiments and/or features of the compositions and methods, and to supplement any description(s) of the compositions and methods. The figures do not limit the scope of the compositions and methods, unless the written description expressly indicates that such is the case.

d one or more DNA-binding protein target sequences, wherein at least one DNA-binding protein target sequence forms a double-stranded duplex with a complementary polynucleotide sequence.

Figure 2A:
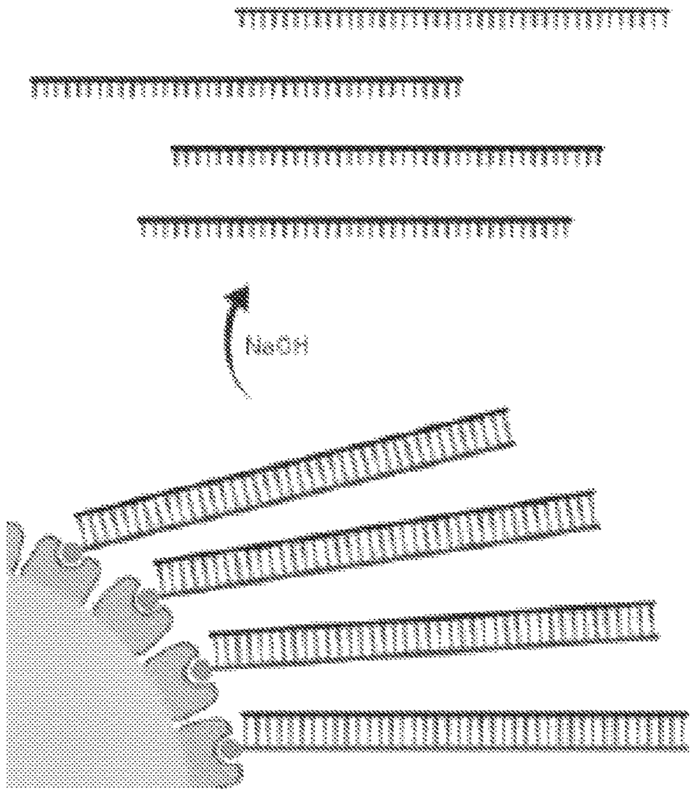

FIG. 2A shows a method of generating long ssDNAs by biotinylating one strand of a dsDNA, which was then denatured to release the non-biotinylated strand.

Figure 2B:
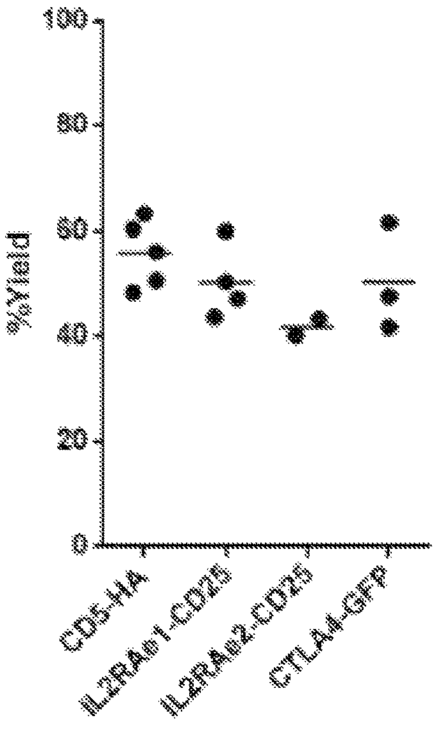

FIG. 2B shows the percentage yield of ssDNA for four different constructs as a percentage of maximum theoretic yield.

Figure 3:
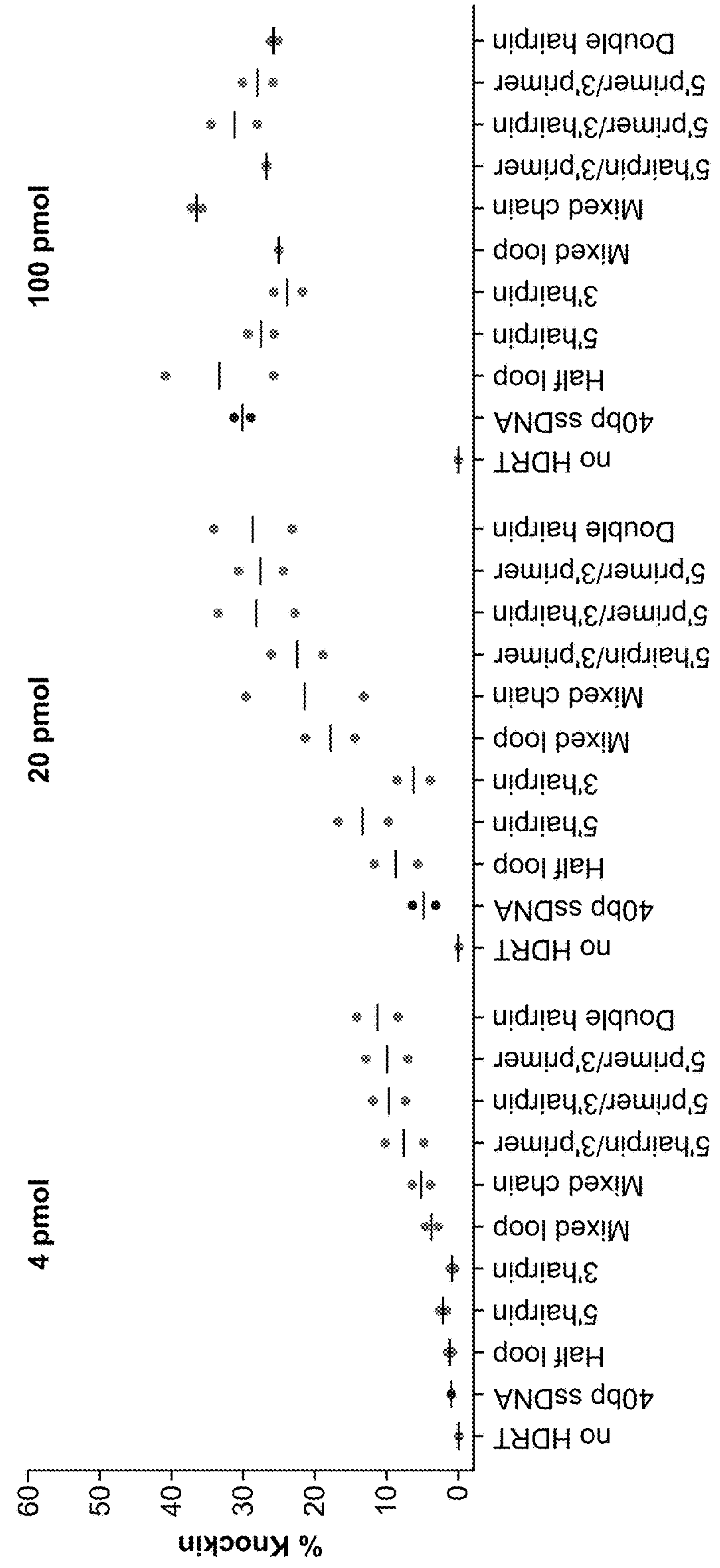

FIG. 3 shows the knock-in efficiency at different amounts of constructs that are less than 40 bps.

Figure 4A:
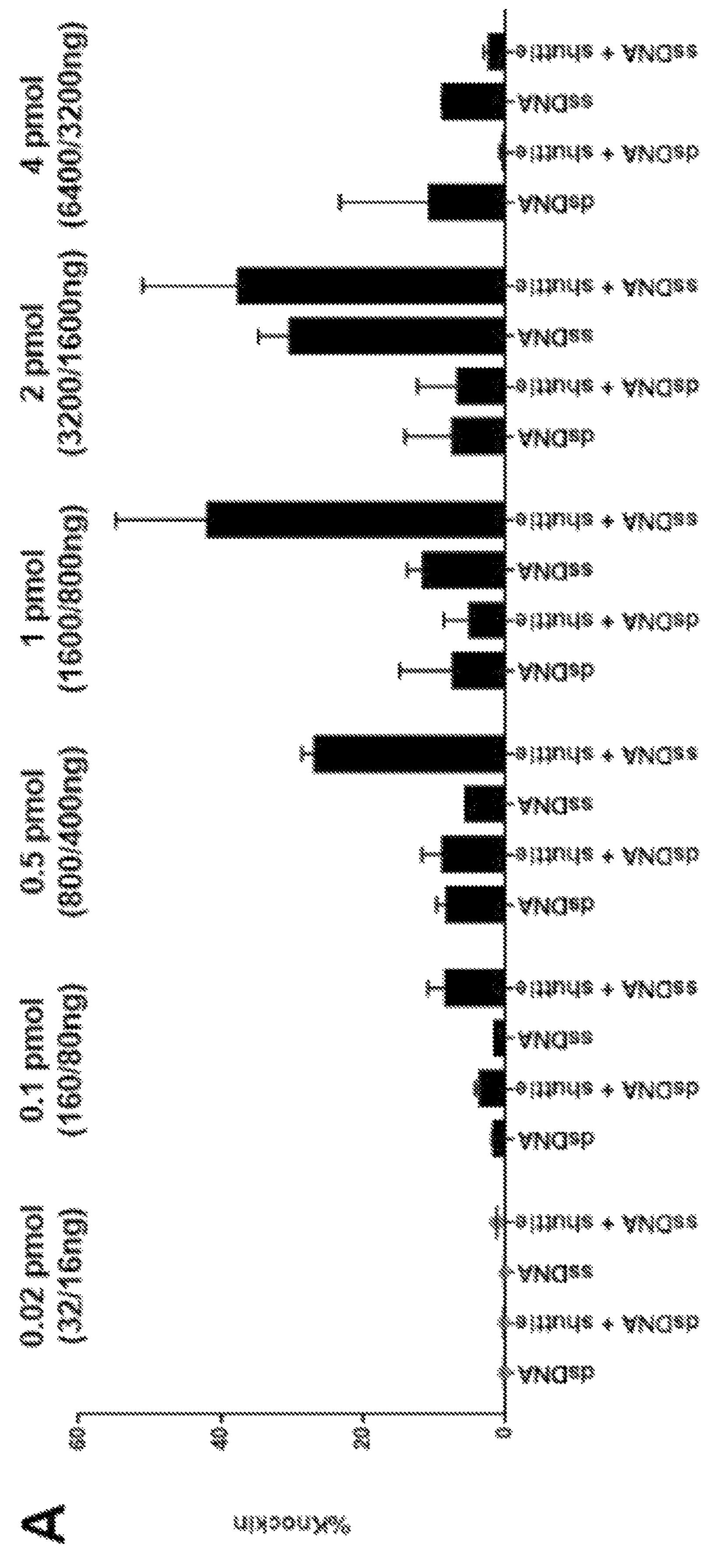
Figure 4B:
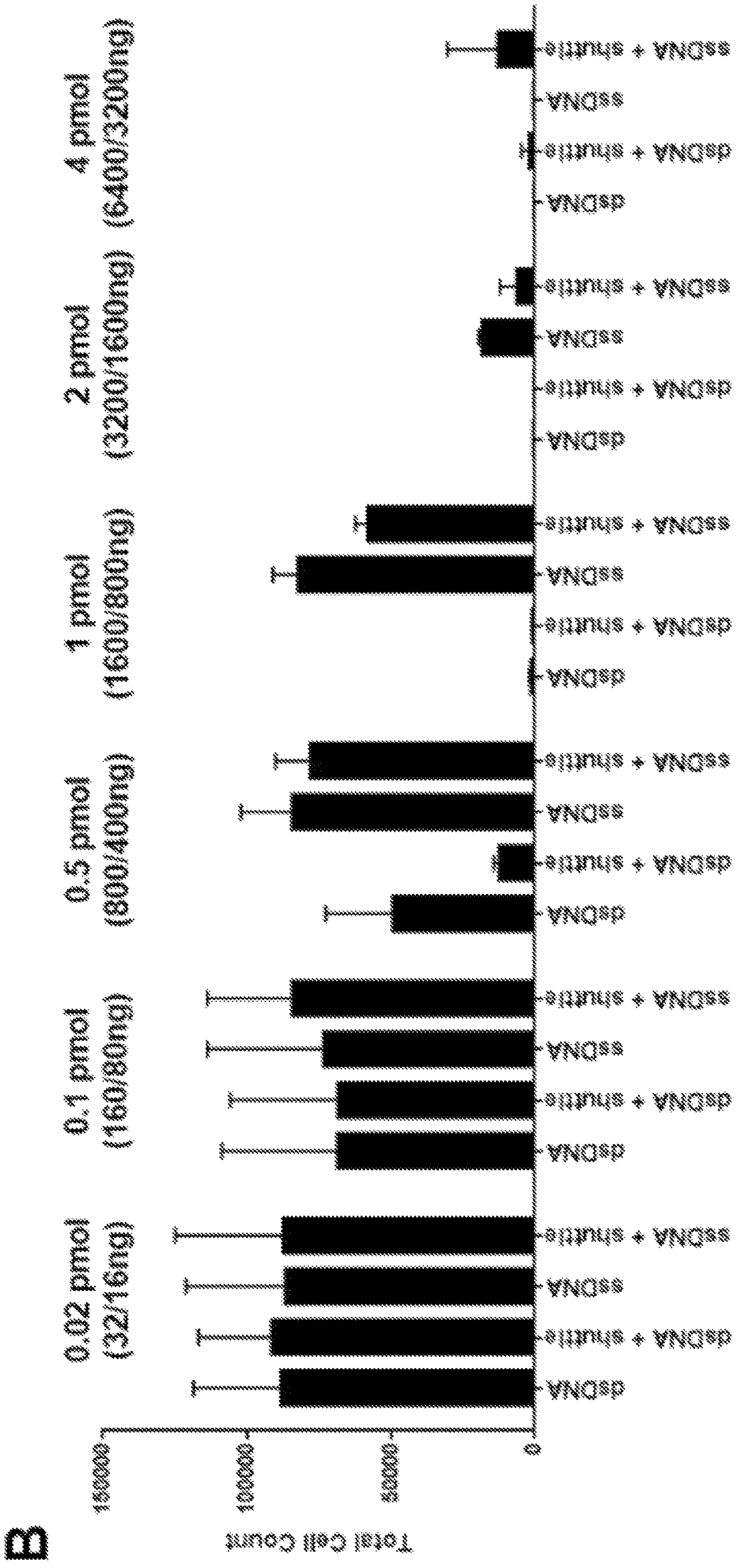
Figure 4C:
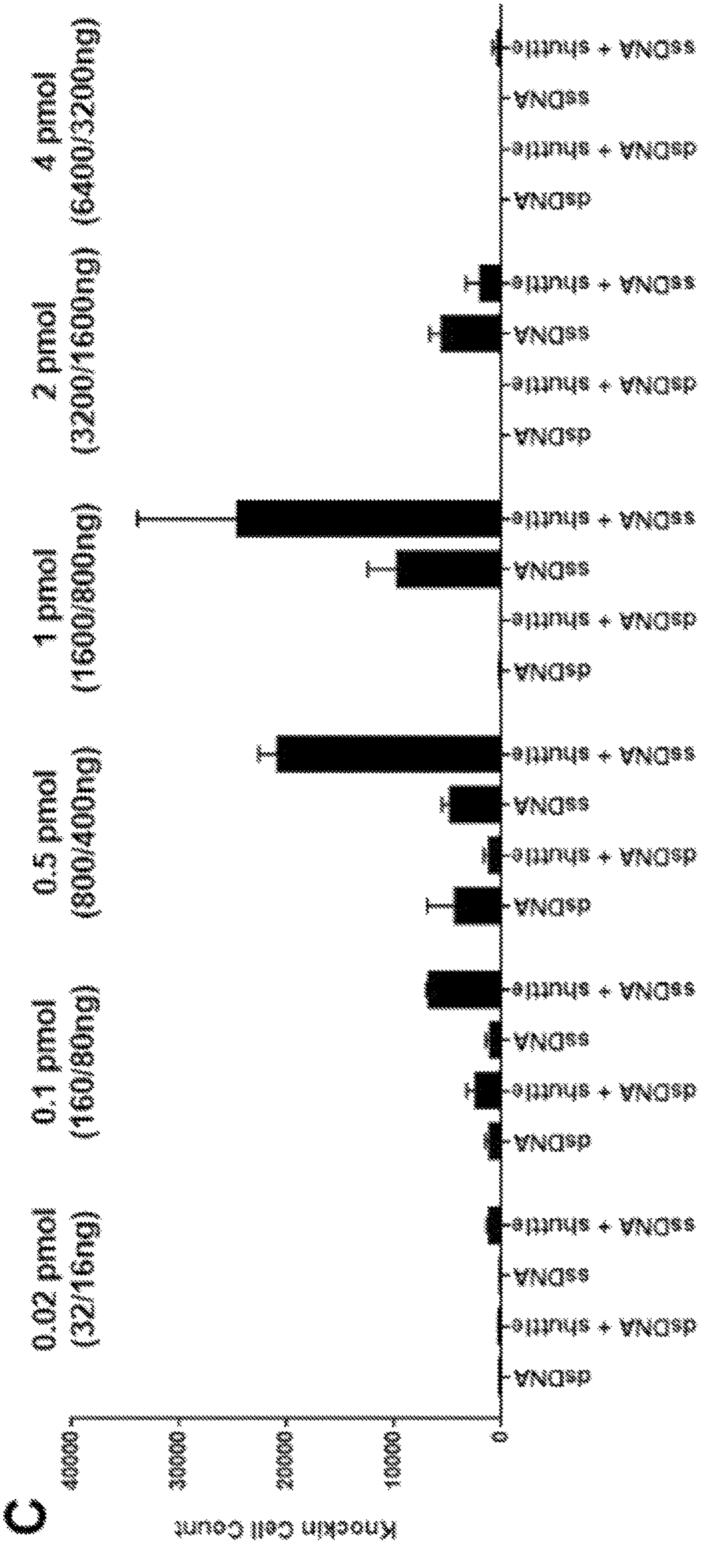

FIGS. 4A-4C show the percentage of knock-in, total cell count, and knock-in cell count at different amounts of primer donor constructs ("ssDNA+shuttle"), compared against dsDNA, dsDNA with shuttle ends, and ssDNA, when targeting an HA tag to the CD5 locus.

Figure 5A:
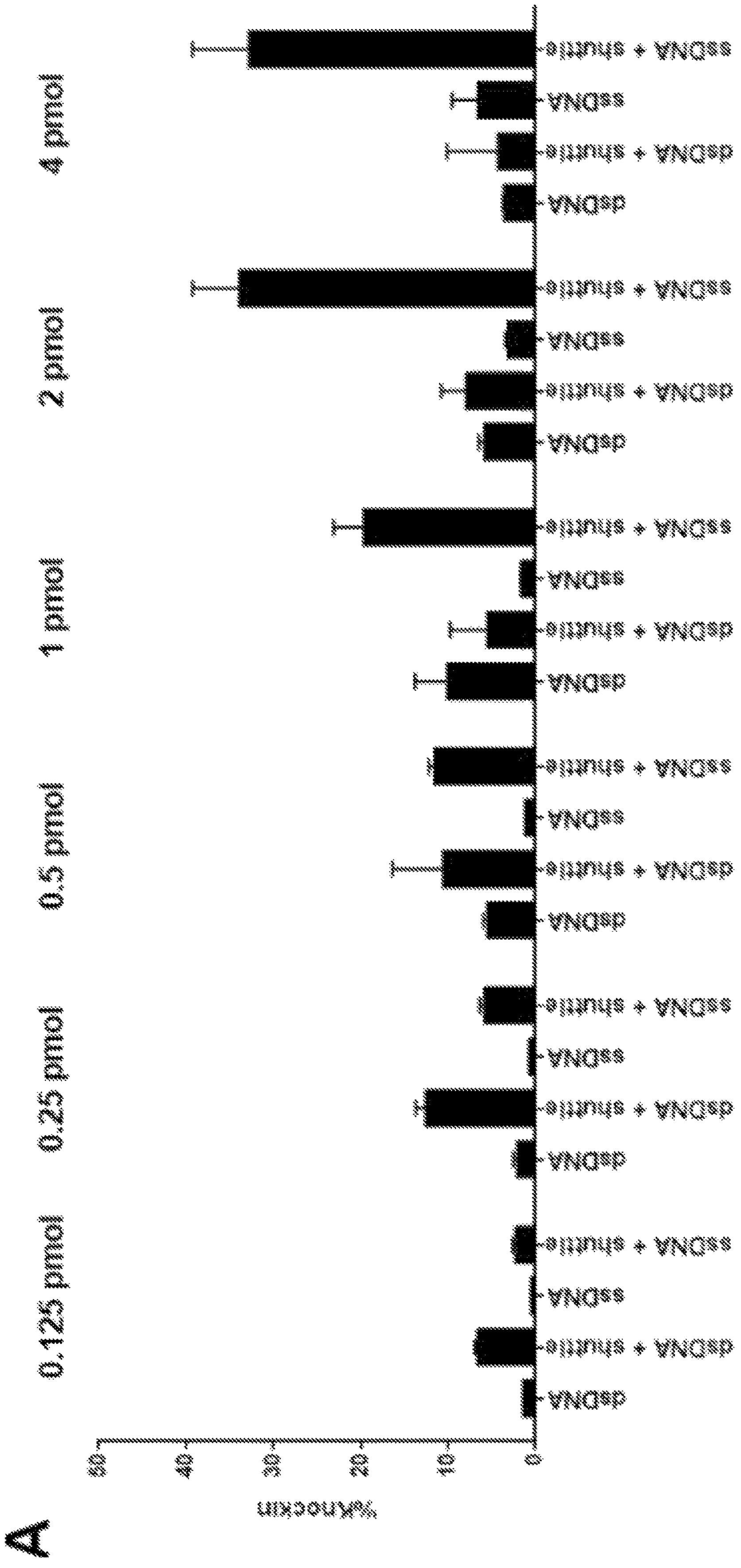
Figure 5B:
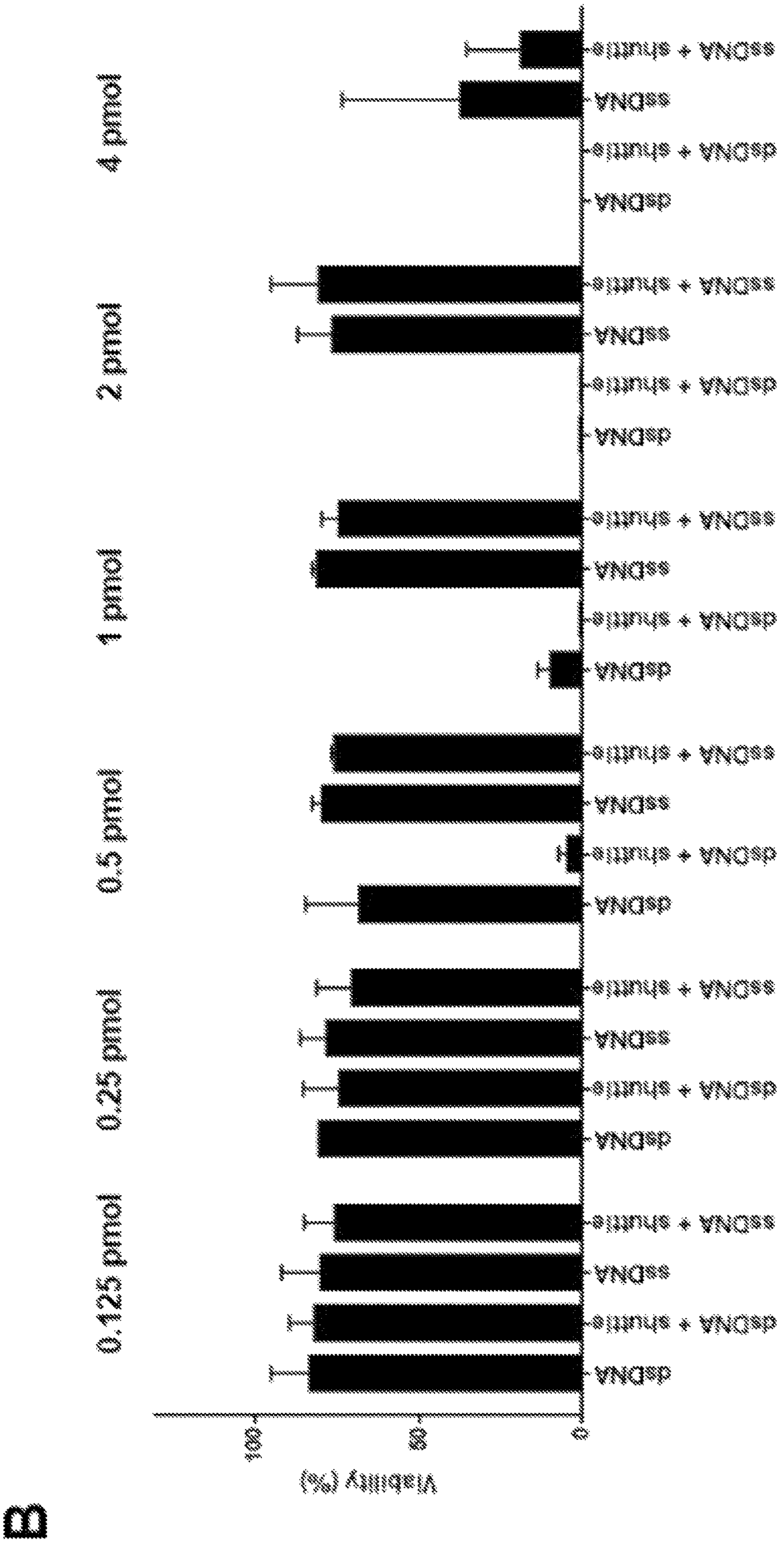
Figure 5C:
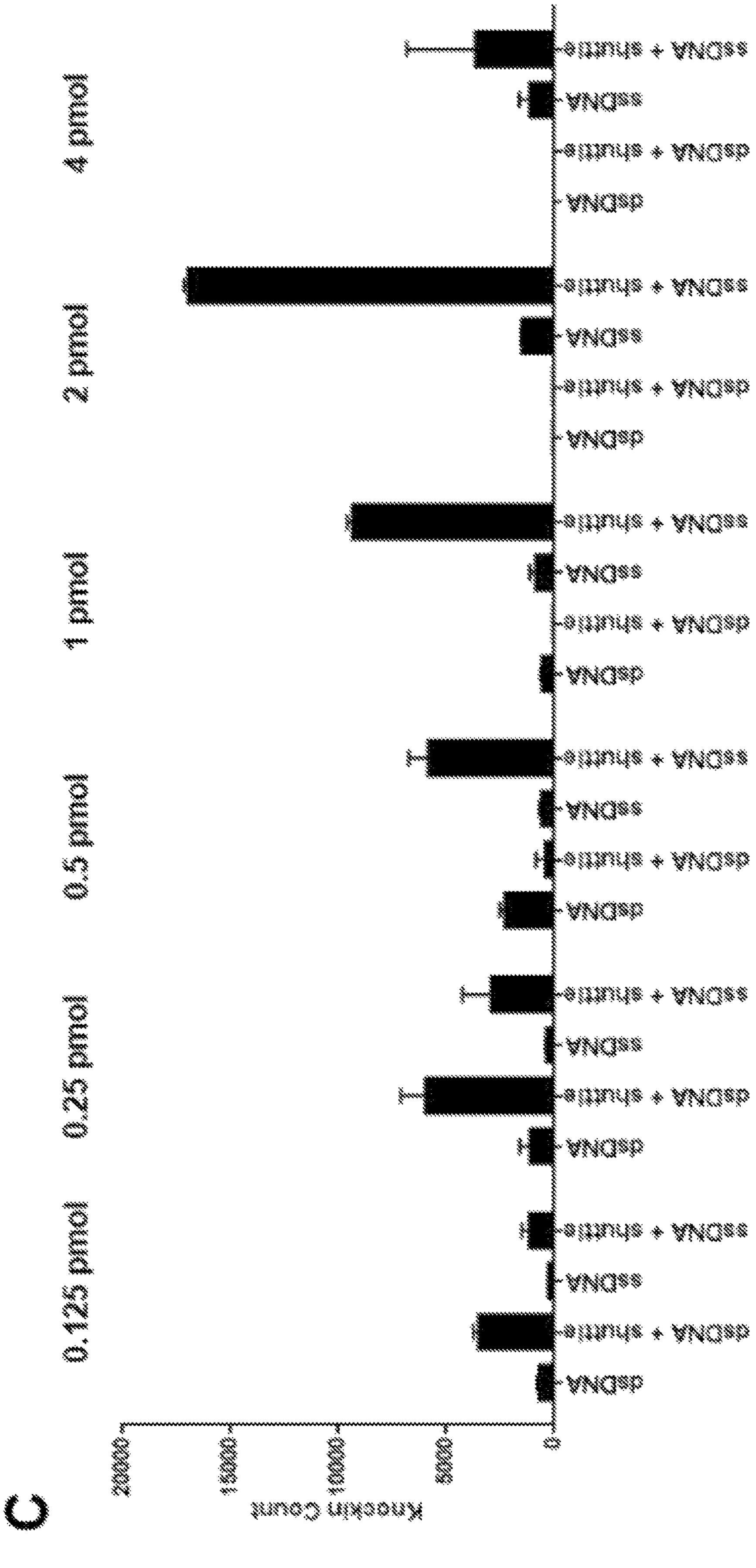

FIGS. 5A-5C show the percentage of knock-in, total cell count, and knock-in cell count at different amounts of primer donor constructs ("ssDNA+shuttle"), compared against dsDNA, dsDNA with shuttle ends, and ssDNA, when targeting a CD25-GFP cDNA knock-in to the IL2RA locus.

Figure 6A:
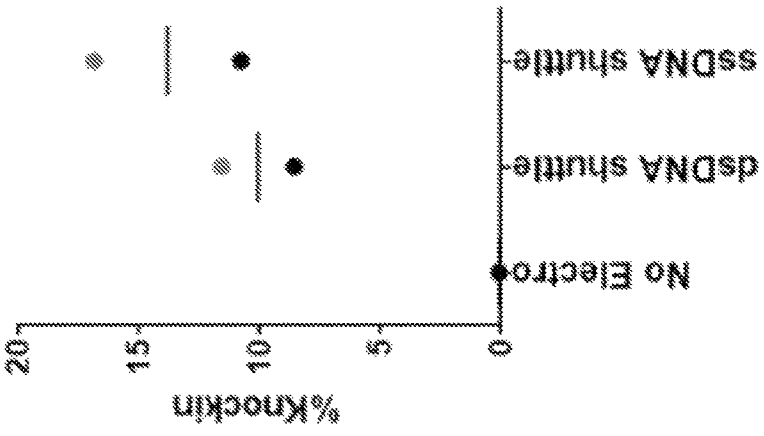
Figure 6B:
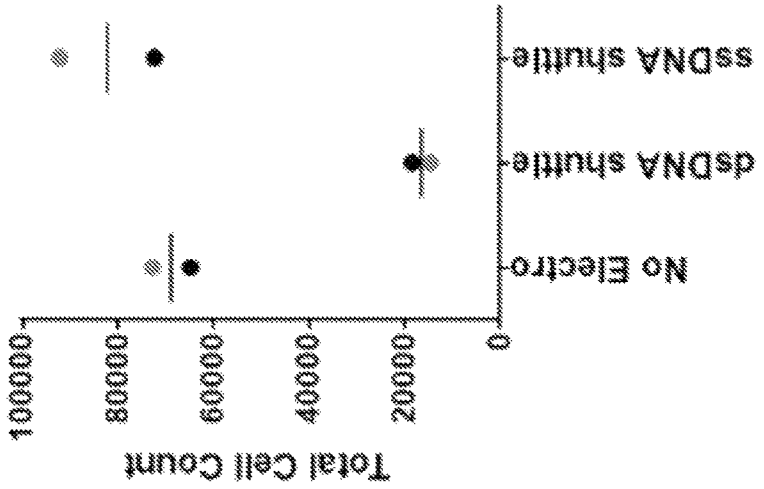
Figure 6C:
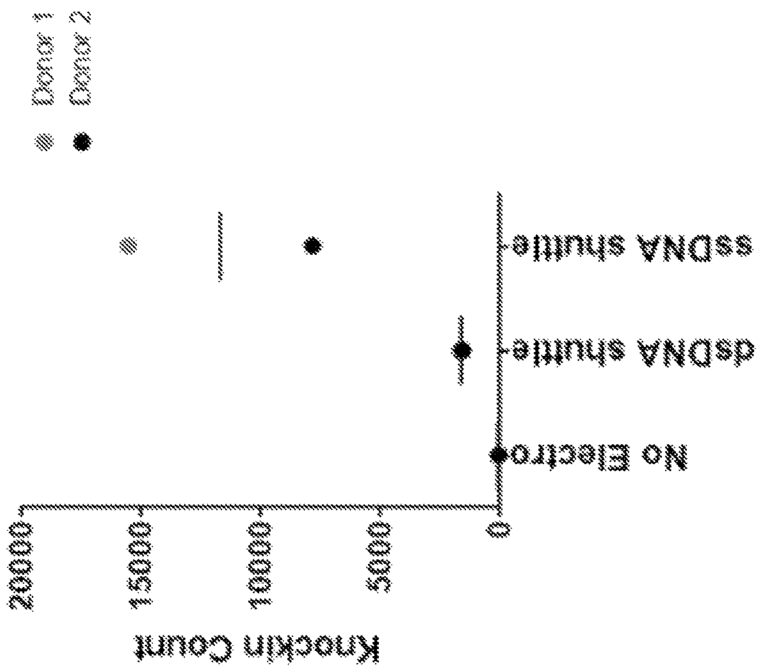
Figure 7A:
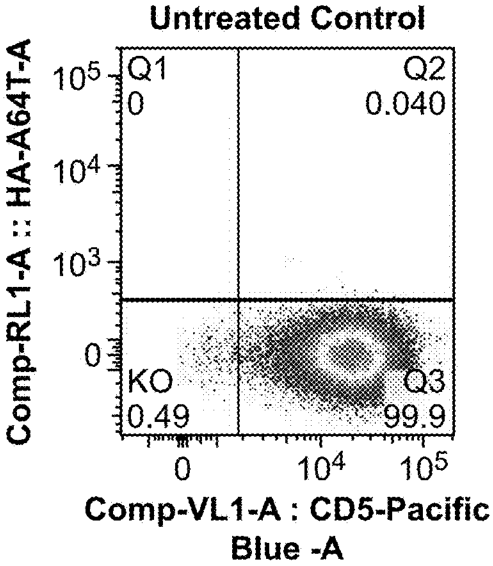
Figure 7B:
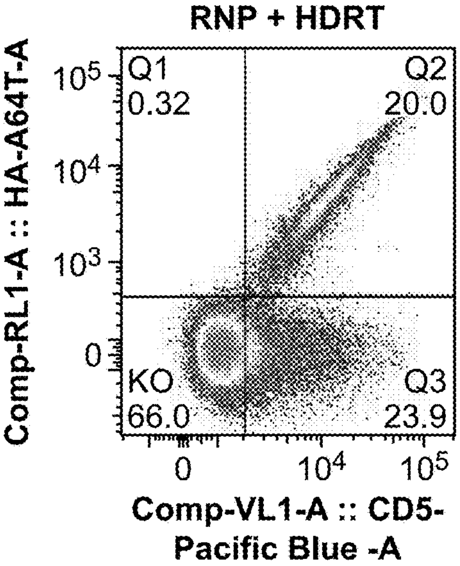
Figure 7C:
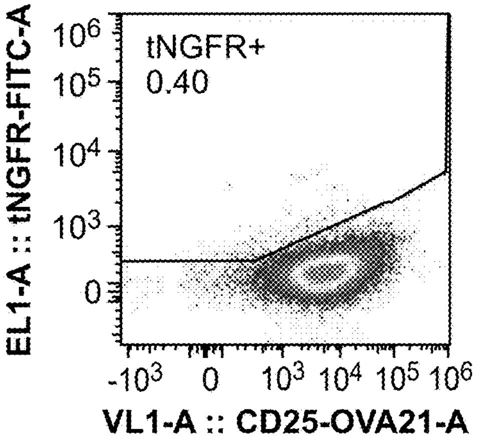
Figure 7D:
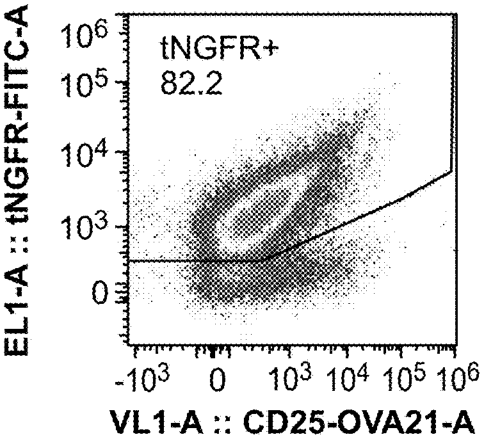
Figure 7E:
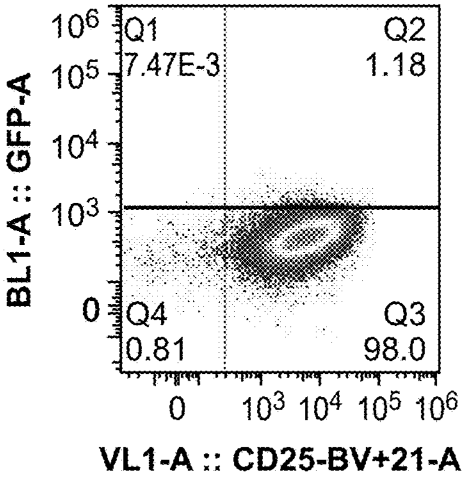
Figure 7F:
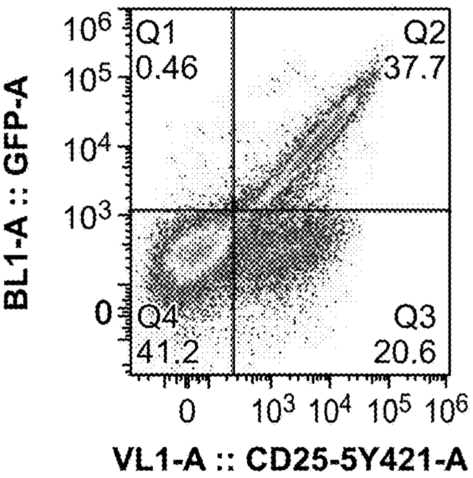
Figure 8A:
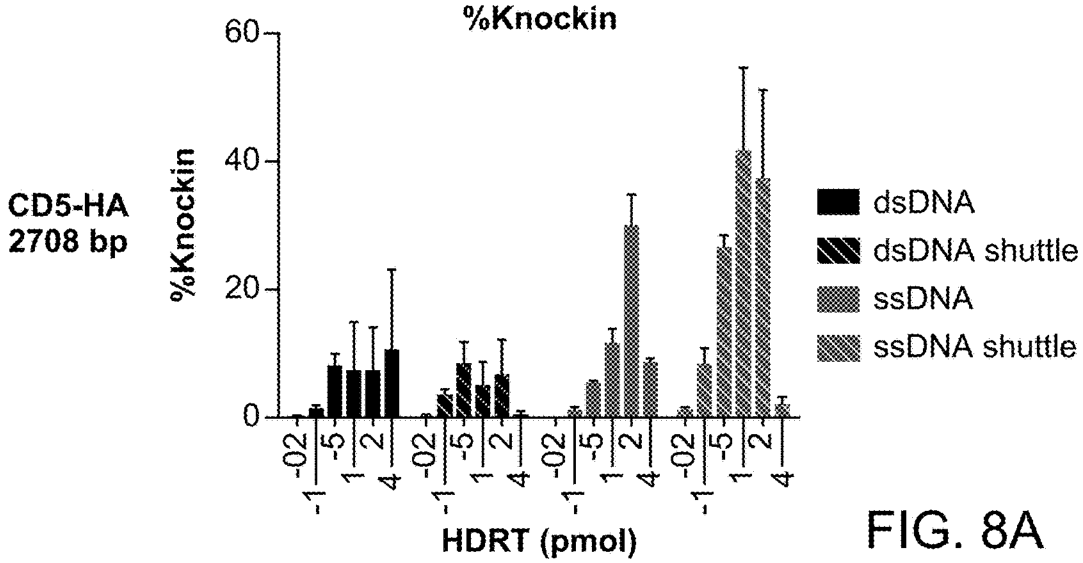
Figure 8B:
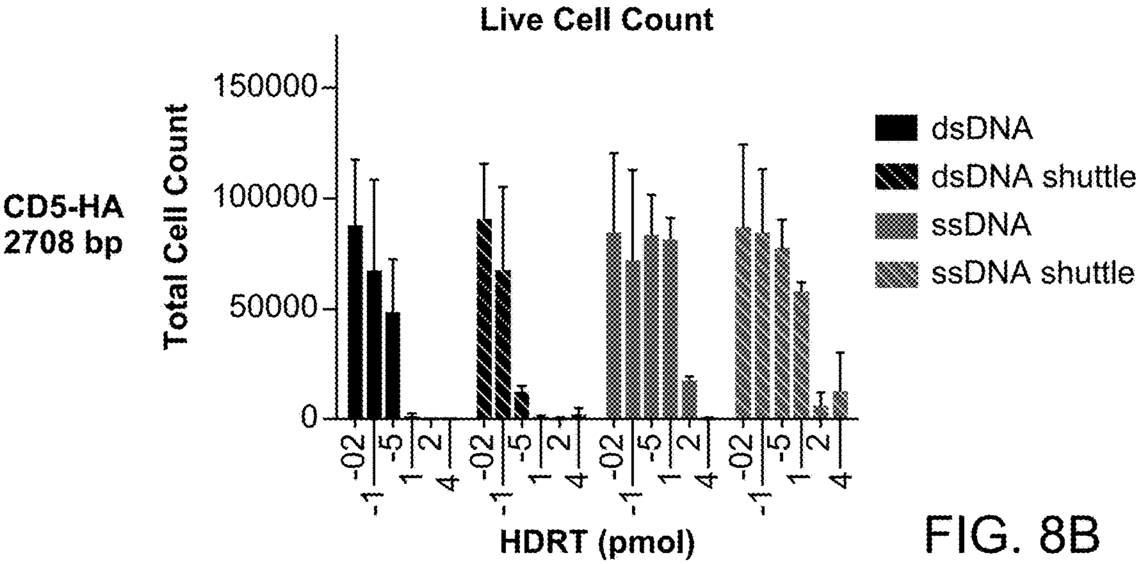
Figure 8C:
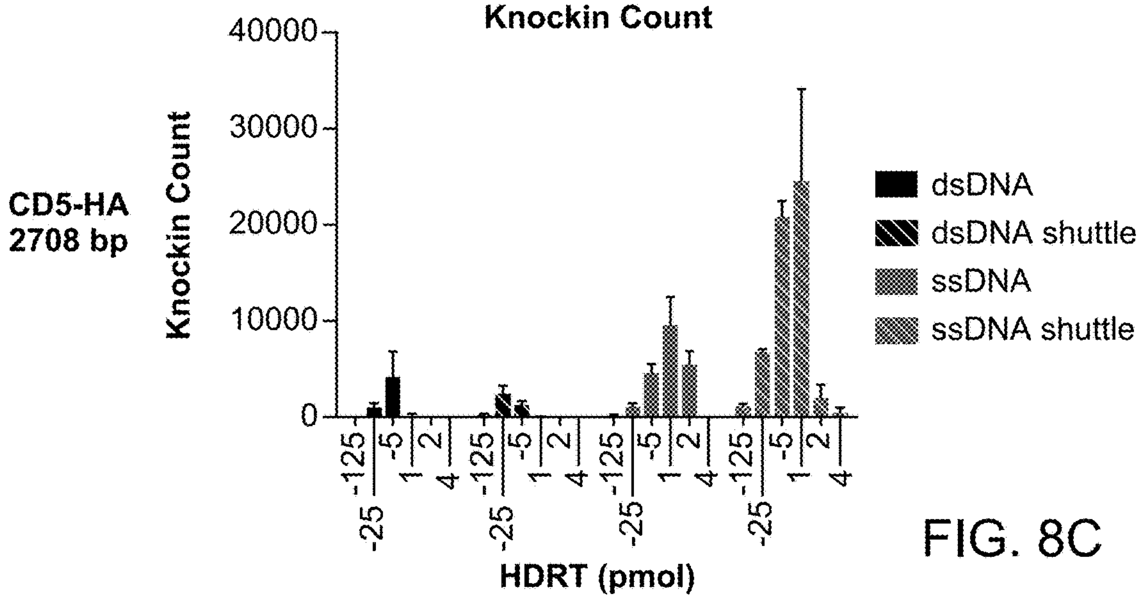
Figure 8D:
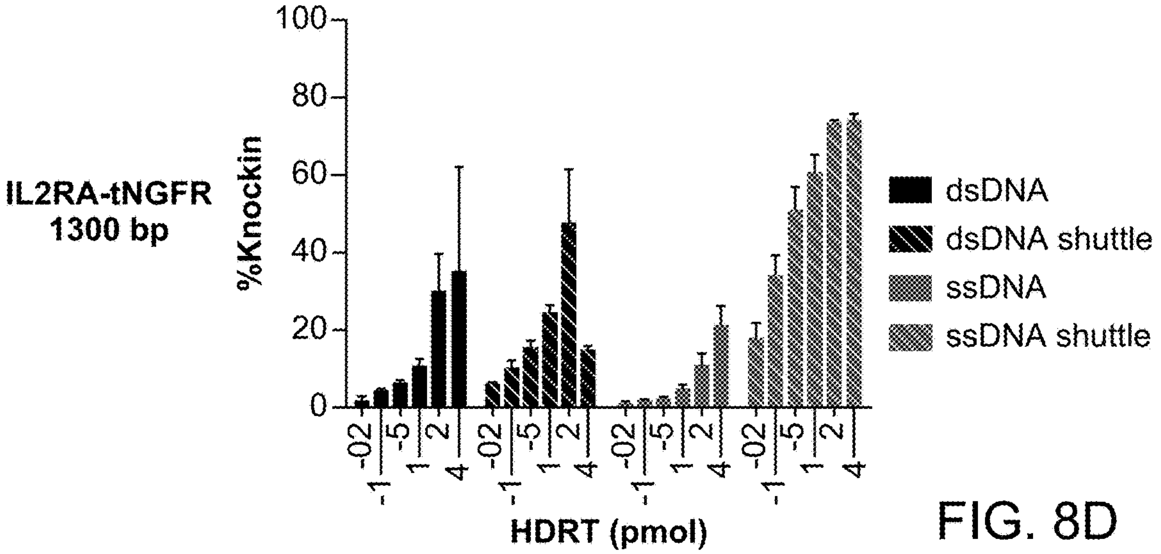
Figure 8E:
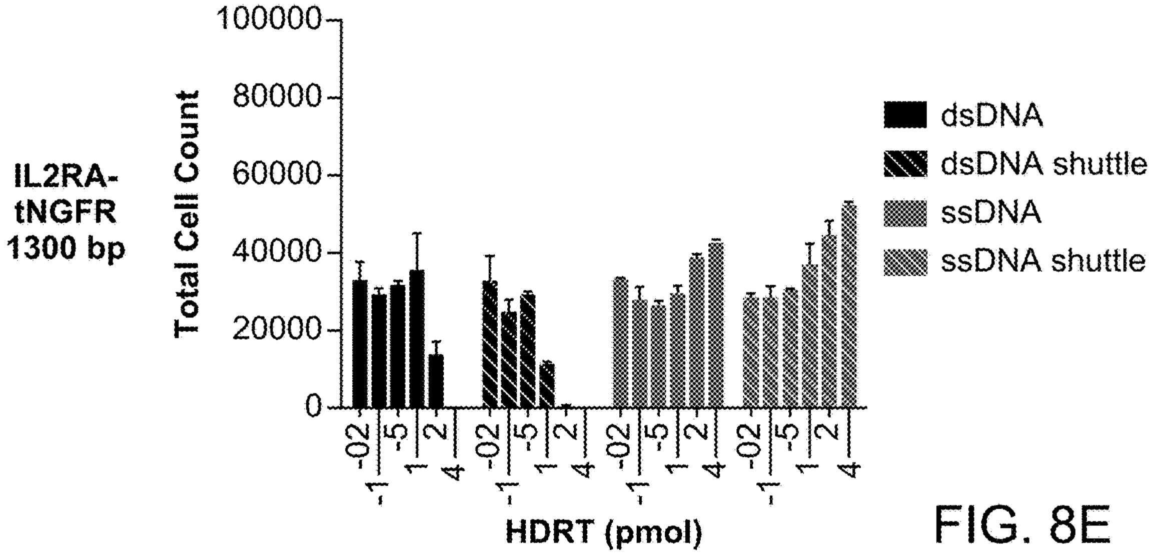
Figure 8F:
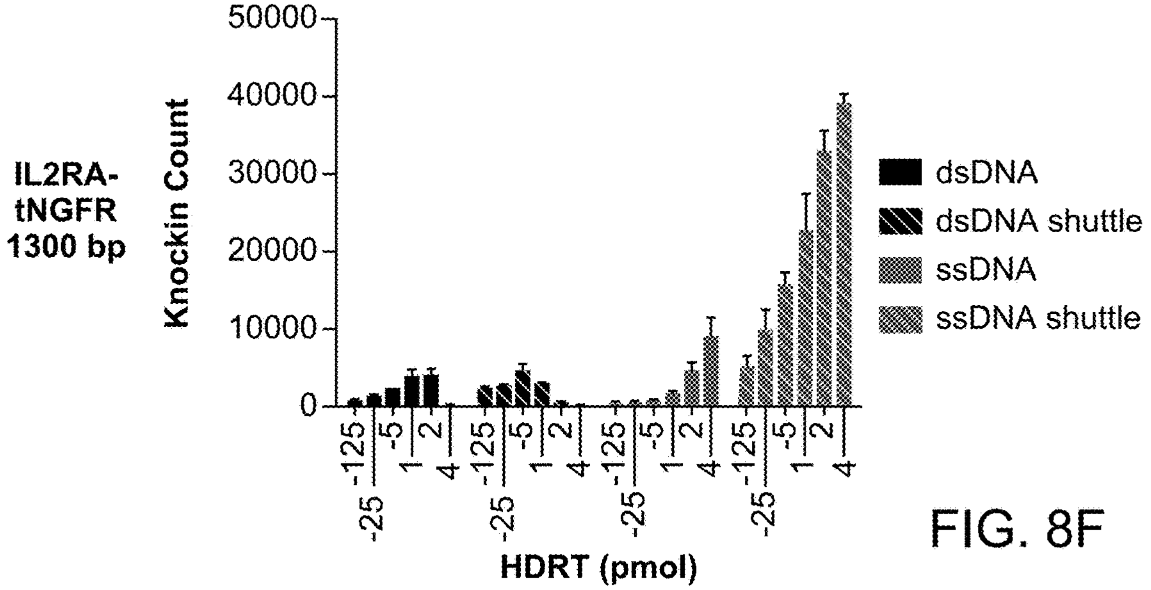
Figure 8G:
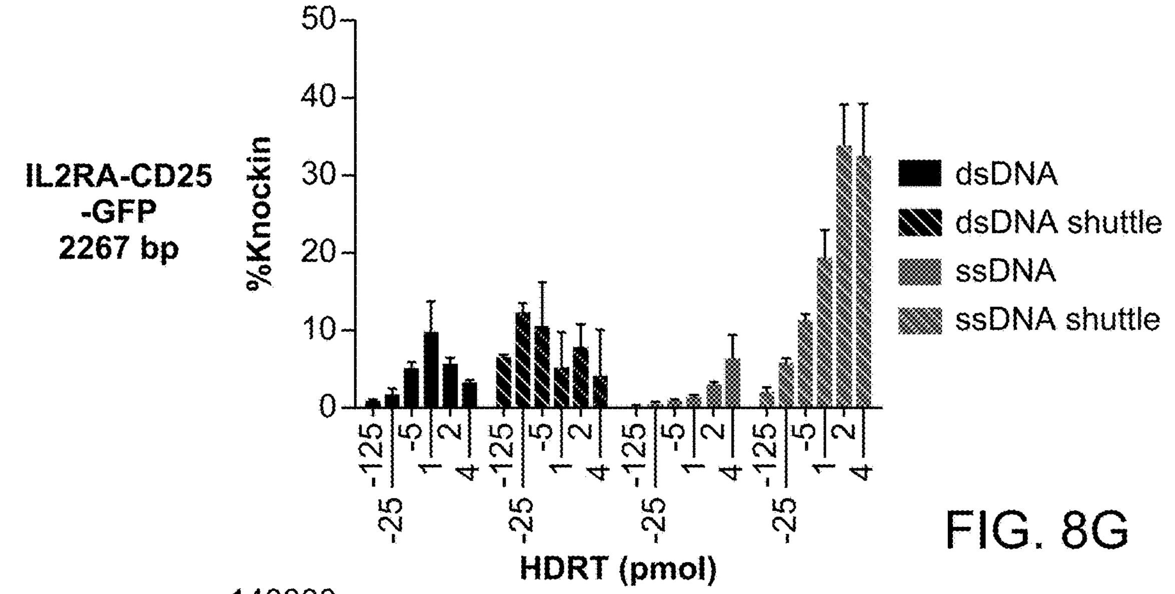
Figure 8H:
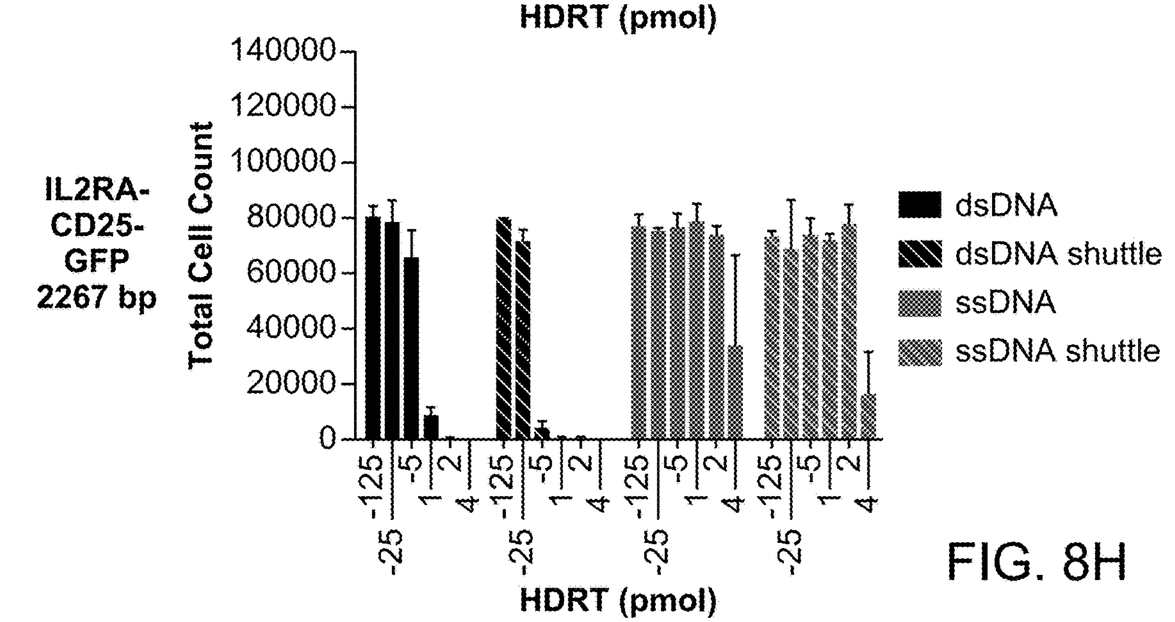
Figure 8I:
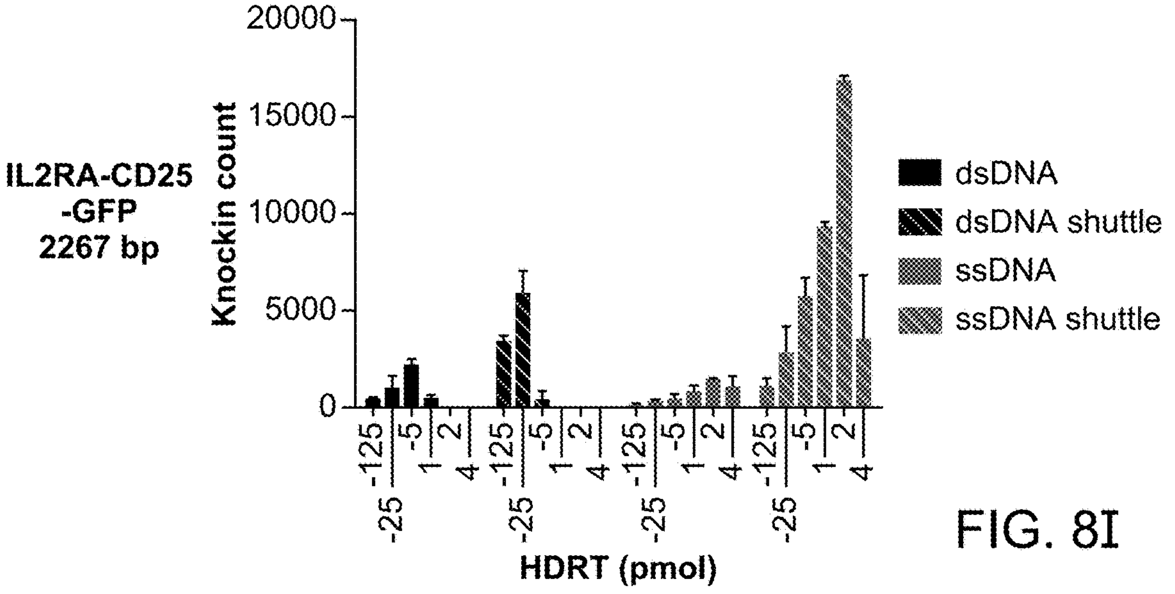

FIGS. 6A-6C show the percentage of knock-in, total cell count, and knock-in cell count at different amounts of primer donor constructs ("ssDNA+shuttle"), compared against dsDNA, dsDNA with shuttle ends, and ssDNA, when targeting an NY-ESO-1 specific T cell receptor to the endogenous TRAC locus.

FIGS. 7A-7F show representative flow plots demonstrating knock-in populations of constructs CD5-HA, IL2RA-tNGFR, and IL2RA-CD25-GFP.

FIGS. 8A-8I show knock-in efficiency, live cell counts, and absolute number of knock-in cells for constructs CD5-HA, IL2RA-tNGFR, and IL2RA-CD25-GFP with increasing concentration of HDRT.

Figure 9B:
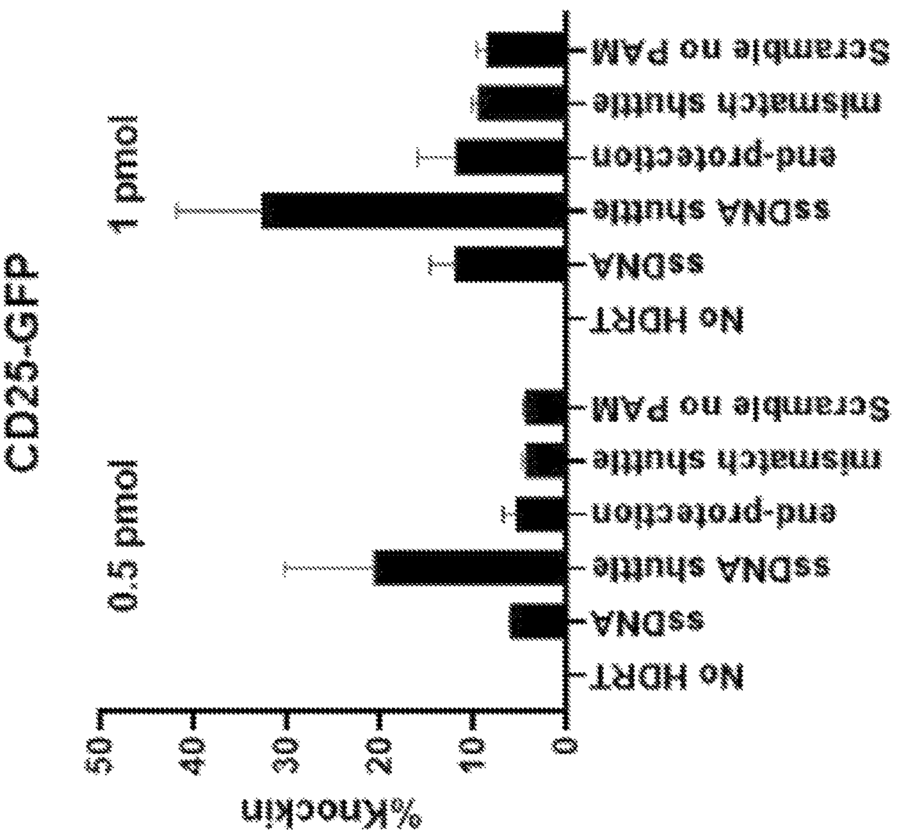
Figure 9A:
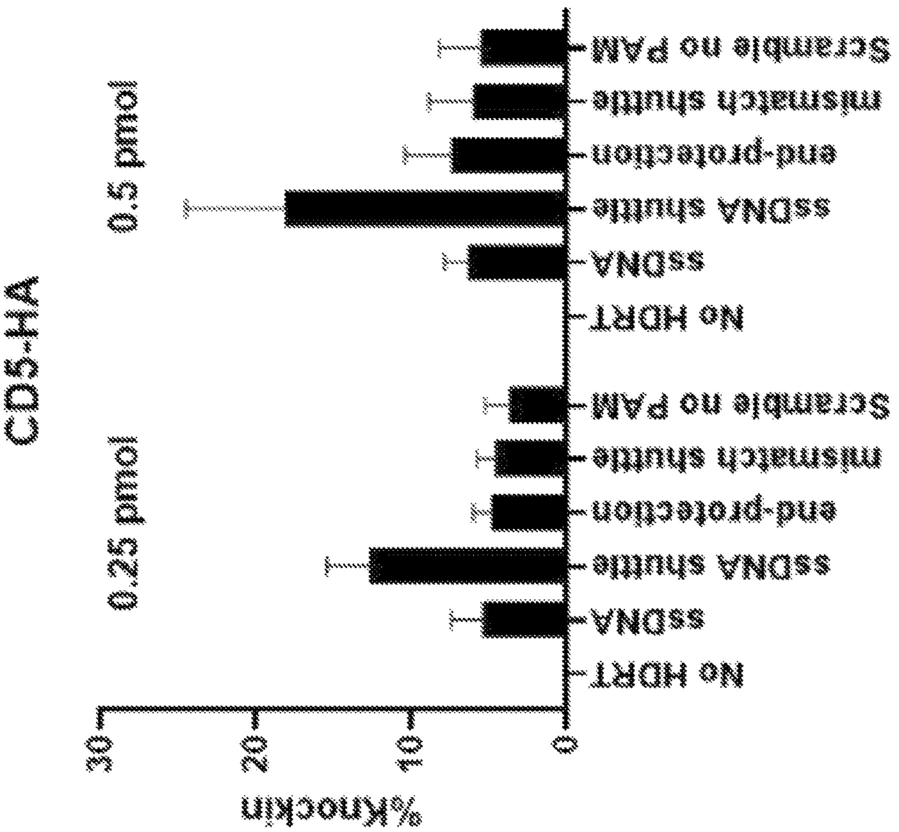

FIGS. 9A and 9B show that ssDNA shuttle with sequence complementary to the corresponding gRNA increased knock-in efficiency in comparison to ssDNA control.

Figure 9D:
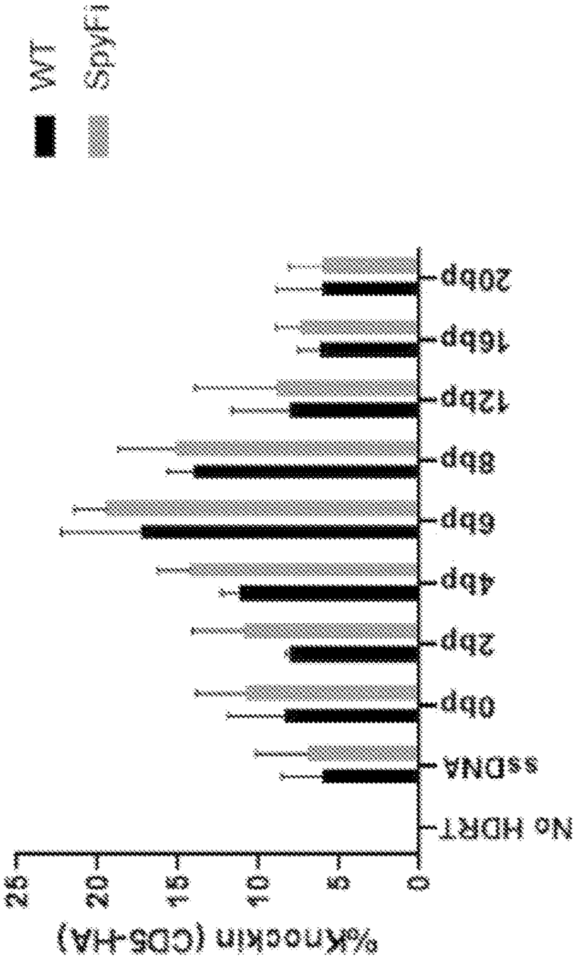
Figure 9C:
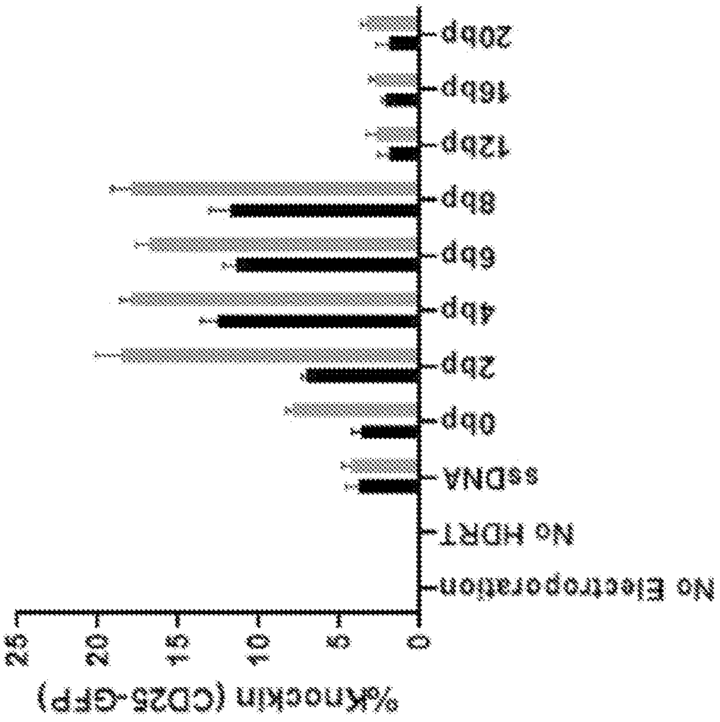

FIGS. 9C and 9D show knock-in efficiencies of ssDNA shuttle HDRTs each containing a different number of mismatched bases to alter gRNA binding affinity. HDRTs with 2-8 bp mismatch demonstrated highest increase in knock-in efficiency.

Figure 9E:
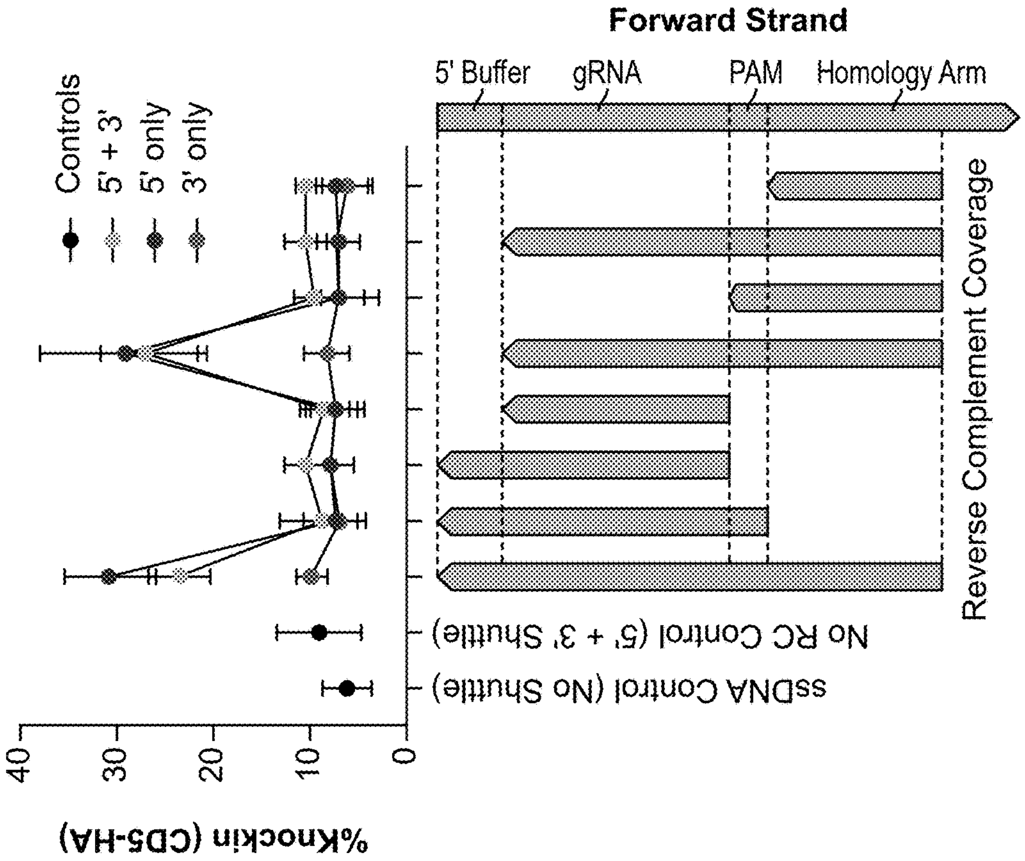
Figure 9F:
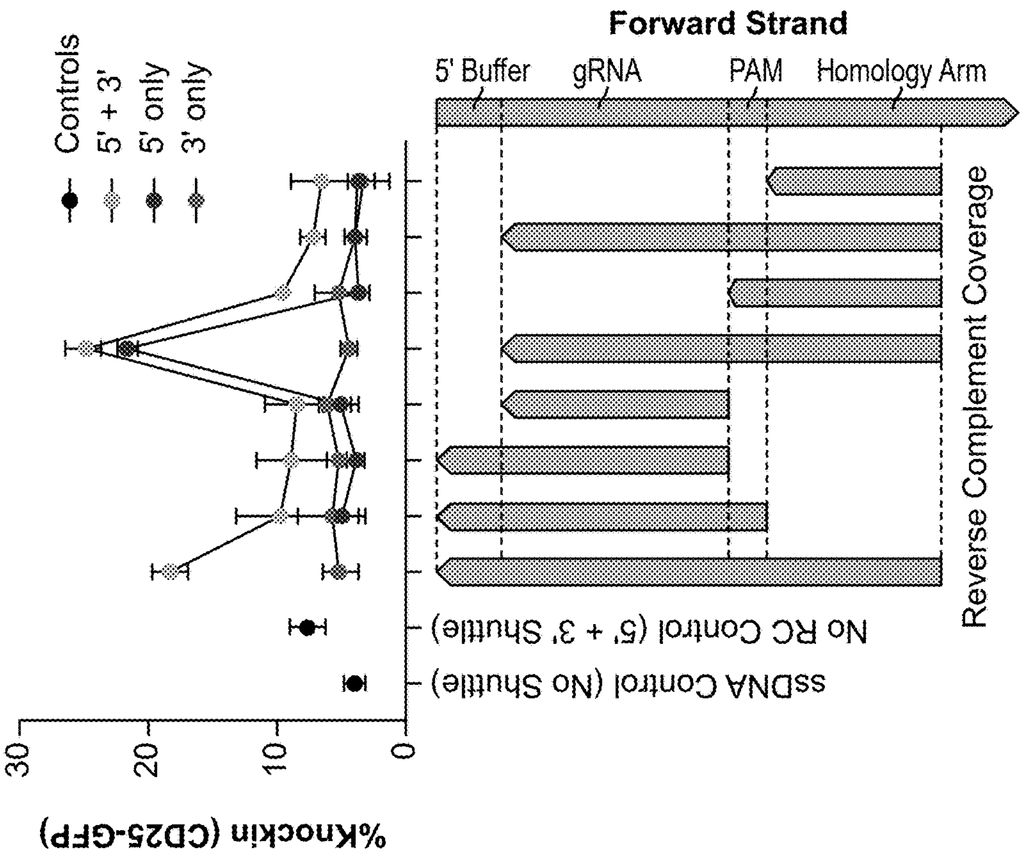

FIGS. 9E and 9F show knock-in efficiencies of ssDNA with dsDNA ends covering different segments of the shuttle sequence and flanking homology arms.

Figure 9H:
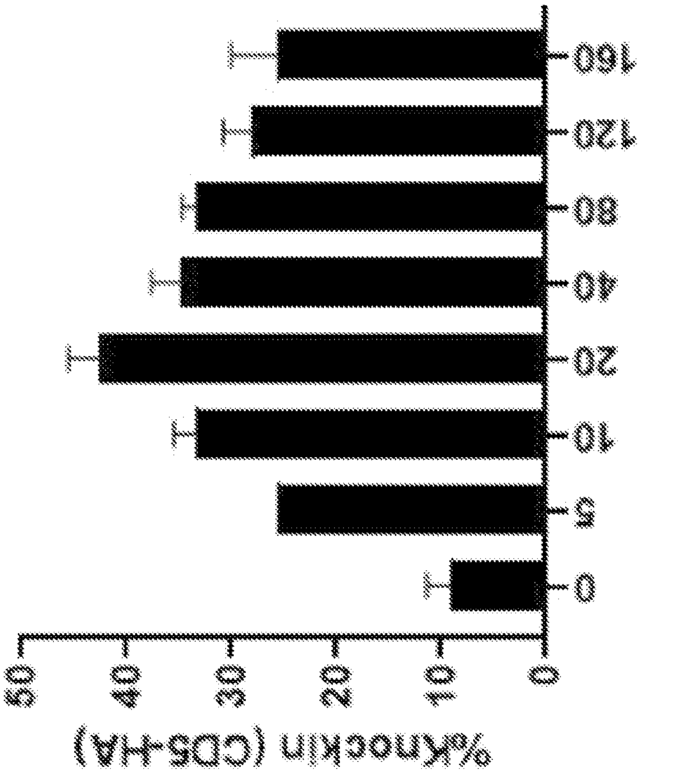
Figure 9G:
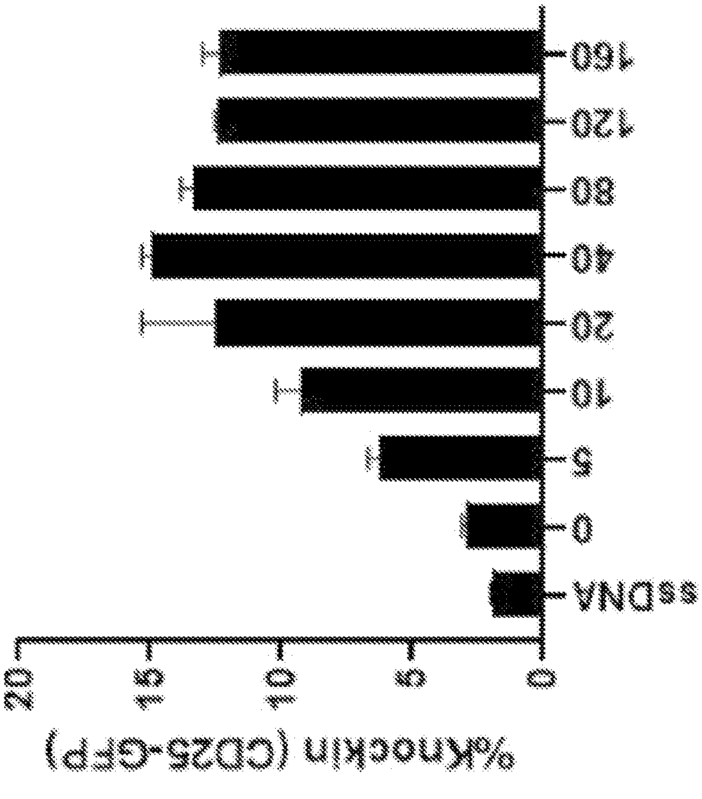

FIGS. 9G and 9H show knock-in efficiencies of ssDNA with dsDNA shuttle ends including the gRNA sequence, PAM sequence, and varied amount of overlap with the flanking 5' homology arm.

Figure 9I:
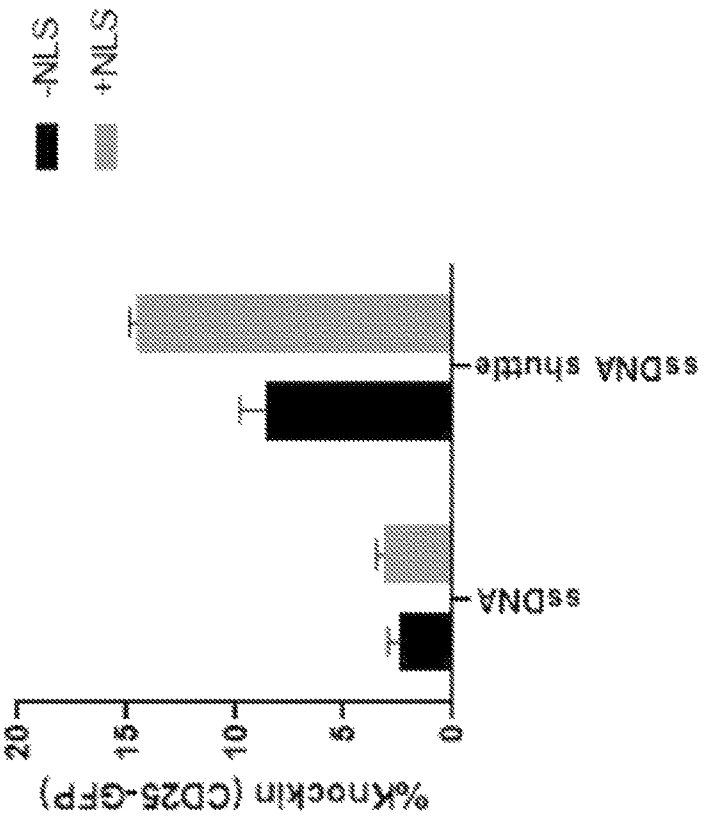
Figure 9J:
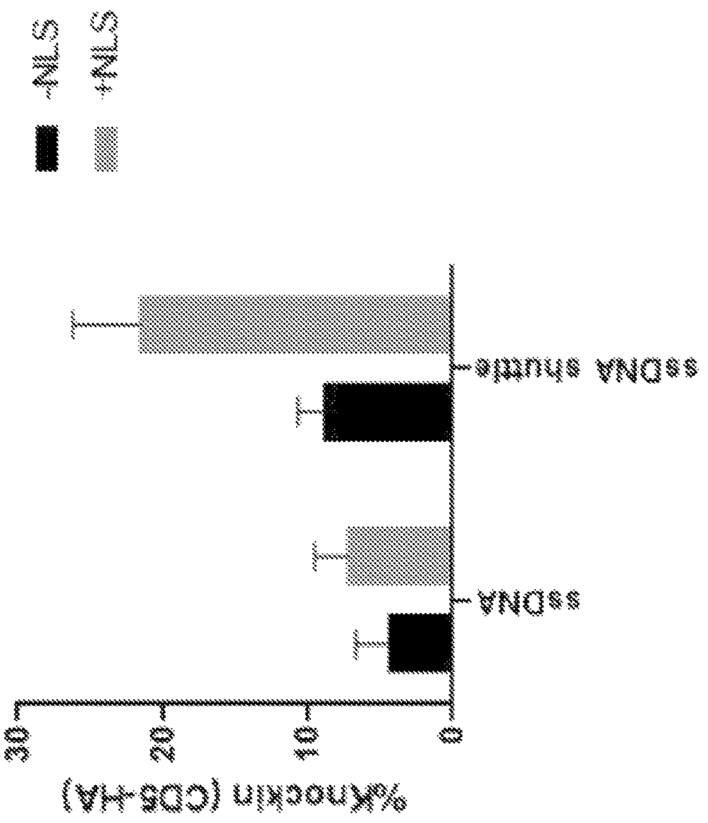

FIGS. 9I and 9J show Cas9 variants including a Nuclear Localization Sequence (NLS) provide additional improvements to knock-in efficiency.

Figure 9L:
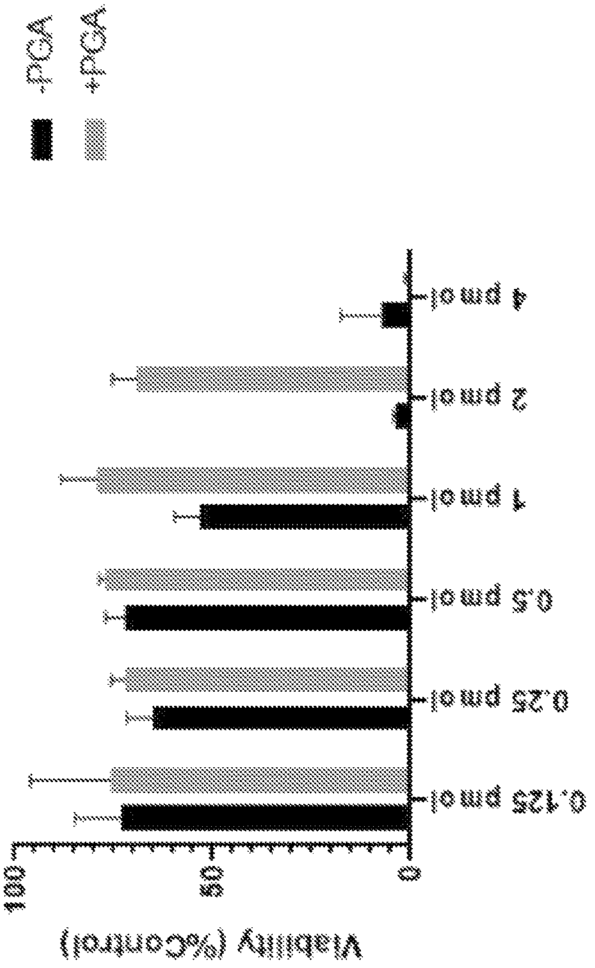
Figure 9K:
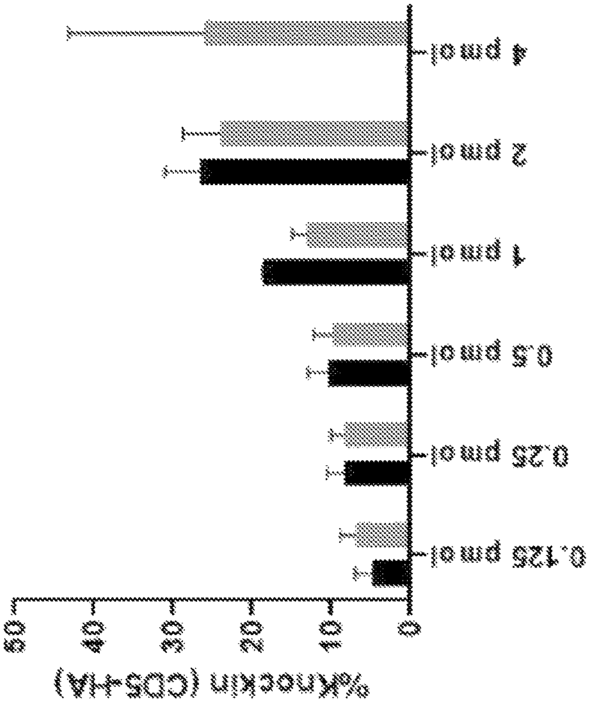

FIGS. 9K and 9L show that anionic polymers provided additional reduction of toxicity in combination with ssDNA shuttle sequences.

Figure 10A:
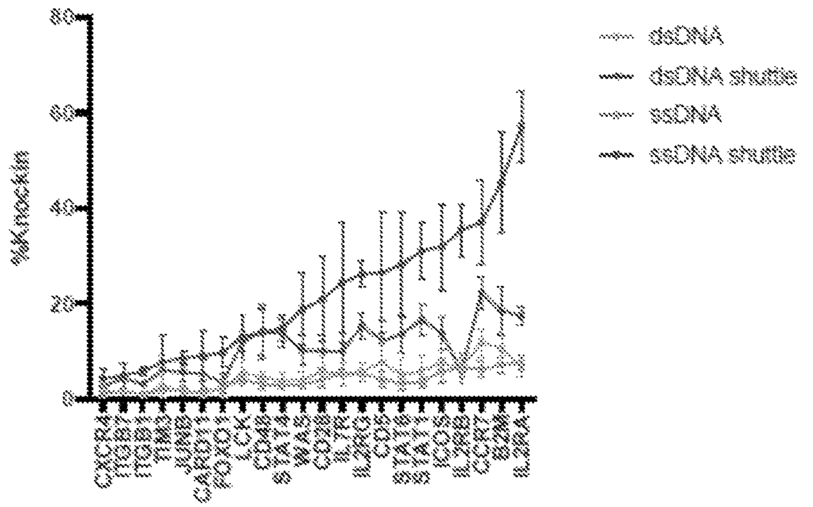
Figure 10B:
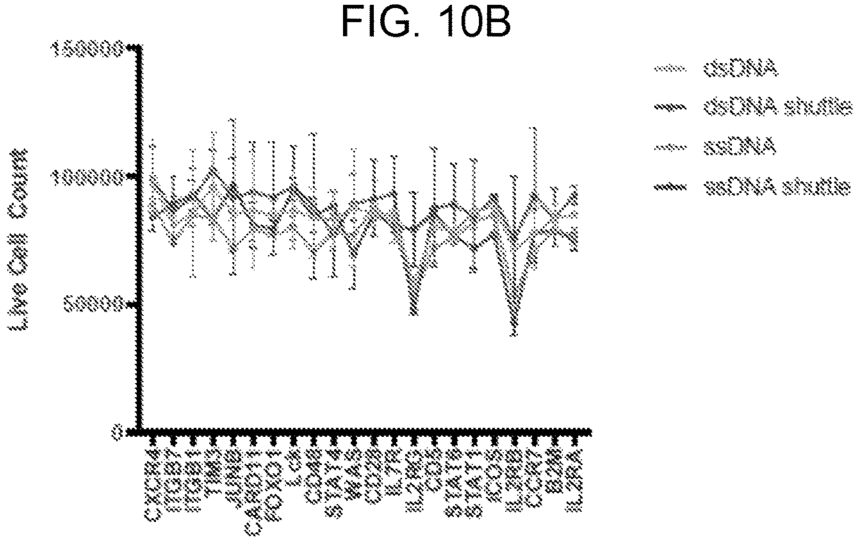
Figure 10C:
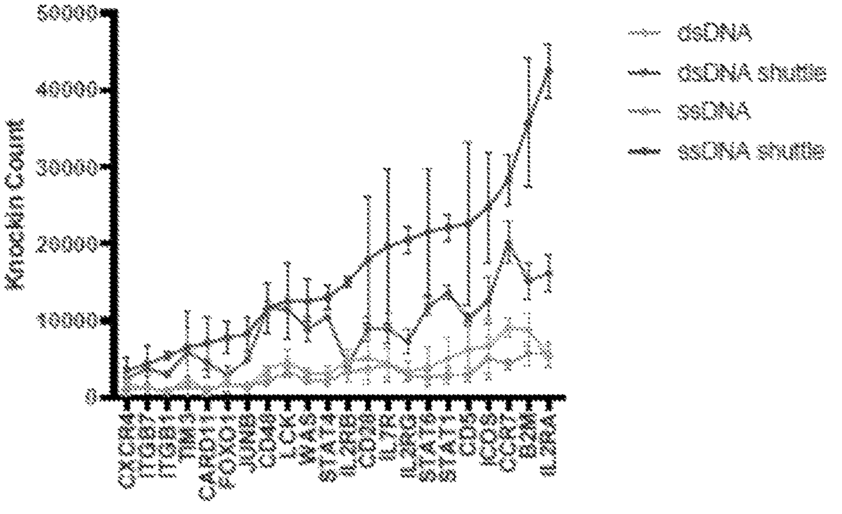

FIGS. 10A-10C show that 22 target sites were tested for a surface marker knock-in using ssDNA shuttle technology.

FIGS. 11A-11M show that ssDNA shuttle technology can be used in many different primary human cell types.

Figure 12A:
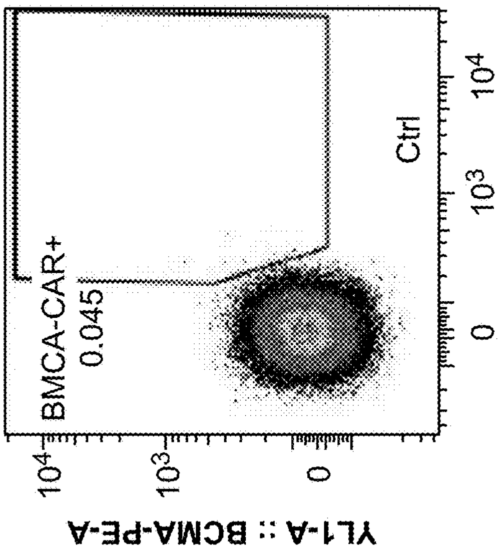
Figure 12B:
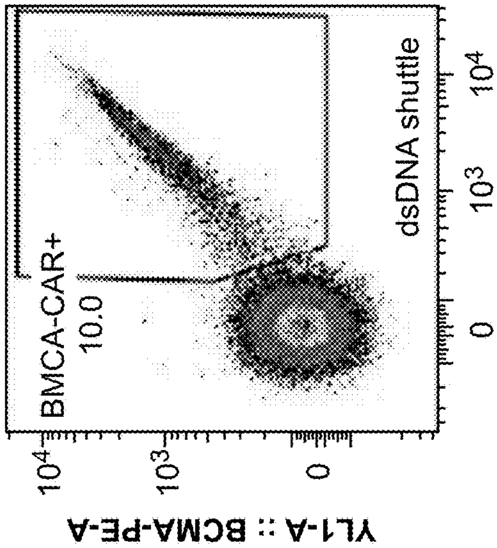
Figure 12C:
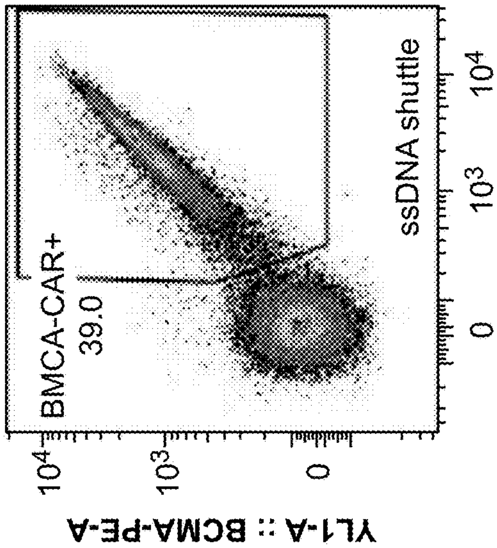

FIGS. 12A-12C show flow plots demonstrating knock-in populations of CAR and TCR constructs into the TRAC genomic locus in primary human T cells.

Figure 12D:
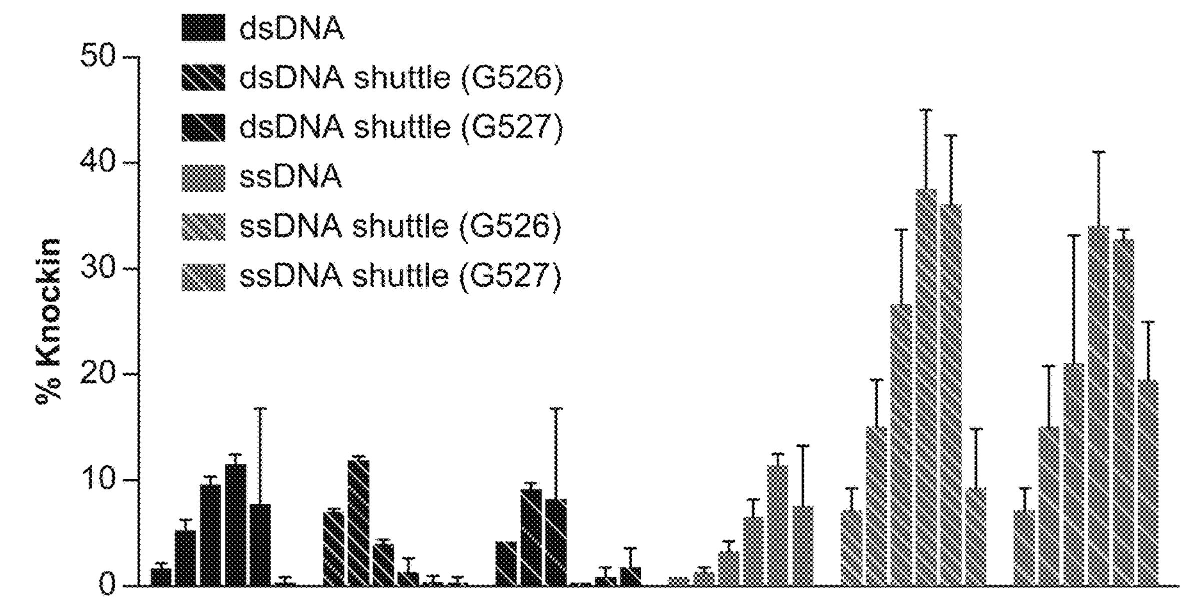
Figure 12E:
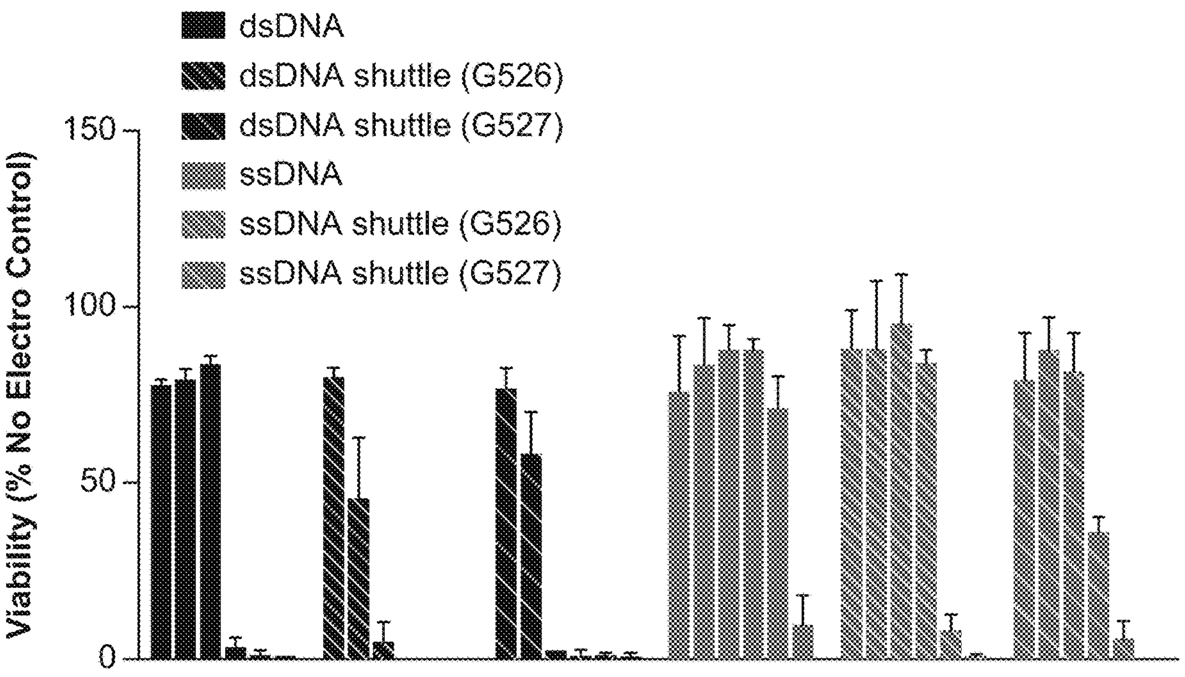

FIGS. 12D and 12E show knock-in efficiencies and viabilities of ssDNA shuttle constructs with two different gRNA target sequences.

Figure 12F:
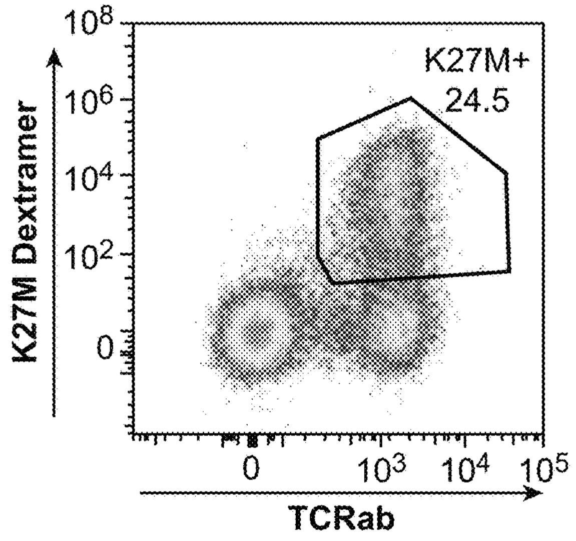
Figure 12G:
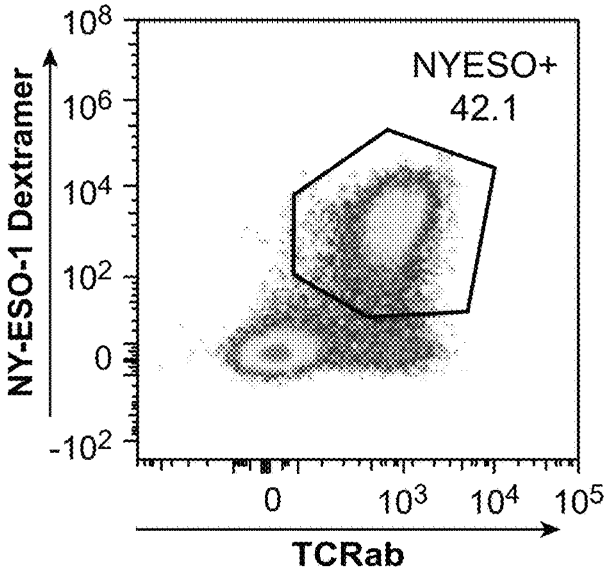
Figure 12H:
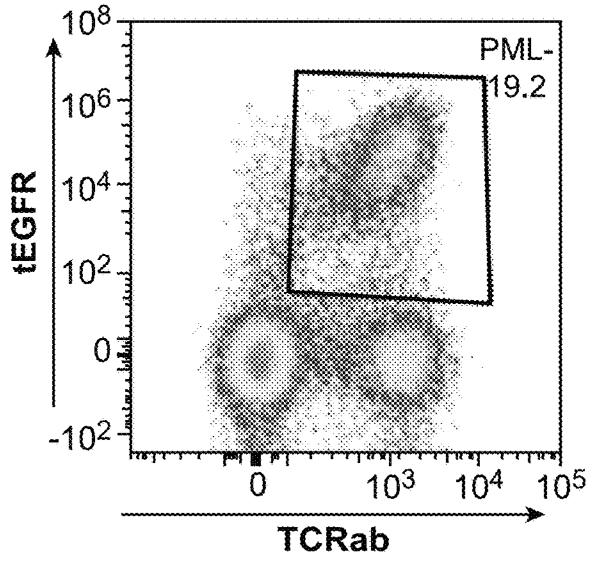

FIGS. 12F-12H show flow plots demonstrating knock-in rates with three different TCR knock-in ssDNA shuttle constructs using G526 gRNA sequence.

DETAILED DESCRIPTION OF THE DISCLOSURE

The following description recites various aspects and embodiments of the present compositions and methods. No particular embodiment is intended to define the scope of the compositions and methods. Rather, the embodiments merely provide non-limiting examples of various compositions and methods that are at least included within the scope of the disclosed compositions and methods. The description is to be read from the perspective of one of ordinary skill in the art; therefore, information well known to the skilled artisan is not necessarily included.

I. Introduction

Virus-modified T cells are approved for cancer immunotherapy, but more versatile and precise genome modifications are needed for a wider range of adoptive cellular therapies (Yin et al., *Nat Rev Clin Oncol,* 16(5):281-295, 2019; Dunbar et al., *Science* 359:6372, 2018; Cornu et al., *Nat Med* 23:415-423, 2017; and David and Doherty, *Toxicol Sci* 155:315-325, 2017). The CRISPR (Clustered Regularly Interspaced Short Palindromic Repeats)-Cas (CRISPR-associated protein) nuclease system is an engineered nuclease system based on a bacterial system that can be used for genome engineering. It is based on part of the adaptive immune response of many bacteria and archaea. When a virus or plasmid invades a bacterium, segments of the invader's DNA are converted into CRISPR RNAs (crRNA) by the "immune" response. The crRNA then associates, through a region of partial complementarity, with another type of RNA called tracrRNA to guide the Cas (e.g., Cas9) nuclease to a region homologous to the crRNA in the target DNA called a "protospacer." The Cas (e.g., Cas9) nuclease cleaves the DNA to generate blunt ends at the double-strand break at sites specified by a 20-nucleotide guide sequence contained within the crRNA transcript. The Cas (e.g., Cas9) nuclease can require both the crRNA and the tracrRNA for site-specific DNA recognition and cleavage. This system has now been engineered such that the crRNA and tracrRNA can be combined into one molecule (the "single-guide RNA" or "sgRNA"), and the crRNA equivalent portion of the sgRNA can be engineered to guide the Cas (e.g., Cas9) nuclease to target any desired sequence (see, e.g., Jinek et al. (2012) *Science* 337:816-821; Jinek et al. (2013) *eLife* 2:e00471; Segal (2013) *eLife* 2:e00563). Thus, the CRISPR-Cas system can be engineered to create a double-strand break at a desired target in a genome of a cell, and harness the cell's endogenous mechanisms to repair the induced break by, e.g., homology-directed repair (HDR).

Figure 1:
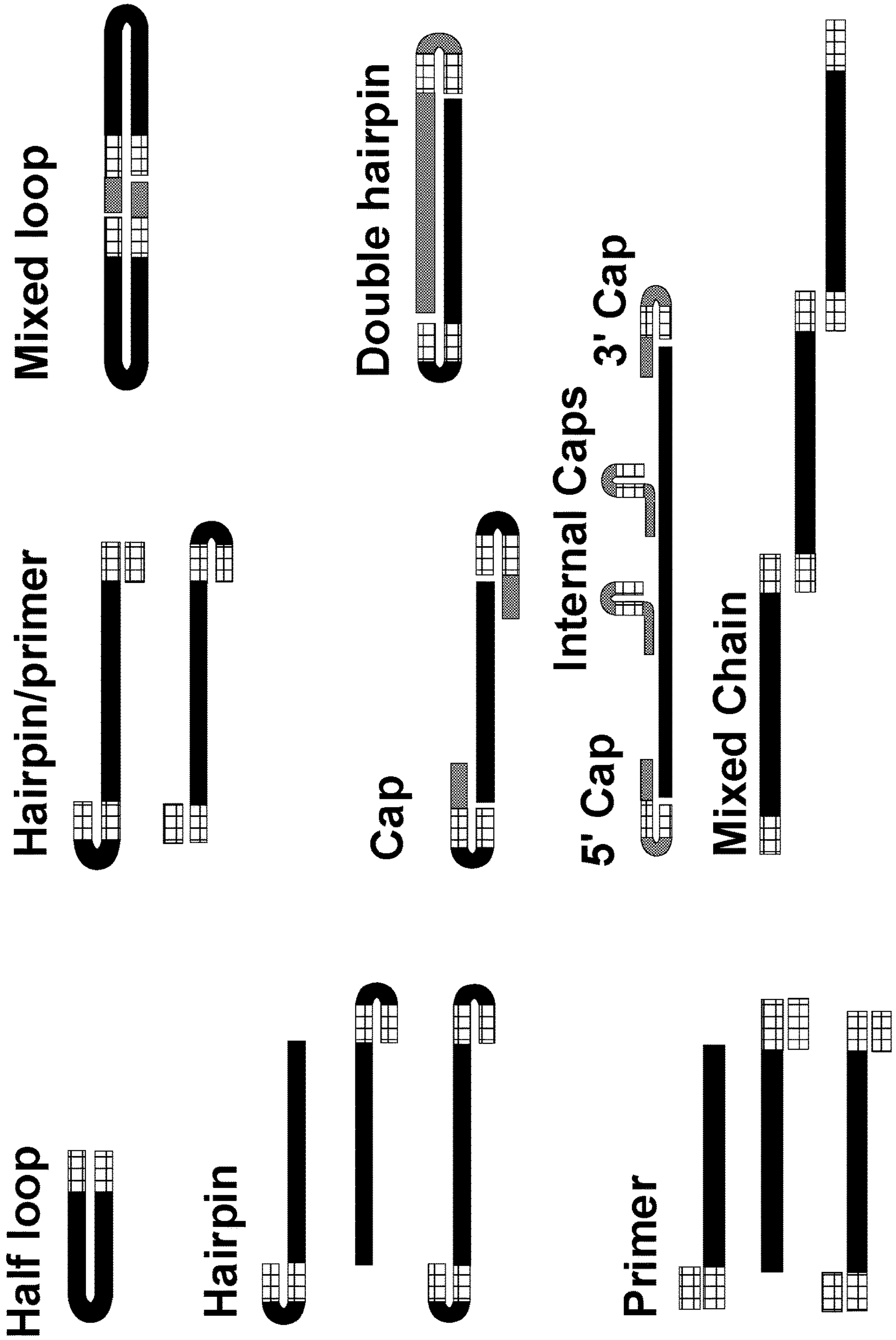
FIG. 1 shows schematic illustrations of various forms of donor constructs. The plaid regions indicate the DNA-binding protein target sequences. The regions where two plaid regions overlap indicate the double-stranded duplex form from the hybridization of two complementary DNA-binding protein target sequences. The black and grey regions are single-stranded. The regions where a black region overlaps with a grey region indicate that these two regions hybridize. The mixed loop is the only case containing a region where two grey regions overlap—these two grey regions hybridize to each other.

The HDRT can be composed of either double-stranded DNA (dsDNA) or single-stranded DNA (ssDNA). In some embodiments, ssDNA HDRT (ssHDRT) can have reduced toxicity and reduced off-target integration as compared to dsDNA HDRT. However, dsDNA can be easier to produce and can sometimes provide a higher knock-in efficiency. As described herein, one or more DNA-binding protein target sequences, when added at the ends of the HDRT, can interact with DNA-binding proteins to improve trafficking of the HDRT into the cell and "shuttle" the HDRT to the desired cellular location (e.g., a cellular location in proximity to the target nucleic acid (e.g., the nucleus)) following electroporation and enhance target nucleic acid modification efficiency. The higher cellular concentration of HDRT can result in a higher knock-in efficiency. The current disclosure provides ssHDRTs with one or more DNA-binding protein target sequences at the termini of the HDRT, in which one or more DNA-binding protein target sequence forms a double-stranded duplex with a complementary polynucleotide sequence. As shown in FIG. 1 and described further herein, the DNA-binding protein target sequence can be fused to or separate from the HDRT. Without being bound by any theory, the sequences containing the ssHDRT and DNA-binding protein target sequences described herein provide both the benefits of an ssDNA HDRT, such as reduced toxicity and reduced off-target integration, and the benefits of a dsDNA HDRT, such as the easy of production and a higher knock-in efficiency.

The compositions and methods described herein may be used for genetic modifications that improve cell viability, achieve therapeutically-relevant large transgene insertion levels, and minimize dependence upon foreign DNA, thus reducing potential for off-target genotoxicity. The disclosure provides a strategy for improving Cas protein and sgRNA RNP complex editing outcomes that in conjunction improve cellular gene editing, for example primary human T cell editing and cell survival and enable high efficiency large transgene knock-in in both iPS-derived and primary human hematopoietic stem cells.

II. Donor Constructs

The disclosure provides donor constructs for modifying a target nucleic acid that include at least one donor template comprising a single-stranded homology directed repair template (ssHDRT) and one or more DNA-binding protein target sequences, wherein at least one DNA-binding protein target sequence forms a double-stranded duplex with a complementary polynucleotide sequence. In some embodiments, the donor construct can be formed from a single polynucleotide molecule. In other embodiments, the donor construct can be formed from two or more polynucleotide molecules. Various forms of the donor construct are described in detail herein.

Primer Donor Construct

One form of the donor construct is the "primer" donor construct as shown in FIG. 1. In general, the primer donor construct has a donor template that is a linear template and either one or two double-stranded duplex regions formed from two complementary DNA-binding protein target sequences. The primer donor construct can contain a first polynucleotide comprising a single donor template, and at least one second polynucleotide comprising a complementary polynucleotide sequence, wherein the donor template is a linear template. In some embodiments, the donor template contains one ssHDRT and one DNA-binding protein target sequence (e.g., first two types of primer donor construct as shown in FIG. 1). In other embodiments, the donor template contains one ssHDRT and two DNA-binding protein target sequences (e.g., the third type of primer donor construct as shown in FIG. 1). Each DNA-binding protein target sequence forms a double-stranded duplex with a complementary polynucleotide sequence that does not extend into the ssHDRT sequence. In some embodiments, the donor template can contain two polynucleotide molecules, in which one polynucleotide molecule contains a donor template that has one ssHDRT and one DNA-binding protein target sequence and the second polynucleotide molecule contains a complementary polynucleotide sequence. In other embodiments, the donor template can contain three polynucleotide molecules, in which the first polynucleotide molecule contains a donor template that has one ssHDRT and one DNA-binding protein target sequence and each of the second and third polynucleotide molecules contains a complementary polynucleotide sequence.

The DNA-binding protein target sequence can be located at or proximal to the 5' and/or 3' terminus of the donor template.

Some exemplary sequences of the donor template in the primer donor construct (e.g., the third type of primer donor construct as shown in FIG. 1) are shown in SEQ ID NOS:1-4. In each of the sequences of SEQ ID NOS:1-4, the first DNA-binding protein target sequence is in bold, and the second DNA-binding protein target sequence is underlined. For example, as can be seen in the sequence of SEQ ID NO:1, one DNA-binding protein target sequence can be located at the 5' terminus of the 5' homology arm of the ssHDRT (bold in SEQ ID NO:1), while another DNA-binding protein target sequence that is the reverse complement of the first DNA-binding protein target sequence can be located at the 3' terminus of the 3' homology arm of the ssHDRT (underlined in SEQ ID NO:1). Regions of nucleotides, e.g., a region of between 3 and 10 (e.g., 3, 4, 5, 6, 7, 8, 9, or 10) nucleotides that can be random or otherwise can be placed 5' to the first DNA-binding protein target sequence and 3' to the second DNA-binding protein target sequence in order to facilitate the binding of the DNA-binding protein.

Mixed Chain Donor Construct

Another form of the donor construct is the "mixed chain" donor construct as shown in FIG. 1. The mixed-chain donor construct can contain multiple donor templates (e.g., two, three, four, or five donor templates), in which each donor template contains at least one DNA DNA-binding protein target sequence. In this example of the mixed-chain donor construct, the DNA-binding protein target sequence of one donor template can hybridize to the DNA-binding protein target sequence of another donor template (i.e., one DNA-binding protein target sequence can serve as the complementary polynucleotide sequence of the other DNA-binding protein target sequence), in order to bring the multiple donor templates in the mixed-chain donor construct together by way of hydrogen bonding between the DNA-binding protein target sequences in different donor templates. Further, the multiple donor templates can have the same ssHDRT sequence or different ssHDRT sequences.

For example, the mixed chain donor construct can contain (a) a first donor template comprising a first DNA-binding protein target sequence located at or proximal to the 3' terminus of the first donor template, and (b) a second donor template comprising a second DNA-binding protein target sequence located at or proximal to the 3' terminus of the second donor template, in which the first DNA-binding protein target sequence hybridizes to the second DNA-binding protein target sequence. Further, in order to bring a third donor template into the mixed chain donor construct, the second donor template can further contain a third DNA-binding protein target sequence that is located at or proximal to the 5' terminus of the second donor template, and the third donor template can contain a fourth DNA-binding protein target sequence located at or proximal to the 5' terminus of the third template. In this manner, the third DNA-binding protein target sequence in the second donor template can hybridize to the fourth DNA-binding protein target sequence in the third donor template, such that all three donor templates are brought together by way of hydrogen bonding between DNA-binding protein target sequences. See, e.g., "mixed chain" in FIG. 1.

Following the same approach, additional donor templates can be added to the mixed chain donor construct, as long as the additional donor templates contain DNA-binding protein target sequences that are complementary and can hybridize to the DNA-binding protein target sequences in the adjacent donor templates.

Some exemplary sequences of the donor templates in the mixed chain donor construct are shown in SEQ ID NOS:5 and 6. This exemplary donor construct contains a first donor template having the sequence of SEQ ID NO:5 and a second donor template having the sequence of SEQ ID NO:6, in which the first donor template contains a first DNA-binding protein target sequence (bold in SEQ ID NO:5) and a second DNA-binding protein target sequence (underlined in SEQ ID NO:5), and the second donor template contains a third DNA-binding protein target sequence (bold in SEQ ID NO:6) and a fourth DNA-binding protein target sequence (underlined in SEQ ID NO:6). The fourth DNA-binding protein target sequence hybridizes to the second DNA-binding protein target sequence to bring the two DNA templates together to form the mixed chain donor construct. Regions of random nucleotides can be placed 5' to the first or the third DNA-binding protein target sequence and 3' to the second or fourth DNA-binding protein target sequence in order to facilitate the binding of the DNA-binding protein.

Half Loop Donor Construct

Another form of the donor construct is the "half loop" donor construct as shown in FIG. 1. The half loop donor construct can contain one donor template that has two DNA-binding protein target sequences each located at or proximal to a terminus of the donor template. The two DNA-binding protein target sequences can hybridize to each other and introduce a hairpin into the half loop donor construct. A hairpin is formed when two polynucleotide regions within the same polynucleotide strand hybridize to form a double helix or a double-stranded duplex that ends in an unpaired loop. In some embodiments, the unpaired loop in the hairpin has between 4 and 200 (e.g., between 4 and 180, between 4 and 160, between 4 and 140, between 4 and 120, between 4 and 100, between 4 and 80, between 4 and 60, between 4 and 40, between 4 and 20, between 4 and 10, between 4 and 8, between 8 and 200, between 10 and 200, between 20 and 200, between 40 and 200, between 60 and 200, between 80 and 200, between 100 and 200, between 120 and 200, between 140 and 200, between 160 and 200, or between 180 and 200) nucleotides. In some embodiments, each of the two polynucleotide regions that hybridize in a hairpin is between 10 and 50 (e.g., between 10 and 45, between 10 and 40, between 10 and 35, between 10 and 30, between 10 and 25, between 10 and 20, between 10 and 15, between 15 and 50, between 20 and 50, between 25 and 50, between 30 and 50, between 35 and 50, between 40 and 50, or between 45 and 50) nucleotides.

As shown in FIG. 1, the two DNA-binding protein target sequences in the half loop donor construct hybridize to each other to form the double helix, while the ssHDRT forms the unpaired loop.

An sequence of the donor template in the half loop donor construct is shown in SEQ ID NO:7. As can be seen in the sequence of SEQ ID NO:7, a first DNA-binding protein target sequence is located at the 5' terminus of the 5' homology arm of the ssHDRT (bold in SEQ ID NO:7), and a second DNA-binding protein target sequence is located at the 3' terminus of the 3' homology arm of the ssHDRT (underlined in SEQ ID NO:7). Regions of random nucleotides can be placed 5' to the first DNA-binding protein target sequence and 3' to the second DNA-binding protein target sequence in order to facilitate the binding of the DNA-binding protein.

Hairpin Donor Construct

Another form of the donor construct is the "hairpin" donor construct as shown in FIG. 1. In a hairpin donor construct, a hairpin is at one or both ends of the construct, in which the double-stranded region of the hairpin is formed from two complementary DNA-binding protein target sequences. In some embodiments, the hairpin donor construct can contain one hairpin. For example, the hairpin donor construct can contain one donor template that has two DNA-binding protein target sequences, in which one DNA-binding protein target sequence is located at or proximal to the 5' or 3' terminus of the donor template, while another DNA-binding protein target sequence is located within the donor template (e.g., first two types of hairpin donor construct as shown in FIG. 1). In certain embodiments, a first DNA-binding protein target sequence is located at or proximal to the 5' terminus of the donor template, while a second DNA-binding protein target sequence is located downstream (e.g., between 3 and 10, between 3 and 9, between 3 and 8, between 3 and 7, between 3 and 6, or between 3 and 5 nucleotides) from the first DNA-binding protein target sequence and within the donor template (e.g., first type of hairpin donor construct as shown in FIG. 1). In certain embodiments, a first DNA-binding protein target sequence is located at or proximal to the 3' terminus of the donor template, while a second DNA-binding protein target sequence is located upstream (e.g., between 3 and 10, between 3 and 9, between 3 and 8, between 3 and 7, between 3 and 6, or between 3 and 5 nucleotides) from the first DNA-binding protein target sequence and within the donor template (e.g., second type of hairpin donor construct as shown in FIG. 1).

A hairpin is formed when two polynucleotide regions within the same polynucleotide strand hybridize to form a double helix or a double-stranded duplex that ends in an unpaired loop. In some embodiments, the unpaired loop in the hairpin has between 4 and 200 (e.g., between 4 and 180, between 4 and 160, between 4 and 140, between 4 and 120, between 4 and 100, between 4 and 80, between 4 and 60, between 4 and 40, between 4 and 20, between 4 and 10, between 4 and 8, between 8 and 200, between 10 and 200, between 20 and 200, between 40 and 200, between 60 and 200, between 80 and 200, between 100 and 200, between 120 and 200, between 140 and 200, between 160 and 200, or between 180 and 200) nucleotides. In some embodiments, each of the two polynucleotide regions that hybridize in a hairpin is between 10 and 50 (e.g., between 10 and 45, between 10 and 40, between 10 and 35, between 10 and 30, between 10 and 25, between 10 and 20, between 10 and 15, between 15 and 50, between 20 and 50, between 25 and 50, between 30 and 50, between 35 and 50, between 40 and 50, or between 45 and 50) nucleotides.

In some embodiments, the hairpin donor construct can contain two hairpins (e.g., third type of hairpin donor construct as shown in FIG. 1). For example, the hairpin donor construct can contain one donor template that has four DNA-binding protein target sequences, in which two DNA-binding protein target sequences are each located at or proximal to the 5' or 3' terminus of the donor template, while two DNA-binding protein target sequences are located within the donor template (e.g., third type of hairpin donor construct as shown in FIG. 1). In certain embodiments, the donor construct can contain a single donor template, and the donor template can contain two hairpins, a first DNA-binding protein target sequence located at or proximal to the 5' terminus of the donor template, a second DNA-binding protein target sequence that is located downstream (e.g., between 3 and 10, between 3 and 9, between 3 and 8, between 3 and 7, between 3 and 6, or between 3 and 5 nucleotides) from the first DNA-binding protein and can serve as a complementary polynucleotide sequence to the first DNA-binding protein target sequence, a third DNA-binding protein target sequence located at or proximal to the 3' terminus of the donor template, and a fourth DNA-binding protein target sequence that is located upstream (e.g., between 3 and 10, between 3 and 9, between 3 and 8, between 3 and 7, between 3 and 6, or between 3 and 5 nucleotides) from the third DNA-binding protein and can serve as a complementary polynucleotide sequence to the third DNA-binding protein target sequence. Thus, the first DNA-binding protein target sequence hybridizes to the second DNA-binding protein target sequence to form a first hairpin at or proximal to the 5' terminus of the donor template, and the third DNA-binding protein target sequence hybridizes to the fourth DNA-binding protein target sequence to form a second hairpin at or proximal to the 3' terminus of the donor template. (e.g., third type of hairpin donor construct as shown in FIG. 1).

An exemplary sequence of the donor template in the first type of hairpin donor construct as shown in FIG. 1 is shown in SEQ ID NO:8. As can be seen in the sequence of SEQ ID NO:8, a first DNA-binding protein target sequence is located proximal to the 5' terminus of the donor template (bold in SEQ ID NO:8) and a second DNA-binding protein target sequence is located downstream from the first DNA-binding protein target sequence (underlined in SEQ ID NO:8). An exemplary sequence of the donor template in the second type of hairpin donor construct as shown in FIG. 1 is shown in SEQ ID NO:9. As can be seen in the sequence of SEQ ID NO:9, a first DNA-binding protein target sequence is located proximal to the 3' terminus of the donor template (bold in SEQ ID NO:9) and a second DNA-binding protein target sequence is located upstream from the first DNA-binding protein target sequence (underlined in SEQ ID NO:9).

Hairpin/Primer Donor Construct

Another form of the donor construct is the “hairpin/primer” donor construct as shown in FIG. 1. The hairpin/primer donor construct can contain two polynucleotide molecules. A first polynucleotide can contain a donor template that has an ssHDRT, a first DNA-binding protein target sequence, a second DNA-binding protein target sequence, and a third DNA-binding protein target sequence. The first DNA-binding protein target sequence can be located at or proximal to the 5' terminus of the donor template; the second DNA-binding protein target sequence can be located downstream (e.g., between 3 and 10, between 3 and 9, between 3 and 8, between 3 and 7, between 3 and 6, or between 3 and 5 nucleotides) from the first DNA-binding protein target sequence to form a hairpin with the first DNA-binding protein target sequence; and the third DNA-binding protein target sequence can be located at or proximal to the 3' terminus of the donor template (e.g., first type of hairpin/primer donor construct as shown in FIG. 1). The first and second DNA-binding protein target sequences can hybridize to each other to form a hairpin in the donor template. The hairpin/primer donor construct can contain a second polynucleotide having a fourth DNA-binding protein target sequence, in which the fourth DNA-binding protein target sequence can hybridize to the third DNA-binding protein target sequence in the first polynucleotide in the donor construct. In other embodiments of the hairpin/primer donor construct, the first polynucleotide in the donor construct can contain a first DNA-binding protein target sequence located at or proximal to the 3' terminus of the donor template, a second DNA-binding protein target sequence located upstream (e.g., between 3 and 10, between 3 and 9, between 3 and 8, between 3 and 7, between 3 and 6, or between 3 and 5 nucleotides) from the first DNA-binding protein target sequence, and a third DNA-binding protein target sequence located at or proximal to the 5' terminus of the donor template (e.g., second type of hairpin/primer donor construct as shown in FIG. 1).

A hairpin is formed when two polynucleotide regions within the same polynucleotide strand hybridize to form a double helix or a double-stranded duplex that ends in an unpaired loop. In some embodiments, the unpaired loop in the hairpin has between 4 and 200 (e.g., between 4 and 180, between 4 and 160, between 4 and 140, between 4 and 120, between 4 and 100, between 4 and 80, between 4 and 60, between 4 and 40, between 4 and 20, between 4 and 10, between 4 and 8, between 8 and 200, between 10 and 200, between 20 and 200, between 40 and 200, between 60 and 200, between 80 and 200, between 100 and 200, between 120 and 200, between 140 and 200, between 160 and 200, or between 180 and 200) nucleotides. In some embodiments, each of the two polynucleotide regions that hybridize in a hairpin is between 10 and 50 (e.g., between 10 and 45, between 10 and 40, between 10 and 35, between 10 and 30, between 10 and 25, between 10 and 20, between 10 and 15, between 15 and 50, between 20 and 50, between 25 and 50, between 30 and 50, between 35 and 50, between 40 and 50, or between 45 and 50) nucleotides.

Some exemplary sequences of the donor template in the hairpin/primer donor construct are shown in SEQ ID NOS: 10 and 11. As can be seen in the sequence of SEQ ID NO:10, a first DNA-binding protein target sequence is located proximal to the 5' terminus of the donor template (bold in SEQ ID NO:10), a second DNA-binding protein target sequence is located downstream from the first DNA-binding protein target sequence (underlined in SEQ ID NO:10), and a third DNA-binding protein target sequence is located proximal to the 3' terminus of the donor template (bold and underlined in SEQ ID NO:10). Regions of random nucleotides can be placed 5' to the first DNA-binding protein target sequence and 3' to the third DNA-binding protein target sequence in order to facilitate the binding of the DNA-binding protein.

In another example, as can be seen in the sequence of SEQ ID NO:11, a first DNA-binding protein target sequence is located proximal to the 5' terminus of the donor template (bold in SEQ ID NO:11), a second DNA-binding protein target sequence is located proximal to the 3' terminus of the donor template (underlined in SEQ ID NO:11), and a third DNA-binding protein target sequence is located upstream from the second DNA-binding protein target sequence (bold and underlined in SEQ ID NO:11). Regions of random nucleotides can be placed 5' to the first DNA-binding protein target sequence and 3' to the second DNA-binding protein target sequence in order to facilitate the binding of the DNA-binding protein.

Mixed Loop Donor Construct

Another form of the donor construct is the “mixed loop” donor construct as shown in FIG. 1. The mixed loop donor construct contains two donor templates that are hybridized to each other via a sequence at a terminus of each of the donor templates. In some embodiments, each of the two donor templates in the mixed loop donor construct has a hairpin. The mixed loop donor construct can contain a first donor template having a first ssHDRT, a first DNA-binding protein target sequence, and a second DNA-binding protein target sequence, and a second donor template having a second ssHDRT, a third DNA-binding protein target sequence, and a fourth DNA-binding protein target sequence. The first and second DNA-binding protein target sequences can hybridize to each other, thus, causing the first donor template to form a hairpin. The third and fourth DNA-binding protein target sequences can hybridize to each other, thus, causing the second donor template to form a hairpin. In some embodiments, the first donor template contains a hybridization sequence at its 5' terminus and the second donor template contains a complementary hybridization sequence at its 5' terminus, such that the two hybridization sequences can hybridize to each other to bring the first and second donor templates together to form the mixed loop donor construct. In other embodiments, the first donor template contains a hybridization sequence at its 3' terminus and the second donor template contains a complementary hybridization sequence at its 3' terminus, such that the two hybridization sequences can hybridize to each other to bring the first and second donor templates together to form the mixed loop donor construct. Further, the first ssHDRT and the second ssHDRT in their respectively donor template can have the same sequence or different sequences. The terminal sequence in each of the donor template can have between 4 and 30 (e.g., between 4 and 28, between 4 and 26, between 4 and 24, between 4 and 22, between 4 and 20, between 4 and 18, between 4 and 16, between 4 and 14, between 4 and 12, between 4 and 10, between 4 and 8, between 4 and 6, between 6 and 30, between 8 and 30, between 10 and 30, between 12 and 30, between 14 and 30, between 16 and 30, between 18 and 30, between 20 and 30, between 22 and 30, between 24 and 30, between 26 and 30, or between 28 and 30) nucleotides.

A hairpin is formed when two polynucleotide regions within the same polynucleotide strand hybridize to form a double helix or a double-stranded duplex that ends in an unpaired loop. In some embodiments, the unpaired loop in the hairpin has between 4 and 200 (e.g., between 4 and 180, between 4 and 160, between 4 and 140, between 4 and 120, between 4 and 100, between 4 and 80, between 4 and 60, between 4 and 40, between 4 and 20, between 4 and 10, between 4 and 8, between 8 and 200, between 10 and 200, between 20 and 200, between 40 and 200, between 60 and 200, between 80 and 200, between 100 and 200, between 120 and 200, between 140 and 200, between 160 and 200, or between 180 and 200) nucleotides. In some embodiments, each of the two polynucleotide regions that hybridize in a hairpin is between 10 and 50 (e.g., between 10 and 45, between 10 and 40, between 10 and 35, between 10 and 30, between 10 and 25, between 10 and 20, between 10 and 15, between 15 and 50, between 20 and 50, between 25 and 50, between 30 and 50, between 35 and 50, between 40 and 50, or between 45 and 50) nucleotides.

Some exemplary sequences of the donor template in the mixed loop donor construct are shown in SEQ ID NOS:12 and 13. The double-underlined portion in the sequence of SEQ ID NO:12 can hybridize to the double-underlined portion in the sequence of SEQ ID NO:13 to bring the two donor templates together to form the mixed loop donor construct. Further, the first donor template contains a first DNA-binding protein target sequence (bold in SEQ ID NO:12) and a second DNA-binding protein target sequence (underlined in SEQ ID NO:12), in which the first and second DNA-binding protein target sequences hybridize to each other to form a hairpin in the first donor template. The second donor template contains a third DNA-binding protein target sequence (bold in SEQ ID NO:13) and a fourth DNA-binding protein target sequence (underlined in SEQ ID NO:13), in which the third and fourth DNA-binding protein target sequences hybridize to each other to form a hairpin in the second donor template.

In another example, a mixed loop donor construct contains the sequences of SEQ ID NOS:14 and 15. The first donor template (SEQ ID NO:14) has a DNA-binding protein target sequence (bold in SEQ ID NO:14) and the second donor template (SEQ ID NO:15) has a DNA-binding protein target sequence (bold in SEQ ID NO:15). The double-underlined portion in SEQ ID NO:14 hybridizes to the double-underlined portion in SEQ ID NO:15 to bring the two donor templates together to form the mixed loop donor construct.

Cap Donor Construct

Another form of the donor construct is the "cap" donor construct as shown in FIG. 1.

The cap donor construct contains one donor template that is formed from two or more polynucleotide molecules. In some embodiments, the cap donor construct contains one donor template that is formed from two polynucleotide molecules. For example, the cap donor construct can contain a first polynucleotide having the ssHDRT, and a second polynucleotide having a first DNA-binding protein target sequence, a second DNA-binding protein target sequence, and a 5' terminal sequence. The first and second DNA-binding protein target sequences can hybridize to each other to form a hairpin in the second polynucleotide of the donor construct. Further, the 5' terminal sequence in the second polynucleotide can hybridize to a sequence at the 5' terminus of the first polynucleotide.

In another example, The cap donor construct can contain a first polynucleotide having the ssHDRT, a second polynucleotide having a first DNA-binding protein target sequence, a second DNA-binding protein target sequence, and a 5' terminal sequence, a third polynucleotide having a third DNA-binding protein target sequence, a fourth DNA-binding protein target sequence, and a 3' terminal sequence. The first and second DNA-binding protein target sequences can hybridize to each other to form a hairpin in the second polynucleotide of the donor construct. The third and fourth DNA-binding protein target sequences can hybridize to each other to form a hairpin in the third polynucleotide of the donor construct. Further, the 5' terminal sequence in the second polynucleotide can hybridize to a sequence at the 5' terminus of the first polynucleotide, and the 3' terminal sequence in the third polynucleotide can hybridize to a sequence at the 3' terminus of the first polynucleotide to form the cap donor construct (see, e.g., FIG. 1). Further, the cap donor construct can contain polynucleotide molecules that hybridize to an internal sequence of the ssHDRT (see, e.g., internal cap in FIG. 1). The internal cap donor construct can contain a first polynucleotide having the ssHDRT, a second polynucleotide having a first DNA-binding protein target sequence, a second DNA-binding protein target sequence, and a first internal sequence, a third polynucleotide having a third DNA-binding protein target sequence, a fourth DNA-binding protein target sequence, and a second internal sequence. The first internal sequence in the second polynucleotide can hybridize to a sequence in the ssHDRT of the first polynucleotide, and the second internal sequence in the third polynucleotide can hybridize to a sequence in the ssHDRT of the first polynucleotide to form the internal cap donor construct (see, e.g., FIG. 1).

A hairpin is formed when two polynucleotide regions within the same polynucleotide strand hybridize to form a double helix or a double-stranded duplex that ends in an unpaired loop. In some embodiments, the unpaired loop in the hairpin has between 4 and 200 (e.g., between 4 and 180, between 4 and 160, between 4 and 140, between 4 and 120, between 4 and 100, between 4 and 80, between 4 and 60, between 4 and 40, between 4 and 20, between 4 and 10, between 4 and 8, between 8 and 200, between 10 and 200, between 20 and 200, between 40 and 200, between 60 and 200, between 80 and 200, between 100 and 200, between 120 and 200, between 140 and 200, between 160 and 200, or between 180 and 200) nucleotides. In some embodiments, each of the two polynucleotide regions that hybridize in a hairpin is between 10 and 50 (e.g., between 10 and 45, between 10 and 40, between 10 and 35, between 10 and 30, between 10 and 25, between 10 and 20, between 10 and 15, between 15 and 50, between 20 and 50, between 25 and 50, between 30 and 50, between 35 and 50, between 40 and 50, or between 45 and 50) nucleotides.

In other embodiments of the cap donor construct, the construct can be formed from two polynucleotides. For example, a first polynucleotide having the ssHDRT, and a second polynucleotide having a first DNA-binding protein target sequence, a second DNA-binding protein target sequence, and a 5' terminal sequence, in which the first and second DNA-binding protein target sequences can hybridize to each other to form a hairpin in the second polynucleotide, and the 5' terminal sequence can hybridize to a sequence at the 5' terminus of the first polynucleotide. In yet other embodiments, instead of a 5' terminal sequence, the second polynucleotide can have a sequence at the 3' terminus that can hybridize to a sequence at the 3' terminus of the first polynucleotide.

Some exemplary sequences of the donor template in the cap donor construct are shown in SEQ ID NOS:18-20, which form the first, second, and third polynucleotides in the cap donor construct, respectively. The cap donor construct contains a first polynucleotide having an ssHDRT (SEQ ID NO:18), a second polynucleotide having a first DNA-binding protein target sequence (bold in SEQ ID NO:19), a second DNA-binding protein target sequence (underlined in SEQ ID NO:19), and a 5' terminal sequence (double-underlined in SEQ ID NO:19), a third polynucleotide having a third DNA-binding protein target sequence (bold in SEQ ID NO:20), a fourth DNA-binding protein target sequence (underlined in SEQ ID NO:20), and a 3' terminal sequence (double-underlined in SEQ ID NO:20). Further, the 5' terminal sequence in the second polynucleotide (double-underlined in SEQ ID NO:19) can hybridize to a sequence at the 5' terminus of the first polynucleotide (double-underlined in SEQ ID NO:18), and the 3' terminal sequence in the third polynucleotide (double-underlined in SEQ ID NO:20) can hybridize to a sequence at the 3' terminus of the first polynucleotide (double-underlined in SEQ ID NO:18) to form the cap donor construct (see, e.g., FIG. 1).

In another example, some exemplary sequences of the donor template in the internal cap donor construct are shown in SEQ ID NOS:21-24, which form the first, second, third, and fourth polynucleotides in the internal cap donor construct, respectively. The internal cap donor construct contains a first polynucleotide having an ssHDRT (SEQ ID NO:21), a second polynucleotide having a first DNA-binding protein target sequence (bold in SEQ ID NO:22), a second DNA-binding protein target sequence (underlined in SEQ ID NO:22), and a first internal sequence (double-underlined in SEQ ID NO:22), a third polynucleotide having a third DNA-binding protein target sequence (bold in SEQ ID NO:23), a fourth DNA-binding protein target sequence (underlined in SEQ ID NO:23), and a second internal sequence (double-underlined in SEQ ID NO:23), and a fourth polynucleotide having a fifth DNA-binding protein target sequence (bold in SEQ ID NO:24), a sixth DNA-binding protein target sequence (underlined in SEQ ID NO:24), and a third internal sequence (double-underlined in SEQ ID NO:24). Further, the first internal sequence in the second polynucleotide (double-underlined in SEQ ID NO:22) can hybridize to a sequence within the first polynucleotide (bold in SEQ ID NO:21), the second internal sequence in the third polynucleotide (double-underlined in SEQ ID NO:23) can hybridize to a sequence within the first polynucleotide (underlined in SEQ ID NO:21), and the third internal sequence in the fourth polynucleotide (double-underlined in SEQ ID NO:24) can hybridize to a sequence within the first polynucleotide (double-underlined in SEQ ID NO:21) to form the internal cap donor construct (see, e.g., FIG. 1).

Double Hairpin Donor Construct

Another form of the donor construct is the "double hairpin" donor construct as shown in FIG. 1. The double hairpin donor construct contains two donor templates that are hybridized to each other via the ssHDRT regions in the donor templates. For example, the first donor template can have an ssHDRT, a first DNA-binding protein target sequence located at or proximal to the 5' terminus of the first donor template, and a second DNA-binding protein target sequence located downstream (e.g., between 3 and 10, between 3 and 9, between 3 and 8, between 3 and 7, between 3 and 6, or between 3 and 5 nucleotides) from the first DNA-binding protein target sequence, in which the first and second DNA-binding protein target sequences can hybridize to each other to form a hairpin in the first donor template. The second donor template can have an ssHDRT, a third DNA-binding protein target sequence located at or proximal to the 5' terminus of the second donor template, and a fourth DNA-binding protein target sequence located downstream (e.g., between 3 and 10, between 3 and 9, between 3 and 8, between 3 and 7, between 3 and 6, or between 3 and 5 nucleotides) from the third DNA-binding protein target sequence, in which the third and fourth DNA-binding protein target sequences can hybridize to each other to form a hairpin in the second donor template. Further, the two ssHDRT regions in the two donor templates can hybridize to each other to bring the two donor templates together to form the double hairpin donor construct.

Some exemplary sequences of the donor templates in the double hairpin donor construct are shown in SEQ ID NOS: 16 and 17. As can be seen in the sequence of SEQ ID NO:16, the first donor template contains a first DNA-binding protein target sequence (bold in SEQ ID NO:16) and a second DNA-binding protein target sequence located downstream from the first DNA-binding protein target sequence (underlined in SEQ ID NO:16), in which the first and second DNA-binding protein target sequences can hybridize to each other to form a hairpin in the first donor template. The second donor template contains a third DNA-binding protein target sequence (bold in SEQ ID NO:17) and a fourth DNA-binding protein target sequence located downstream from the third DNA-binding protein target sequence (underlined in SEQ ID NO:17), in which the third and fourth DNA-binding protein target sequences can hybridize to each other to form a hairpin in the second donor template. Further, the double-underlined portion in the sequence of SEQ ID NO:16 and the double-underlined portion in the sequence of SEQ ID NO:17 can hybridize to each other to bring the two donor templates together to form the double hairpin donor construct.

A hairpin is formed when two polynucleotide regions within the same polynucleotide strand hybridize to form a double helix or a double-stranded duplex that ends in an unpaired loop. In some embodiments, the unpaired loop in the hairpin has between 4 and 200 (e.g., between 4 and 180, between 4 and 160, between 4 and 140, between 4 and 120, between 4 and 100, between 4 and 80, between 4 and 60, between 4 and 40, between 4 and 20, between 4 and 10, between 4 and 8, between 8 and 200, between 10 and 200, between 20 and 200, between 40 and 200, between 60 and 200, between 80 and 200, between 100 and 200, between 120 and 200, between 140 and 200, between 160 and 200, or between 180 and 200) nucleotides. In some embodiments, each of the two polynucleotide regions that hybridize in a hairpin is between 10 and 50 (e.g., between 10 and 45, between 10 and 40, between 10 and 35, between 10 and 30, between 10 and 25, between 10 and 20, between 10 and 15, between 15 and 50, between 20 and 50, between 25 and 50, between 30 and 50, between 35 and 50, between 40 and 50, or between 45 and 50) nucleotides.

Characteristics of Donor Templates

Moreover, in a donor template described herein, the donor template can further include a protospacer adjacent motif (PAM) sequence. The Cas9 protein identifies the target nucleic acid by first identifying a 3-base pair PAM located 3' of the target nucleic acid. Once the PAM is identified, the target gRNA in the RNP complex hybridizes to the target nucleic acid upstream of the PAM. The donor template in a donor construct can further contain one or more edge sequences at either or both of the 5' and 3' termini of the donor template. An edge sequence in the donor template can facilitate binding between the donor template and the DNA-binding protein (e.g., an RNA-guided nuclease). In some embodiments, an edge sequence can have at least 2 nucleotides, e.g., between 2 and 24 nucleotides (e.g., between 2 and 22, between 2 and 20, between 2 and 18, between 2 and 16, between 2 and 14, between 2 and 12, between 2 and 10, between 2 and 8, between 2 and 6, between 2 and 4, between 4 and 24, between 6 and 24, between 8 and 24, between 10 and 24, between 12 and 24, between 14 and 24, between 16 and 24, between 18 and 24, between 20 and 24, or between 22 and 24 nucleotides; 2, 3, 4, 5, 6, 7, 8, 9, 10, 11, 12, 13, 14, 15, 16, 17, 18, 19, 20, 21, 22, 23, or 24 nucleotides).

In some embodiments, the size or length of the donor template in the donor construct is greater than about 200 bp, 250 bp, 300 bp, 350 bp, 400 bp, 450 bp, 500 bp, 550 bp, 600 bp, 650 bp, 700 bp, 750 bp, 800 bp, 850 bp, 900 bp, 1 kb, 1.1 kb, 1.2 kb, 1.3 kb, 1.4 kb, 1.5 kb, 1.6 kb, 1.7 kb, 1.8 kb, 1.9 kb, 2.0 kb, 2.1 kb, 2.2 kb, 2.3 kb, 2.4 kb, 2.5 kb, 2.6 kb, 2.7 kb, 2.8 kb, 2.9 kb, 3 kb, 3.1 kb, 3.2 kb, 3.3 kb, 3.4 kb, 3.5 kb, 3.6 kb, 3.7 kb, 3.8 kb, 3.9 kb, 4.0 kb, 4.1 kb, 4.2 kb, 4.3 kb, 4.4 kb, 4.5 kb, 4.6 kb, 4.7 kb, 4.8 kb, 4.9 kb, 5.0 kb, 5.1 kb, 5.2 kb, 5.3 kb, 5.4 kb, 5.5 kb, 5.6 kb, 5.7 kb, 5.8 kb, 5.9 kb, 6.0 kb, 6.1 kb, 6.2 kb, 6.3 kb, 6.4 kb, 6.5 kb, 6.6 kb, 6.7 kb, 6.8 kb, 6.9 kb, 7.0 kb, 7.1 kb, 7.2 kb, 7.3 kb, 7.4 kb, 7.5 kb, 7.6 kb, 7.7 kb, 7.8 kb, 7.9 kb, 8.0 kb, 8.1 kb, 8.2 kb, 8.3 kb, 8.4 kb, 8.5 kb, 8.6 kb, 8.7 kb, 8.8 kb, 8.9 kb, 9.0 kb, 9.1 kb, 9.2 kb, 9.3 kb, 9.4 kb, 9.5 kb, 9.6 kb, 9.7 kb, 9.8 kb, 9.9 kb, 10.0 kb, any size of template in between these sizes, or greater than 10 kb. For example, the size of the template can be about 200 bp to about 500 bp, about 200 bp to about 750 bp, about 200 bp to about 1 kb, about 200 bp to about 1.5 kb, about 200 bp to about 2.0 kb, about 200 bp to about 2.5 kb, about 200 bp to about 3.0 kb, about 200 bp to about 3.5 kb, about 200 bp to about 4.0 kb, about 200 bp to about 4.5 kb, about 200 bp to about 5.0 kb.

III. Compositions

The disclosure provides compositions and methods for modifying a target nucleic acid that include: (a) a targetable nuclease; (b) a DNA-binding protein; and (c) a donor construct described herein. The targetable nuclease and DNA-binding protein can be the same, e.g., an RNA-guided nuclease (e.g., a Cas protein, described in detail further herein). The composition can comprise a target guide RNA (gRNA) and a donor gRNA. In certain embodiments, the target gRNA is complementary to the target nucleic acid. In some embodiments, the DNA-binding protein target sequence is complementary to an equal length portion of the sequence of the donor gRNA.

The DNA-binding protein can directly or indirectly bind to the DNA-binding protein target sequence within the donor construct. As described in detail further herein, in some embodiments, when the DNA-binding protein is a transcription activator-like (TAL) effector DNA-binding protein, the TAL effector DNA-binding protein can directly recognize and bind to the DNA-binding target sequence. In some embodiments, when the DNA-binding protein is a zinc finger DNA-binding protein, the zinc finger DNA-binding protein can directly recognize and bind to the DNA-binding target sequence. In other embodiments, when the DNA-binding protein is an RNA-guided nuclease (e.g., a Cas protein), the RNA-guided nuclease can indirectly bind to a DNA-binding protein target sequence via a donor gRNA, which can hybridize to the DNA-binding protein target sequence. Without being bound by any theory, the DNA-binding protein serves to transport or shuttle the donor construct to a cellular location close to the target nucleic acid. Thus, the DNA-binding protein can improve the delivery of the HDRT into target cells, especially to the cell nucleus, and increase knock-in efficiencies.

In some embodiments, the targetable nuclease is fused to a nuclear localization signal (NLS) sequence. In some embodiments, the DNA-binding protein is fused to an NLS sequence. Examples of NLS sequences are known in the art, e.g., as described in Lange et al., *J Biol Chem.* 282(8):5101-5, 2007, and also include, but are not limited to, AVKRPAATKKAGQAKKKKLD (SEQ ID NO:25), MSRRRKANPTKLSENAKKLAKEVEN (SEQ ID NO:26), PAAKRVKLD (SEQ ID NO:27), KLKIKRPVK (SEQ ID NO:28), and PKKKRKV (SEQ ID NO:29). Examples of other peptide or proteins that can be fused to a RNA-guided nuclease, such as cell-penetrating peptides and cell-targeting peptides are available in the art and described, e.g., Vivès et al., *Biochim Biophys Acta.* 1786(2):126-38, 2008. In certain embodiments, the targetable nuclease has nuclease activity. In yet other embodiments, the targetable nuclease does not have nuclease activity.

Further, an anionic polymer can be added to the composition. Without being bound by any theory, the addition of an anionic polymer to the composition can stabilize the Cas protein and sgRNA ribonucleoprotein (RNP) complex and prevents aggregation. Examples of anionic polymers are described further herein.

In some embodiments of the composition, the target gRNA and the donor gRNA can have the same sequence. In other embodiments, the target gRNA and the donor gRNA have the different sequences.

In some embodiments of the compositions described herein, the targetable nuclease is a first RNA-guided nuclease, the DNA-binding protein is a second RNA-guided nuclease, and the donor template in the donor construct further comprises one or more protospacer adjacent motifs (PAMs). In some embodiments, the composition also further comprises a target gRNA that is complementary to the target nucleic acid and a donor gRNA that hybridizes to the DNA-binding protein target sequence. The target gRNA can form a first RNP complex with the first RNA-guided nuclease and guide the first RNA-guided nuclease (e.g., Cas protein) to the target nucleic acid. In some embodiments, a portion of the target gRNA (e.g., a portion of the target gRNA that is at least 15 nucleotides (e.g., 15, 16, 17, 18, 19, 20, 21, 22, 23, 24, or 25 nucleotides) is complementary to the target nucleic acid. The donor gRNA can form a second RNP with the second RNA-guided nuclease. The DNA-binding protein target sequence in the donor template can hybridize to the donor gRNA or a portion thereof. Therefore, the complex containing the second RNA-guided nuclease, the donor gRNA, and the donor construct can bring the donor construct into the desired intracellular location (e.g., the nucleus) for homologous recombination to occur at the integration site in the target nucleic acid. In some embodiments, the first and second RNA-guided nucleases are the same. In other embodiments, the first and second RNA-guided nucleases are different. In other embodiments, a composition described herein can also be used for integrating the donor construct through non-homology directed repair mediated methods, such as homology independent targeted integration (HITI).

IV. Single-Guide RNAs

A Cas protein may be guided to its target DNA by a single-guide RNA (sgRNA). An sgRNA is a version of the naturally occurring two-piece guide RNA (crRNA and tracrRNA) engineered into a single, continuous sequence. An sgRNA may contain a guide sequence (e.g., the crRNA equivalent portion of the sgRNA) that targets the Cas protein to the target DNA and a scaffold sequence that interacts with the Cas protein (e.g., the tracrRNAs equivalent portion of the sgRNA). An sgRNA may be selected using a software. As a non-limiting example, considerations for selecting an sgRNA can include, e.g., the PAM sequence for the Cas9 protein to be used, and strategies for minimizing off-target modifications. Tools, such as NUPACK® and the CRISPR Design Tool, can provide sequences for preparing the sgRNA, for assessing target modification efficiency, and/or assessing cleavage at off-target sites. In some embodiments, instead of a sgRNA, a gRNA can also delivered as a two-piece component containing the crRNA and the tracrRNA.

Guide Sequence

The guide sequence in the sgRNA may be complementary to a specific sequence within a target DNA. The 3' end of the target DNA sequence can be followed by a PAM sequence. Approximately 20 nucleotides upstream of the PAM sequence is the target DNA. In general, a Cas9 protein or a variant thereof cleaves about three nucleotides upstream of the PAM sequence. The guide sequence in the sgRNA can be complementary to either strand of the target DNA.

In some embodiments, the guide sequence of an sgRNA may comprise about 10 to about 2000 nucleic acids, for example, about 10 to about 100 nucleic acids, about 10 to about 500 nucleic acids, about 10 to about 1000 nucleic acids, about 10 to about 1500 nucleic acids, about 10 to about 2000 nucleic acids, about 50 to about 100 nucleic acids, about 50 to about 500 nucleic acids, about 50 to about 1000 nucleic acids, about 50 to about 1500 nucleic acids, about 50 to about 2000 nucleic acids, about 100 to about 500 nucleic acids, about 100 to about 1000 nucleic acids, about 100 to about 1500 nucleic acids, about 100 to about 2000 nucleic acids, about 500 to about 1000 nucleic acids, about 500 to about 1500 nucleic acids, about 500 to about 2000 nucleic acids, about 1000 to about 1500 nucleic acids, about 1000 to about 2000 nucleic acids, or about 1500 to about 2000 nucleic acids at the 5' end of the sgRNA that can direct the Cas protein to the target DNA site using RNA-DNA complementarity base pairing. In some embodiments, the guide sequence of an sgRNA comprises about 100 nucleic acids at the 5' end of the sgRNA that can direct the Cas protein to the target DNA site using RNA-DNA complementarity base pairing. In some embodiments, the guide sequence comprises 20 nucleic acids at the 5' end of the sgRNA that can direct the Cas protein to the target DNA site using RNA-DNA complementarity base pairing. In other embodiments, the guide sequence comprises less than 20, e.g., 19, 18, 17, 16, 15 or less, nucleic acids that are complementary to the target DNA site. In some instances, the guide sequence in the sgRNA contains at least one nucleic acid mismatch in the complementarity region of the target DNA site. In some instances, the guide sequence contains about 1 to about 10 nucleic acid mismatches (e.g., 1, 2, 3, 4, 5, 6, 7, 8, 9, or 10 nucleic acid mismatches) in the complementarity region of the target DNA site.

Scaffold Sequence

The scaffold sequence in the sgRNA may serve as a protein-binding sequence that interacts with the Cas protein or a variant thereof. In some embodiments, the scaffold sequence in the sgRNA can comprise two complementary stretches of nucleotides that hybridize to one another to form a double-stranded RNA duplex (dsRNA duplex). The scaffold sequence may have structures such as lower stem, bulge, upper stem, *nexus*, and/or hairpin. In some embodiments, the scaffold sequence in the sgRNA can be between about 90 nucleic acids to about 120 nucleic acids, e.g., about 90 nucleic acids to about 115 nucleic acids, about 90 nucleic acids to about 110 nucleic acids, about 90 nucleic acids to about 105 nucleic acids, about 90 nucleic acids to about 100 nucleic acids, about 90 nucleic acids to about 95 nucleic acids, about 95 nucleic acids to about 120 nucleic acids, about 100 nucleic acids to about 120 nucleic acids, about 105 nucleic acids to about 120 nucleic acids, about 110 nucleic acids to about 120 nucleic acids, or about 115 nucleic acids to about 120 nucleic acids.

V. Target gRNA and Donor gRNA

Guide RNAs (gRNAs) in general refer to a DNA-targeting RNA containing (1) a guide sequence that is complementary to a target nucleic acid and guides the RNA-guided nuclease to the target nucleic acid and (2) a scaffold sequence that interacts and binds with the RNA-guided nuclease. In some embodiments of the disclosure, the target gRNA and the donor gRNA have the same sequence. In other embodiments of the disclosure, the target gRNA and the donor gRNA have different sequences. In the compositions and methods described herein, a target gRNA comprises a portion that is complementary to the target nucleic acid. Once the target gRNA forms an RNP complex with the targetable nuclease (e.g., a first RNA-guided nuclease), the RNP complex can be guided to the target nucleic acid by the complementarity between the target gRNA and the target nucleic acid. In some embodiments, the targetable nuclease is a Cas protein, such as a Cas9 protein. The Cas9 protein identifies the target nucleic acid by first identifying a 3-base pair protospacer adjacent motif (PAM) located 3' of the target nucleic acid. Once the PAM is identified, the target gRNA in the RNP complex hybridizes to the target nucleic acid upstream of the PAM. In some embodiments, a target gRNA includes a portion of nucleotides that are complementary to a portion in the target nucleic acid that is approximately 20 nucleotides upstream of the PAM sequence. In general, a Cas9 protein or a variant thereof cleaves about three nucleotides upstream of the PAM sequence. A gRNA can be selected using a software. As a non-limiting example, considerations for selecting a gRNA can include, e.g., the PAM sequence for the RNA-guided nuclease to be used, and strategies for minimizing off-target modifications. Tools, such as NUPACK® and the CRISPR Design Tool, can provide sequences for preparing the gRNA, for assessing target modification efficiency, and/or assessing cleavage at off-target sites.

In some embodiments, the target gRNA comprises a portion of at least 15 nucleotides (e.g., 15, 16, 17, 18, 19, 20, 21, 22, 23, 24, or 25 nucleotides) that are complementary to the target nucleic acid. In some embodiments, the target gRNA can be completely complementary or partially complementary to the target nuclei acid. In some embodiments, at least 60% (e.g., 65%, 70%, 75%, 80%, 85%, 90%, 95%, or 97%) of the nucleotides in the target nucleic acid can engage in Watson-Crick base pairing with their corresponding nucleotides in the target gRNA.

Similar to the target gRNA, the donor gRNA forms a complex with the DNA-binding protein (e.g., a RNA-guided nuclease). In the compositions and methods described herein, a donor gRNA comprises a portion that is complementary to the DNA-binding protein target sequence. Once the donor gRNA forms an RNP complex with the DNA-binding protein (e.g., a RNA-guided nuclease), the RNP complex can be guided to the donor construct by the complementarity between the donor gRNA and the DNA-binding protein target sequence. In some embodiments, the DNA-binding protein target sequence is complementary to an equal length portion of the sequence of the donor gRNA. In some embodiments, the donor gRNA comprises a portion of at least 15 nucleotides (e.g., 15, 16, 17, 18, 19, 20, 21, 22, 23, 24, or 25 nucleotides) that can hybridize to the DNA-binding protein target sequence. The donor gRNA can be completely complementary or partially complementary to the DNA-binding protein target sequence. In some embodiments, at least 60% (e.g., 65%, 70%, 75%, 80%, 85%, 90%, 95%, or 97%) of the nucleotides in the DNA-binding protein target sequence can engage in Watson-Crick base pairing with their corresponding nucleotides in the donor gRNA. In some embodiments, the DNA-binding protein target sequence can have at least one (e.g., one, two, three, four, five, six, seven, eight, nine, or ten) mismatched nucleotide to its corresponding nucleotide in the donor gRNA when the DNA-binding protein target sequence and the donor gRNA are hybridized. Examples of mismatched bases include a guanine and uracil, guanine and thymine, and adenine and cytosine pairing.

In some embodiments of the disclosure, the target gRNA and the donor gRNA have the same sequence and each of the targetable nuclease and the DNA-binding protein is an RNA-guided nuclease (e.g., a Cas protein). In this case, the gRNA can form a first RNP complex with the RNA-guided nuclease. The first RNP complex can bind to the target nucleic acid via the hybridization between the gRNA and the target nucleic acid. The gRNA can also form a second RNP complex with the RNA-guided nuclease and the donor construct. In this second RNP complex, the gRNA can bind to the DNA-binding protein target sequence to bring the donor construct to the desired intracellular location (e.g., the nucleus) for homologous recombination to occur at the cleaved target nucleic acid. In some embodiments, the gRNA and the DNA-binding protein target sequence only have partial complementarity.

VI. Targetable Nuclease

As described above, in some embodiments of the compositions and methods described herein, the targetable nuclease is an RNA-guided nuclease (e.g., a Cas protein). The targetable nuclease can recognize a sequence of a target nucleic acid (e.g., a target gene within a genome), bind to the target nucleic acid, and modify the target nucleic acid. In other embodiments, the targetable nuclease can be a fusion protein that includes a protein that can bind to the target nucleic acid and a protein that can modify the target nucleic acid (e.g., a nuclease, a transcription activator or repressor).

In some embodiments, the targetable nuclease has nuclease activity. For example, the targetable nuclease can modify the target nucleic acid by cleaving the target nucleic acid. The cleaved target nucleic acid can then undergo homologous recombination with a nearby a HDRT. For example, the Cas nuclease can direct cleavage of one or both strands at a location in a target nucleic acid. Non-limiting examples of Cas nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, variants thereof, mutants thereof, and derivatives thereof. There are three main types of Cas nucleases (type I, type II, and type III), and 10 subtypes including 5 type I, 3 type II, and 2 type III proteins (see, e.g., Hochstrasser and Doudna, *Trends Biochem Sci,* 2015:40(1):58-66). Type II Cas nucleases include Cas1, Cas2, Csn2, Cas9, and Cfp1. These Cas nucleases are known to those skilled in the art. For example, the amino acid sequence of the *Streptococcus pyogenes* wild-type Cas9 polypeptide is set forth, e.g., in NBCI Ref. Seq. No. NP 269215, and the amino acid sequence of *Streptococcus thermophilus* wild-type Cas9 polypeptide is set forth, e.g., in NBCI Ref. Seq. No. WP_011681470.

Cas nucleases, e.g., Cas9 nucleases, can be derived from a variety of bacterial species including, but not limited to, *Veillonella atypical, Fusobacterium nucleatum, Filifactor alocis, Solobacterium moorei, Coprococcus catus, Treponema denticola, Peptoniphilus duerdenii, Catenibacterium mitsuokai, Streptococcus mutans, Listeria innocua, Staphylococcus pseudintermedius, Acidaminococcus intestine, Olsenella uli, Oenococcus kitaharae, Bifidobacterium bifidum, Lactobacillus rhamnosus, Lactobacillus gasseri, Finegoldia magna, Mycoplasma mobile, Mycoplasma gallisepticum, Mycoplasma ovipneumoniae, Mycoplasma canis, Mycoplasma synoviae, Eubacterium rectale, Streptococcus thermophilus, Eubacterium dolichum, Lactobacillus coryniformis* subsp. *Torquens, Ilyobacter polytropus, Ruminococcus albus, Akkermansia muciniphila, Acidothermus cellulolyticus, Bifidobacterium longum, Bifidobacterium dentium, Corynebacterium diphtheria, Elusimicrobium minutum, Nitratifractor salsuginis, Sphaerochaeta globus, Fibrobacter succinogenes* subsp. *Succinogenes, Bacteroides fragilis, Capnocytophaga ochracea, Rhodopseudomonas palustris, Prevotella micans, Prevotella ruminicola, Flavobacterium columnare, Aminomonas paucivorans, Rhodospirillum rubrum, Candidatus Puniceispirillum marinum, Verminephrobacter eiseniae, Ralstonia syzygii, Dinoroseobacter shibae, Azospirillum, Nitrobacter hamburgensis, Bradyrhizobium, Wolinella succinogenes, Campylobacter jejuni* subsp. *Jejuni, Helicobacter mustelae, Bacillus cereus, Acidovorax ebreus, Clostridium perfringens, Parvibaculum lavamentivorans, Roseburia intestinalis, Neisseria meningitidis, Pasteurella multocida* subsp. *Multocida, Sutterella wadsworthensis, proteobacterium, Legionella pneumophila, Parasutterella excrementihominis, Wolinella succinogenes*, and *Francisella novicida.*

Cas9 protein refers to an RNA-guided double-stranded DNA-binding nuclease protein or nickase protein. Wild-type Cas9 nuclease has two functional domains, e.g., RuvC and HNH, that cut different DNA strands. Cas9 can induce double-strand breaks in genomic DNA (target DNA) when both functional domains are active. The Cas9 enzyme can comprise one or more catalytic domains of a Cas9 protein derived from bacteria belonging to the group consisting of *Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor*, and *Campylobacter*. In some embodiments, the Cas9 can be a fusion protein, e.g., the two catalytic domains are derived from different bacteria species.

In some embodiments, a Cas protein can be a Cas protein variant. For example, useful variants of the Cas9 nuclease can include a single inactive catalytic domain, such as a $RuvC^-$ or $HNH^-$ enzyme or a nickase. A Cas9 nickase has only one active functional domain and can cut only one strand of the target DNA, thereby creating a single strand break or nick. In some embodiments, the Cas9 nuclease can be a mutant Cas9 nuclease having one or more amino acid mutations. For example, the mutant Cas9 having at least a D10A mutation is a Cas9 nickase. In other embodiments, the mutant Cas9 nuclease having at least a H840A mutation is a Cas9 nickase. Other examples of mutations present in a Cas9 nickase include, without limitation, N854A and N863A. A double-strand break can be introduced using a Cas9 nickase if at least two DNA-targeting RNAs that target opposite DNA strands are used. A double-nicked induced double-strand break can be repaired by NHEJ or HDR (Ran et al., 2013, Cell, 154:1380-1389). Non-limiting examples of Cas9 nucleases or nickases are described in, for example, U.S. Pat. Nos. 8,895,308; 8,889,418; and 8,865,406 and U.S. Application Publication Nos. 2014/0356959, 2014/0273226 and 2014/0186919. The Cas9 nuclease or nickase can be codon-optimized for the target cell or target organism.

In some embodiments, a Cas protein variant that lacks cleavage (e.g., nickase) activity. A Cas protein variant may contain one or more point mutations that eliminates the protein's nickase activity. In some embodiments, such Cas protein variants can be fused to other proteins and serve as targeting domains to direct the other proteins to the target nucleic acid. For example, Cas protein variants without nickase activity may be fused to transcriptional activation or repression domains to control gene expression (Ma et al., *Protein and Cell,* 2(11):879-888, 2011; Maeder et al., *Nature Methods,* 10:977-979, 2013; and Konermann et al., *Nature,* 517:583-588, 2014). A Cas protein variant that lacks nickase activity may be used to target genomic regions, resulting in RNA-directed transcriptional control. In some embodiments, a Cas protein variant without any cleavage (e.g., nickase) activity may be used to target an exogenous protein to the target nucleic acid. An exogenous protein may be fused to the Cas protein variant and the fusion protein may be enhanced by the addition of the anionic polymer. An exogenous protein may be an effector protein domain. An exogenous protein may be a transcription activator or repressor. Other examples of exogenous proteins include, but are not limited to, VP64-p65-Rta (VPR), VP64, P65, Krab, Ten-eleven translocation methylcytosine dioxygenase (TET), and DNA methyltransferase (DNMT). Specific Cas protein variants that lack cleavage (e.g., nickase) activity are also described below.

In some embodiments, the Cas nuclease can be a high-fidelity or enhanced specificity Cas9 polypeptide variant with reduced off-target effects and robust on-target cleavage. Non-limiting examples of Cas9 polypeptide variants with improved on-target specificity include the SpCas9 (K855A), SpCas9 (K810A/K1003A/R1060A) (also referred to as eSpCas9(1.0)), and SpCas9 (K848A/K1003A/R1060A) (also referred to as eSpCas9(1.1)) variants described in Slaymaker et al., *Science,* 351(6268):84-8 (2016), and the SpCas9 variants described in Kleinstiver et al., *Nature,* 529(7587): 490-5 (2016) containing one, two, three, or four of the following mutations: N497A, R661A, Q695A, and Q926A (e.g., SpCas9-HF1 contains all four mutations).

In some embodiments, a targetable nuclease can also be can be a fusion protein that contains a protein that can bind to the target nucleic acid and a protein that can cleave the target nucleic acid. For example, a protein that can recognize and bind to the target nucleic acid can be a Cas protein variant without any cleavage activity. A Cas protein variant without any cleavage activity can be a Cas9 polypeptide that contains two silencing mutations of the RuvC1 and HNH nuclease domains (D10A and H840A), which is referred to as dCas9 (Jinek et al., *Science,* 2012, 337:816-821; Qi et al., *Cell,* 152(5):1173-1183). In one embodiment, the dCas9 polypeptide from *Streptococcus pyogenes* comprises at least one mutation at position D10, G12, G17, E762, H840, N854, N863, H982, H983, A984, D986, A987 or any combination thereof. Descriptions of such dCas9 polypeptides and variants thereof are provided in, for example, International Patent Publication No. WO 2013/176772. The dCas9 enzyme can contain a mutation at D10, E762, H983, or D986, as well as a mutation at H840 or N863. In some instances, the dCas9 enzyme can contain a D10A or D10N mutation. Also, the dCas9 enzyme can contain a H840A, H840Y, or H840N. In some embodiments, the dCas9 enzyme can contain D10A and H840A; D10A and H840Y; D10A and H840N; D10N and H840A; D10N and H840Y; or D10N and H840N substitutions. The substitutions can be conservative or non-conservative substitutions to render the Cas9 polypeptide catalytically inactive and able to bind to target DNA.

In other embodiments, a protein that can recognize and bind to the target nucleic acid can be a transcription activator-like (TAL) effector DNA-binding protein or a zinc finger DNA-binding protein. The TAL effector DNA-binding protein has a central domain of DNA-binding tandem repeats usually containing 33-35 amino acids in length and two hypervariable amino acid residues at positions 12 and 13 that can recognize one or more specific DNA base pairs. The zinc finger DNA-binding protein has a DNA-binding motif that is often characterized by the absence or presence one or more zinc ions in order to coordinate and stabilize the motif fold. The zinc finger DNA-binding protein contains multiple finger-like protrusions that make tandem contacts with their target molecule. Some zinc finger DNA-binding proteins also form salt bridges to stabilize the finger-like folds. They were first identified as a DNA-binding motif in transcription factor TFIIIA from *Xenopus laevis* (African clawed frog), however they are now recognized to bind DNA, RNA, protein, and/or lipid substrates.

In some embodiments, a targetable nuclease in the compositions and methods described herein can be a fusion protein containing a TAL effector DNA-binding protein and a protein that can cleave the target nucleic acid (also referred to as "Transcription activator-like effector nucleases (TALEN)"). In other embodiments, a targetable nuclease in the compositions and methods described herein can be a fusion protein containing a zinc finger DNA-binding protein and a protein that can cleave the target nucleic acid. For example, a protein that can cleave the target nucleic acid can be a wild-type or mutated FokI endonuclease or the catalytic domain of FokI. Detailed descriptions of TALENs and their uses for gene editing are found, e.g., in U.S. Pat. Nos. 8,440,431; 8,440,432; 8,450,471; 8,586,363; and 8,697,853; Scharenberg et al., *Curr Gene Ther,* 2013, 13(4):291-303; Gaj et al., *Nat Methods,* 2012, 9(8):805-7; Beurdeley et al., *Nat Commun,* 2013, 4:1762; and Joung and Sander, *Nat Rev Mol Cell Biol,* 2013, 14(1):49-55. Examples of a zinc finger DNA-binding protein fused to a protein that can cleave the target nucleic acid are described in the art and include, but are not limited to, those described in Umov et al., *Nature Reviews Genetics,* 2010, 11:636-646; Gaj et al., *Nat Methods,* 2012, 9(8):805-7; U.S. Pat. Nos. 6,534,261; 6,607,882; 6,746,838; 6,794,136; 6,824,978; 6,866,997; 6,933,113; 6,979,539; 7,013,219; 7,030,215; 7,220,719; 7,241,573; 7,241,574; 7,585,849; 7,595,376; 6,903,185; 6,479,626; and U.S. Application Publication Nos. 2003/0232410 and 2009/0203140.

In some embodiments, the targetable nuclease does not have nuclease activity. For example, the targetable nuclease (e.g., a targetable nuclease without any nuclease activity)

can regulate the expression of the target nucleic acid. In some embodiments, the targetable nuclease can be a fusion protein that includes a protein that can bind to the target nucleic acid, such as a Cas protein variant without any cleavage activity (e.g., a dCas9), a TAL effector DNA-binding protein, and a zinc finger DNA-binding protein as described above, and a protein that can modify the target nucleic acid, such as a transcription activator or repressor. In some embodiments, a Cas protein variant without any cleavage activity (e.g., a dCas9) can bind to the double-stranded duplex formed by the DNA-binding protein target sequences in a donor construct, while a Cas protein with cleavage activity can cleave the target nucleic for it to undergo homologous recombination with the HDRT in the donor construct.

VII. DNA-Binding Protein

A DNA-binding protein is a protein that can directly or indirectly bind to a DNA-binding protein target sequence within a donor template (which includes an HDRT). In some embodiments, a DNA-binding protein can be an RNA-guided nuclease (e.g., a Cas protein) that can recognize and bind the DNA-binding protein target sequence, but not cleave the DNA-binding protein target sequence. The RNA-guided nuclease can bind to the DNA-binding protein target sequence via the donor gRNA as described above. In some embodiments, the donor gRNA and the DNA-binding protein target sequence can have partial complementarity which allows the RNA-guided nuclease to bind to the DNA-binding protein target sequence via the donor gRNA but not cleave the DNA-binding protein target sequence. In other embodiments, a DNA-binding protein can be a Cas protein variant without any cleavage activity (e.g., a dCas9), a TAL effector DNA-binding protein, or a zinc finger DNA-binding protein as described above. Each of the TAL effector DNA-binding protein and zinc finger DNA-binding protein can directly bind to a DNA-binding protein target sequence. Without being bound by any theory, the DNA-binding protein serves to transport or shuttle the donor construct to a cellular location close to the target nucleic acid (e.g., the nucleus).

VIII. DNA-Binding Protein Target Sequence

A DNA-binding protein target sequence is a nucleotide sequence that is recognized and bound by a DNA-binding protein. In the compositions and methods described herein, one or more DNA-binding protein target sequences are in a donor template, together with an HDRT, such that the HDRT can be brought or "shuttled" into the desired intracellular location (e.g., the nucleus) to be near the target nucleic acid. Thus, the DNA-binding protein target sequence can help to improve homology directed repair efficiency and target nucleic acid modification efficiency. In some embodiments, the DNA-binding protein target sequence can have at least 90% (e.g., 91%, 92%, 93%, 94%, 95%, 96%, 97%, 98%, 99%, or 100%) sequence identity to a sequence of any one of SEQ ID NOS:30-35.

In some embodiments, a DNA-binding protein target sequence can be directly recognized and bound by a DNA-binding protein, e.g., a TAL effector DNA-binding protein or zinc finger DNA-binding protein. In other embodiments, a DNA-binding protein target sequence can be indirectly recognized and bound by a DNA-binding protein, e.g., an RNA-guided nuclease, via a donor gRNA. In some embodiments, at least 60% (e.g., 65%, 70%, 75%, 80%, 85%, 90%, 95%, or 97%) of the nucleotides in the DNA-binding protein target sequence can engage in Watson-Crick base pairing with their corresponding nucleotides in the donor gRNA. In some embodiments, the DNA-binding protein target sequence can have at least one (e.g., one, two, three, four, five, six, seven, eight, nine, or ten) mismatched nucleotide to its corresponding nucleotide in the donor gRNA when the DNA-binding protein target sequence and the donor gRNA are hybridized. Examples of mismatched bases include a guanine and uracil, guanine and thymine, and adenine and cytosine pairing. In some embodiments, the DNA-binding protein target sequence is a portion of the target nucleic acid.

The DNA-binding protein target sequence is only recognized and bound, but not cut, by the DNA-binding protein (e.g., an RNA-guided nuclease). In some embodiments, the DNA-binding protein target sequence is complementary to an equal length portion of the sequence of the donor gRNA. In some embodiments, the DNA-binding protein target sequence has at least 14 nucleotides, e.g., between 14 and 20 nucleotides (e.g., between 14 and 19, between 14 and 18, between 14 and 17, between 14 and 16, or between 14 and 15 nucleotides; 14, 15, 16, 17, 18, 19, or 20 nucleotides). A DNA-binding protein target sequence can include 12-20, 14-20, 14-19, 16-18, 15-17, 12, 13, 14, 15, 16, 17, 18, 19, or 20 nucleotides. In some embodiments, the DNA-binding protein target sequence is partially complementarity, i.e., comprises nucleotide mismatches, compared to an equal length portion of the sequence of the donor gRNA. For example, the DNA-binding protein target sequence having 20 nucleotides can have between 1 and 6 nucleotide mismatches (e.g., between 1 and 5, between 1 and 4, between 1 and 3, between 1 and 2 nucleotide mismatches; 1, 2, 3, 4, 5, or 6 nucleotide mismatches) compared to a 20-nucleotide portion of the sequence of the donor gRNA.

IX. Anionic Polymers

In some embodiments of the compositions described herein, an anionic polymer can be added to a composition, e.g., to improve the stability and editing efficiency of Cas9 protein and sgRNA ribonucleoprotein complex (RNP). In some embodiments, the addition of anionic polymers to a composition containing a Cas protein (e.g., a Cas9 protein) or a composition containing a Cas protein (e.g., a Cas9 protein) and sgRNA RNP complex can stabilize the Cas protein or the RNP complex and prevent aggregation, leading to high nuclease activity and editing efficiency. Without being bound by any theory, the anionic polymer (e.g., PGA) may interact favorably with the Cas protein, i.e., the anionic polymer (e.g., PGA) may interact favorably with the positively-charged (at physiological pH) Cas9 protein, stabilize the RNP complex into dispersed particles, prevent aggregation, and improve nuclease editing activity and efficiency. An anionic polymer can be water soluble. An anionic polymer can be biologically inert. In some aspects an anionic polymer is not a DNA sequence. An anionic polymer can be capable of undergoing freeze/thaw cycling while retaining full or substantial functionality. An anionic polymer can be lyophilized while retaining full or substantial functionality. An anionic polymer can have a molecular weight of 15,000 to 50,000 kDa (e.g., 15,000 to 45,000 kDa, 15,000 to 40,000 kDa, 15,000 to 35,000 kDa, 15,000 to 30,000 kDa, 15,000 to 25,000 kDa, 15,000 to 20,000 kDa, 20,000 to 50,000 kDa, 25,000 to 50,000 kDa, 30,000 to 50,000 kDa, 35,000 to 50,000 kDa, 40,000 to 50,000 kDa, or 45,000 to 50,000 kDa).

An anionic polymer can be polyglutamic acid (PGA). In some embodiments, a single-stranded donor oligonucleotides (ssODN) can be used instead of or in addition to an anionic polymer. Examples of ssODNs are described in, e.g., Okamoto et al., *Scientific Report* 9:4811, 2019; and Hu et al., *Nucleic Acids,* 17:P198, 2019.

An anionic polymer described herein can be added to a composition to stabilize the composition, improve editing, reduce toxicity, and enable lyophilization of the composition without loss of activity. In some embodiments, a composition containing the Cas protein and the anionic polymer is an aqueous composition that appears homogenous, has a clear visual appearance, and is free of cloudy precipitates or aggregates. In some embodiments, a composition containing the Cas protein and sgRNA RNP complex and the anionic polymer is an aqueous composition that appears homogenous, has a clear visual appearance, and is free of cloudy precipitates or aggregates. In some embodiments, a composition comprising a targetable nuclease, a DNA-binding protein, a donor construct, and an anionic polymer is an aqueous composition that appears homogenous, has a clear visual appearance, and is free of cloudy precipitates or aggregates. Having a stable composition allows efficiency gene knock-outs and large transgene knock-ins with high cell survival rate. Further, the composition can also be lyophilized for long-term storage and reconstituted for later use. A composition comprising an anionic polymer can also be used in methods of modifying a target nucleic acid, where the target nucleic acid can be removed, replaced by an exogenous nucleic acid sequence, or an exogenous nucleic acid sequence can be inserted within the target nucleic acid.

An anionic polymer that can be added to a composition described herein is a molecule composed of subunits or monomers that has an overall negative charge. An anionic polymer can be an anionic polypeptide or an anionic polysaccharide. An anionic polypeptide is an anionic polymer that has at least 50% (e.g., 55%, 60%, 65%, 70%, 75%, 80%, 85%, 90%, 95%, or 100%) of its subunits or monomers being amino acids, such as acidic amino acids (e.g., glutamic acids and aspartic acids), or derivatives thereof. Examples of anionic polypeptides include, but are not limited to, polyglutamic acid (PGA) (e.g., poly-gamma-glutamic acid), polyaspartic acid, and polycarboxyglutamic acid. In some embodiments, an anionic polypeptide is a PGA (e.g., poly-gamma-glutamic acid), such as a poly(L-glutamic) acid or a poly(D-glutamic) acid. An anionic polypeptide can contain a mixture of glutamic acids and aspartic acids. In some embodiments, at least 50% (e.g., 55%, 60%, 65%, 70%, 75%, 80%, 85%, 90%, 95%, or 100%) of the subunits or monomers in an anionic polypeptide can be glutamic acids and/or aspartic acids. An anionic polysaccharide is an anionic polymer that has at least 50% (e.g., 55%, 60%, 65%, 70%, 75%, 80%, 85%, 90%, 95%, or 100%) of its subunits or monomers being sugar molecules, such as monosaccharides (e.g., fructose, galactose, and glucose) and disaccharides (e.g., hyaluronic acid, lactose, maltose, and sucrose), or derivatives thereof. Examples of anionic polysaccharides include, but are not limited to, hyaluronic acid (HA), heparin, heparin sulfate, and glycosaminoglycan. In some embodiments, at least 50% (e.g., 55%, 60%, 65%, 70%, 75%, 80%, 85%, 90%, 95%, or 100%) of the subunits or monomers in an anionic polysaccharide can be HA. Other examples of anionic polymers include, but are not limited to, poly(acrylic acid) (PAA), poly(methacrylic acid) (PMAA), poly(styrene sulfonate), and polyphosphate.

An anionic polymer herein does not refer to a nucleic acid, such as a deoxyribonucleic acid (DNA), ribonucleic acid (RNA), that is composed entirely of nucleotides. In some embodiments, an anionic polymer can include one or more nucleobases (e.g., guanosine, cytidine, adenosine, thymidine, and uridine) together with other subunits or monomers, such as amino acids and/or small organic molecules (e.g., an organic acid). In some embodiments, at least 50% (e.g., 55%, 60%, 65%, 70%, 75%, 80%, 85%, 90%, 95%, or 100%) of the subunits or monomers in the anionic polymer are not nucleotides or do not contain nucleobases. An anionic polymer can contain at least two subunits or monomers (e.g., at least 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 subunits or monomers; between 100 and 400, between 120 and 400, between 140 and 400, between 160 and 400, between 180 and 400, between 200 and 400, between 220 and 400, between 240 and 400, between 260 and 400, between 280 and 400, between 300 and 400, between 320 and 400, between 340 and 400, between 360 and 400, between 380 and 400, between 100 and 380, between 100 and 360, between 100 and 340, between 100 and 320, between 100 and 300, between 100 and 280, between 100 and 260, between 100 and 240, between 100 and 220, between 100 and 200, between 100 and 180, between 100 and 160, between 100 and 140, or between 100 and 120 subunits or monomers). In some embodiments, the anionic polymer has a molecular weight of at least 3 kDa (e.g., 5, 10, 15, 20, 25, 30, 35, 40, 45, or 50 kDa). In some embodiments, the anionic polymer has a molecular weight of between 3 kDa and 50 kDa (e.g., between 3 kDa and 45 kDa, between 3 kDa and 40 kDa, between 3 kDa and 35 kDa, between 3 kDa and 30 kDa, between 3 kDa and 25 kDa, between 3 kDa and 20 kDa, between 3 kDa and 15 kDa, between 3 kDa and 10 kDa, between 3 kDa and 5 kDa, between 5 kDa and 50 kDa, between 10 kDa and 50 kDa, between 15 kDa and 50 kDa, between 20 kDa and 50 kDa, between 25 kDa and 50 kDa, between 30 kDa and 50 kDa, between 35 kDa and 50 kDa, between 40 kDa and 50 kDa, or between 45 kDa and 50 kDa). In some embodiments, the anionic polymer has a molecular weight of between 50 kDa and 150 kDa (e.g., between 50 kDa and 140 kDa, between 50 kDa and 130 kDa, between 50 kDa and 120 kDa, between 50 kDa and 110 kDa, between 50 kDa and 100 kDa, between 50 kDa and 90 kDa, between 50 kDa and 80 kDa, between 50 kDa and 70 kDa, between 50 kDa and 60 kDa, between 60 kDa and 150 kDa, between 70 kDa and 150 kDa, between 80 kDa and 150 kDa, between 90 kDa and 150 kDa, between 100 kDa and 150 kDa, between 110 kDa and 150 kDa, between 120 kDa and 150 kDa, between 130 kDa and 150 kDa, or between 140 kDa and 150 kDa). In some embodiments, the anionic polymer has a molecular weight of between 15 kDa and 50 kDa (e.g., between 15 kDa and 45 kDa, between 15 kDa and 40 kDa, between 15 kDa and 35 kDa, between 15 kDa and 30 kDa, between 15 kDa and 25 kDa, between 15 kDa and 20 kDa, between 20 kDa and 50 kDa, between 25 kDa and 50 kDa, between 30 kDa and 50 kDa, between 35 kDa and 50 kDa, between 40 kDa and 50 kDa, or between 45 kDa and 50 kDa). In some embodiments, a composition described herein has a molar ratio of anionic polymer:targetable nuclease at between 10:1 and 120:1, e.g., 10:1, 20:1, 30:1, 40:1, 50:1, 60:1, 70:1, 80:1, 90:1, 100:1, 110:1, or, 120:1; between 10:1 and 110:1, between 10:1 and 100:1, between 10:1 and 90:1, between 10:1 and 80:1, between 10:1 and 70:1, between 10:1 and 60:1, between 10:1 and 50:1, between 10:1 and 40:1, between 10:1 and 30:1, between 10:1 and 20:1, between 20:1 and 120:1, between 30:1 and 120:1, between 40:1 and 120:1, between 50:1 and 120:1, between 60:1 and 120:1, between 70:1 and 120:1, between 80:1 and 120:1, between 90:1 and 120:1, between 100:1 and 120:1, or between 110:1 and 120:1.

X. Gene Targeting Nucleic Acids in Cells

The compositions described herein can be used in methods of modifying a target nucleic acid in a cell, e.g., an eukaryotic cells, prokaryotic cell, animal cell, plant cell, fungal cell, and the like. Optionally, the cell is a mammalian cell, for example, a human cell. The cell can be in vitro, ex vivo, or in vivo. The cell can also be a primary cell, a germ cell, a stem cell, or a precursor cell. The precursor cell can be, for example, a pluripotent stem cell, or a hematopoietic stem cell. In some embodiments, the cell is a primary hematopoietic cell, a primary hematopoietic stem cell, or a primary T cell. In some embodiments, the primary hematopoietic cell is an immune cell. In some embodiments, the immune cell is a T cell. In some embodiments, the T cell is a regulatory T cell, an effector T cell, or a naïve T cell. In some embodiments, the T cell is a $CD4^+$ T cell. In some embodiments, the T cell is a $CD8^+$ T cell. In some embodiments, the T cell is a $CD4^+CD8^+$ T cell. In some embodiments, the T cell is a $CD4^-CD8^-$ T cell. In some embodiments the T cell is an αβ T cell, in some embodiments the T cell is a γδ T cell. Populations of any of the cells modified by any of the methods described herein are also provided. In some embodiments, the methods further comprise expanding the population of modified cells.

The donor constructs described herein can be used in methods for identifying a targeted insertion in the genome of a cell (e.g., as described in Roth et al., (2019). Rapid discovery of synthetic DNA sequences to rewrite endogenous T cell circuits. *BioRxiv* 10.1101/604561. For example, a library of the same type of donor constructs (e.g., a donor construct as shown in FIG. 1) can be made, in which each donor construct has a distinct HDRT. Optionally, each donor construct in the library can include a unique barcode nucleotide sequence which indicates the identity of the specific HDRT in the donor construct. The methods provide a targeted nuclease (e.g., Cas9) that cleaves a target region in the genome of the cell to create a target insertion site; a library of donor constructs each having a distinct HDRT; a donor gRNA that hybridizes to the DNA-binding protein target sequence within the donor construct; and a DNA-binding target protein that recognizes and brings the donor construct to the target insertion site. The library of donor constructs includes two or more donor constructs that differ by their HDRT sequences. In certain embodiments, the library of donor constructs includes at least 10, 20, 30, 40, 50. 60, 70, 80, 90, or 100 donor constructs that differ by their HDRT sequences. After recombination occurs and a population of modified cells is created, DNA can be amplified from the modified cells using primers. Subsequently, the DNA can be sequenced to identify the template that is inserted into the target insertion site of the cell. In some embodiments, the methods can include determining the relative number of cells in the population having different templates inserted in the target insertion site.

In a particular aspect, a population of cells (e.g., a population of T cells), is provided. The population of cells can comprise any of the modified cells described herein. The modified cell can be within a heterogeneous population of cells and/or a heterogeneous population of different cell types. The population of cells can be heterogeneous with respect to the percentage of cells that are genomically edited. A population of cells can have greater than 10%, greater than 20%, greater than 30%, greater than 40%, greater than 50%, greater than 60%, greater than 70%, greater than 80%, or greater than 90% of the population comprise an integrated nucleotide sequence. In a certain aspect, a populations of cells comprises an integrated nucleotide sequence, wherein the integrated nucleotide sequence comprises at least a portion of a gene, the integrated nucleotide sequence is integrated at an endogenous genomic target locus, and the integrated nucleotide sequence is orientated such that the at least a portion of the gene is capable of being expressed, wherein the population of cells is substantially free of viral-mediated delivery components, and wherein greater than 10%, greater than 20%, greater than 30%, greater than 40%, greater than 50%, greater than 60%, greater than 70%, greater than 80%, or greater than 90% of the cells in the population comprise the integrated nucleotide sequence.

Methods for modifying a target nucleic acid in a cell described herein comprise introducing into the cell a composition described herein, wherein the HDRT is integrated into the target nucleic acid. In some embodiments, a composition described herein is introduced into the cell via electroporation. In some cases, the cells are removed from a subject, modified using any of the methods described herein and administered to the subject. In other cases, a composition described herein can be delivered to the subject in vivo. See, for example, U.S. Pat. No. 9,737,604 and Zhang et al. "Lipid nanoparticle-mediated efficient delivery of CRISPR/Cas9 for tumor therapy," *NPG Asia Materials* Volume 9, page e441 (2017).

In some embodiments, the cell is a primary cell that is selected from the group consisting of an immune cell (e.g., a primary T cell), a blood cell, a progenitor or stem cell thereof, a mesenchymal cell, and a combination thereof. In some instances, the immune cell is selected from the group consisting of a T cell, a B cell, a dendritic cell, a natural killer cell, a macrophage, a neutrophil, an eosinophil, a basophil, a mast cell, a precursor thereof, and a combination thereof. The progenitor or stem cell can be selected from the group consisting of a hematopoietic progenitor cell, a hematopoietic stem cell, and a combination thereof. In some cases, the blood cell is a blood stem cell. In some instances, the mesenchymal cell is selected from the group consisting of a mesenchymal stem cell, a mesenchymal progenitor cell, a mesenchymal precursor cell, a differentiated mesenchymal cell, and a combination thereof. The differentiated mesenchymal cell can be selected from the group consisting of a bone cell, a cartilage cell, a muscle cell, an adipose cell, a stromal cell, a fibroblast, a dermal cell, and a combination thereof. In some embodiments, the primary cell can comprise a population of primary cells. In some cases, the population of primary cells comprises a heterogeneous population of primary cells. In other cases, the population of primary cells comprises a homogeneous population of primary cells.

A composition described herein can be introduced into a cell (e.g., a primary cell) using available methods and techniques in the art. Non-limiting examples of suitable methods include electroporation, particle gun technology, and direct microinjection. In some embodiments, the step of introducing the composition described herein into the cell comprises electroporating the composition into the cell.

Publications cited herein and the material for which they are cited are hereby specifically incorporated by reference in their entireties.

EXAMPLES

The following examples are provided by way of illustration only and not by way of limitation. Those of skill in the art will readily recognize a variety of non-critical parameters that could be changed or modified to yield essentially the same or similar results.

Example 1—Donor Construct Generation

Generation of short HDRTs (e.g., less than 200 bp) can be performed de novo. To generate long ssDNA, we first created a dsDNA version of the HDRT, which was then amplified by PCR using long primers which incorporate the additional 5' and 3' segments. One of the two PCR primers was biotinylated, leading to one strand of the final PCR product with 5'-biotinylation. The product was bound to streptavidin-coupled magnetic beads and denatured in basic solution to release the non-biotinylated strand (FIG. 2A). This process was highly consistent and gave excellent purity without degrading the 5' or 3' ends, in contrast to enzymatic approaches. To generate the final construct, the product was mixed with complementary 5' and 3' oligos (for example, in the case of the "primer" donor construct) or simply annealed (for example, in the case of the"hairpin" donor construct.

Example 2—Knock-In Efficiency at Different Amounts of Constructs

Initial tests with the constructs indicated that all designs substantially increased knock-in efficiency at low concentrations (FIG. 3). However, at the highest amount of 100 pmol, these benefits disappeared, suggesting the maximum knock-in efficiency has been reached.

Example 3—Knock-In Efficiency at Different Amounts of Primer Donor Constructs

To test effects on long HDRT, primer donor constructs ("ssDNA+shuttle" in FIGS. 4A-4C) were generated as described above to knock-in an HA tag to the CD5 locus. These were compared against dsDNA, dsDNA with shuttle ends, and ssDNA. Both the dsDNA+shuttle and the ssDNA+shuttle increased knock-in efficiency at low concentrations (FIG. 4A, ≤0.1 pmol). However, the dsDNA+shuttle significantly increased cellular toxicity at higher concentrations (FIG. 4B, ≥0.5 pmol) with concomitant loss of benefit toward knock-in efficiency. The ssDNA+shuttle demonstrated significantly lower toxicity and was able to reach higher concentration and higher knock-in efficiency without killing the cells (FIG. 4B). This resulted in a substantially higher total knock-in count (FIG. 4C).

To demonstrate this effect for other more therapeutically relevant knock-ins, we generated other constructs targeting a CD25-GFP cDNA knock-in to the IL2RA locus (FIGS. 5A-5C) or targeting an NY-ESO-1 specific T cell receptor to the endogenous TRAC locus (FIGS. 6A-6C). Both generated substantially higher knock-in efficiencies, lower toxicity, and higher total knock-in count using the ssDNA+shuttle ("primer") construct.

Example 4—Methods

Isolation of Human Primary T Cells for Gene Targeting

Primary human T cells were isolated from healthy human donors either from fresh whole blood, residuals from leukoreduction chambers after TRIMA® Apheresis (BLOOD CENTERS OF THE PACIFIC™), or leukapheresis products (STEMCELL™). Peripheral blood mononuclear cells (PBMCs) were isolated from whole blood samples by FICOLL centrifugation using SEPMATE™ tubes (STEMCELL™, per manufacturer's instructions). T cells were isolated from PBMCs from all cell sources by magnetic negative selection using an EASYSEP™ Human T Cell Isolation Kit (STEMCELL™, per manufacturer's instructions).

Primary Human T Cell Culture

Bulk T cells were cultured in X-VIVO15 medium (STEMCELL™) with 5% fetal bovine serum (FBS), 50 μM 2-mercaptoethanol, and 10 μM N-acetyl L-cystine. Immediately after isolation, T cells were stimulated for 2 days with anti-human CD3/CD28 magnetic DYNABEADS™ (THERMOFISHER®) at a beads to cells concentration of 1:1, along with a cytokine cocktail of IL-2 at 200 U/ml (UCSF Pharmacy), IL-7 at 5 ng/ml (THERMOFISHER®), and IL-15 at 5 ng/ml (LIFE TECHOLOGIES®). After electroporation, T cells were cultured in media with IL-2 at 500 U/ml. Throughout the culture period T cells were maintained at an approximate density of 1 million cells per ml of media. Every 2-3 days after electroporation, additional media was added, along with additional fresh IL-2 to bring the final concentration to 500 U/ml, and cells were transferred to larger culture vessels as necessary to maintain a density of 1 million cells per ml.

RNP Production

RNPs were produced by complexing a two-component gRNA to Cas9. In brief, crRNAs and tracrRNAs were chemically synthesized (DHARMACON™, IDT™), and recombinant Cas9-NLS, D10A-NLS, or dCas9-NLS were recombinantly produced and purified (QB3 Macrolab). Lyophilized RNA was resuspended in 10 mM Tris-HCL (7.4 pH) with 150 mM KCl at a concentration of 160 μM, and stored in aliquots at −80° C. crRNA and tracrRNA aliquots were thawed, mixed 1:1 by volume, and annealed by incubation at 37° C. for 30 min to form an 80 μM gRNA solution. Recombinant Cas9 or the D10A Cas9 variant were stored at 40 μM in 20 mM HEPES-KOH, pH 7.5, 150 mM KCl, 10% glycerol, 1 mM DTT, were then mixed 1:1 by volume with the 80 μM gRNA (2:1 gRNA to Cas9 molar ratio) at 37° C. for 15 min to form an RNP at 20 μM. RNPs were electroporated immediately after complexing.

Double-Stranded DNA HDRT Production

Novel HDR sequences were constructed using Gibson Assemblies to insert the HDR template sequence, consisting of the homology arms (commonly synthesized as GBLOCKs™ from IDT™) and the desired insert (such as GFP) into a cloning vector for sequence confirmation and future propagation. These plasmids were used as templates for high-output PCR amplification (KAPA™ Hotstart polymerase). PCR amplicons (the dsDNA HDRT) were SPRI purified (1.0×) and eluted into a final volume of 3 μl H20 per 100 μl of PCR reaction input. Concentrations of HDRTs were determined by NANODROP™ using a 1:20 dilution. The size of the amplified HDRT was confirmed by gel electrophoresis in a 1.0% agarose gel.

Single-Stranded DNA (ssDNA) HDRT and ssDNA Shuttle HDRT Production ssDNA HDRT are prepared by PCR as described for dsDNA HDRT but with the inclusion of a 5' biotin modification on the reverse primer. The PCR product is then incubated with streptavidin coupled magnetic beads (DYNABEADS™ Strepatavidin MYONE™ C1 #65001) to bind the biotinylated strand. The dsDNA is then denatured in the presence of 125 mM NaOH. The supernatant containing the non-biotinylated strand is collected, purified, and concentrated using SPRI bead cleanup as described above.

To produce a ssDNA shuttle HDRT, the ssDNA HDRT is then incubated with a 6-fold molar excess of oligos complementary to the 5' and 3' ends. The mixture is brought to 95° C. and slowly cooled to room temperature over the course of ~1 hour to allow efficient annealing.

Primary T Cell Electroporation

RNPs and HDR templates were electroporated 2 days after initial T cell stimulation. T cells were collected from their culture vessels and magnetic anti-CD3/anti-CD28 DYNABEADS™ were removed by placing cells on an EASYSEP™ cell separation magnet for 2 min. Immediately before electroporation, de-beaded cells were centrifuged for 10 min at 90 g, aspirated, and resuspended in the LONZA® electroporation buffer P3 using 20 μl buffer per 1 million cells. For optimal editing, 1 million T cells were electroporated per well using a LONZA® 4D-NUCLEOFECTOR® 96-well electroporation system with pulse code EH115.

Flow Cytometry and Cell Sorting

Flow cytometric analysis was performed on an ATTUNE™ N×T Acoustic Focusing Cytometer (THERMO FISHER®) or an LSRII flow cytometer (BD®). FACS was performed on the FACSARIA™ platform (BD®). Surface staining for flow cytometry and cell sorting was performed by pelleting cells and resuspending in 25 μl of FACS buffer (2% FBS in PBS) with antibodies at the various concentrations for 20 min at 4° C. in the dark. Cells were washed once in FACS buffer before resuspension.

Example 5—Primary Human T Cell Knock-In with Large Primer Donor Constructs

This example demonstrated and compared the knock-in efficiencies of large primer donor constructs ("ssDNA+shuttle") of varying sizes with dsDNA, dsDNA with shuttle ends, and unmodified ssDNA. The constructs used here were CD5-HA HDRT, IL2RA-tNGFR HDRT, and IL2RA-CD25-GFP HDRT. Representative flow plots are shown in FIGS. 7A-7F for untreated controls and knock-in populations. Knock-in efficiency, live cell counts, and absolute number of knock-in cells are shown in FIGS. 8A-8I with increasing concentration of HDRT. The ssDNA shuttle versions showed increased knock-in efficiency, lower toxicity, and increased numbers of knock-in cells in comparison to all other variants. Sequences used in this example are shown in SEQ ID NOS:36-43.

Example 6—Shuttle Design and Mechanistic Studies

This experiment examined CD5-HA and CD25-GFP primer donor constructs ("ssDNA+shuttle") to identify design principles and mechanism of benefit.

ssDNA shuttle ends were altered to identify sequence requirements. ssDNA shuttle with sequence complementary to the corresponding gRNA increased knock-in efficiency in comparison to ssDNA control. All other variations showed no benefit including an equivalent length of dsDNA protecting the homology arm ends ("end protection"), mismatched shuttle sequence from the other HDRT, and an equivalent length of scrambled dsDNA (FIGS. 9A and 9B). Sequences used in this experiment were shown in Table 1 below.

TABLE 1

| Base HDRT | Variant name | Side | Shuttle sequence | SEQ ID NO |
|---|---|---|---|---|
| CD5-HA | ssDNA shuttle | 5' | AACAAGCAGCGCTT CCTGCCTCGGACGG | 44 |
| CD5-HA | ssDNA shuttle | 3' | TTGTTGCAGCGCTT CCTGCCTCGGACGG | 45 |
| CD5-HA | mismatch shuttle | 5' | TGGCGACTCCAGTC CCCACATCAGCCGG | 46 |
| CD5-HA | mismatch shuttle | 3' | CACCACATACAGTC CCCACATCAGCCGG | 47 |
| CD5-HA | Scramble no PAM | 5' | AACAAGTCAGCGAA CGACAGAGCGTCTT | 48 |
| CD5-HA | Scramble no PAM | 3' | TTGTTGTCAGCGAA CGACAGAGCGTCTT | 49 |
| CD25-GFP | Shuttle G377 IL2RAe1 | 5' | TGGCGACTCCAGTC CCCACATCAGCCGG | 50 |
| CD25-GFP | Shuttle G377 IL2RAe1 | 3' | CACCACATACAGTC CCCACATCAGCCGG | 51 |
| CD25-GFP | Shuttle G472 IL2RAe1 | 5' | AACAAGCAGCGCTT CCTGCCTCGGACGG | 52 |
| CD25-GFP | Shuttle G472 IL2RAe1 | 3' | TTGTTGCAGCGCTT CCTGCCTCGGACGG | 53 |
| CD25-GFP | Shuttle ScrNoPAM IL2RAe1 | 5' | AACAAGTCAGCGAA CGACAGAGCGTCTT | 54 |
| CD25-GFP | Shuttle ScrNoPAM IL2RAe1 | 3' | TTGTTGTCAGCGAA CGACAGAGCGTCTT | 55 |

ssDNA shuttle HDRTs with variations on the 20 bp gRNA sequence complementary were shown in comparison to a ssDNA control. Each variant contained a different number of mismatched bases to alter gRNA binding affinity so that Cas9 RNPs can bind without cutting the shuttle sequence. Variants with 2-8 bp mismatch demonstrated highest increase in knock-in efficiency. Two different Cas9 species (WT and SpyFi) showed a similar response (FIGS. 9C and 9D). Sequences used in this experiment were shown in Table 2 below.

TABLE 2

| Base HDRT | mis-match # | 5' Reverse Complement | SEQ ID NO | 3' Reverse Complement | SEQ ID NO |
|---|---|---|---|---|---|
| CD5-HA | 0 | CTTGAACCTGGGAGGTGGAGCC GTCCGAGGCAGGAAGCGACTGT TGTT | 56 | ttgttCAGTCGCTTCCTGCC TCGGACGGgcataaagagctcct tgaag | 57 |
| CD5-HA | 2 | CTTGAACCTGGGAGGTGGAGCC GTCCGAGGCAGGAAGCGACAC TTGTT | 58 | ttgttGTGTCGCTTCCTGCC TCGGACGGgcataaagagctcct tgaag | 59 |

TABLE 2-continued

| Base HDRT | mis-match # | 5' Reverse Complement | SEQ ID NO | 3' Reverse Complement | SEQ ID NO |
|---|---|---|---|---|---|
| CD5-HA | 4 | CTTGAACCTGGGAGGTGGAGCCGTCCGAGGCAGGAAGCGTGACTTGTT | 60 | ttgttGTCACGCTTCCTGCCTCGGACGGgcataaagagctccttgaag | 61 |
| CD5-HA | 6 | CTTGAACCTGGGAGGTGGAGCCGTCCGAGGCAGGAAGGCTGACTTGTT | 62 | ttgttGTCAGCCTTCCTGCCTCGGACGGgcataaagagctccttgaag | 63 |
| CD5-HA | 8 | CTTGAACCTGGGAGGTGGAGCCGTCCGAGGCAGGATCGCTGACTTGTT | 64 | ttgttGTCAGCGATCCTGCCTCGGACGGgcataaagagctccttgaag | 65 |
| CD5-HA | 12 | CTTGAACCTGGGAGGTGGAGCCGTCCGAGGCTCCTTCGCTGACTTGTT | 66 | ttgttGTCAGCGAAGGAGCCTCGGACGGgcataaagagctccttgaag | 67 |
| CD5-HA | 16 | CTTGAACCTGGGAGGTGGAGCCGTCCGTCCGTCCTTCGCTGACTTGTT | 68 | ttgttGTCAGCGAAGGACGGACGGACGGgcataaagagctccttgaag | 69 |
| CD5-HA | 20 | CTTGAACCTGGGAGGTGGAGCCGAGGCTCCGTCCTTCGCTGACTTGTT | 70 | ttgttGTCAGCGAAGGACGGAGCCTCGGgcataaagagctccttgaag | 71 |
| CD25-GFP | 0 | GCACTCTCTTCTCTCATCTCCCGGCTGATGTGGGGACTGCTCACGCCA | 72 | caccaTGAGCAGTCCCCACATCAGCCGGtgagaaacctgctcatcggg | 73 |
| CD25-GFP | 2 | GCACTCTCTTCTCTCATCTCCCGGCTGATGTGGGGACTGCTGTCGCCA | 74 | caccaACAGCAGTCCCCACATCAGCCGGtgagaaacctgctcatcggg | 75 |
| CD25-GFP | 4 | GCACTCTCTTCTCTCATCTCCCGGCTGATGTGGGGACTGGAGTCGCCA | 76 | caccaACTCCAGTCCCCACATCAGCCGGtgagaaacctgctcatcggg | 77 |
| CD25-GFP | 6 | GCACTCTCTTCTCTCATCTCCCGGCTGATGTGGGGACACGAGTCGCCA | 78 | caccaACTCGTGTCCCCACATCAGCCGGtgagaaacctgctcatcggg | 79 |
| CD25-GFP | 8 | GCACTCTCTTCTCTCATCTCCCGGCTGATGTGGGGTGACGAGTCGCCA | 80 | caccaACTCGTCACCCCACATCAGCCGGtgagaaacctgctcatcggg | 81 |
| CD25-GFP | 12 | GCACTCTCTTCTCTCATCTCCCGGCTGATGTCCCCTGACGAGTCGCCA | 82 | caccaACTCGTCAGGGGACATCAGCCGGtgagaaacctgctcatcggg | 83 |
| CD25-GFP | 16 | GCACTCTCTTCTCTCATCTCCCGGCTGTACACCCCTGACGAGTCGCCA | 84 | caccaACTCGTCAGGGGTGTACAGCCGGtgagaaacctgctcatcggg | 85 |
| CD25-GFP | 20 | GCACTCTCTTCTCTCATCTCCCGCGACTACACCCCTGACGAGTCGCCA | 86 | caccaACTCGTCAGGGGTGTAGTCGCGGtgagaaacctgctcatcggg | 87 |

ssDNA with dsDNA ends covering different segments of the shuttle sequence and flanking homology arms were compared. The increase in knock-in efficiency required dsDNA covering the gRNA sequence, PAM sequence, and a segment of the homology arm. Variants without dsDNA covering these 3 components showed no benefit. The shuttle sequence was only beneficial on the 5' end, with no effect on the 3' end (red), and no additional benefit for the combination of both 5' and 3' ends (FIGS. 9E and 9F). Sequences used in this experiment were shown in Table 3 below.

TABLE 3

| Base HDRT | 5'/3' end | rC overlap? 5' Buffer | gRNA | PAM | HA | RC Seq | Length | SEQ ID NO |
|---|---|---|---|---|---|---|---|---|
| CD5-HA base HDRT | 5 | 1* | 1 | 1 | 1 | cttgaacctgggaggtggagCCGTCCGAGGCAGGAAGCGCTGCTTGTT | 48 | 88 |

TABLE 3-continued

| Base HDRT | 5'/ 3' end | rC overlap? 5' Buffer | gRNA | PAM | HA | RC Seq | Length | SEQ ID NO |
|---|---|---|---|---|---|---|---|---|
| CD5-HA base HDRT | 5 | 1 | 1 | 1 | 0 | CCGTCCGAGGCAGGAAG CGCTGCTTGTT | 28 | 89 |
| CD5-HA base HDRT | 5 | 1 | 1 | 0* | 0 | TCCGAGGCAGGAAGCGC TGCTTGTT | 25 | 90 |
| CD5-HA base HDRT | 5 | 0 | 1 | 0 | 0 | TCCGAGGCAGGAAGCGC TGC | 20 | 91 |
| CD5-HA base HDRT | 5 | 0 | 1 | 1 | 1 | cttgaacctgggaggtg gagCCGTCCGAGGCAGG AAGCGCTGC | 43 | 92 |
| CD5-HA base HDRT | 5 | 0 | 0 | 1 | 1 | cttgaacctgggaggtg gagCCG | 23 | 93 |
| CD5-HA base HDRT | 5 | 0 | 1 | 1 | 0 | CCGTCCGAGGCAGGAAG CGCTGC | 23 | 94 |
| CD5-HA base HDRT | 5 | 0 | 0 | 0 | 1 | cttgaacctgggaggtg gag | 20 | 95 |
| CD5-HA base HDRT | 3 | 1 | 1 | 1 | 1 | TTGTTGCAGCGCTTCCTG CCTCGGACGGGCATAAA GAGCTCCTTGAAG | 48 | 96 |
| CD5-HA base HDRT | 3 | 1 | 1 | 1 | 0 | TTGTTGCAGCGCTTCCTG CCTCGGACGG | 28 | 97 |
| CD5-HA base HDRT | 3 | 1 | 1 | 0 | 0 | TTGTTGCAGCGCTTCCTG CCTCGGA | 25 | 98 |
| CD5-HA base HDRT | 3 | 0 | 1 | 0 | 0 | GCAGCGCTTCCTGCCTC GGA | 20 | 99 |
| CD5-HA base HDRT | 3 | 0 | 1 | 1 | 1 | GCAGCGCTTCCTGCCTC GGACGGGCATAAAGAG CTCCTTGAAG | 43 | 100 |
| CD5-HA base HDRT | 3 | 0 | 0 | 1 | 1 | CGGGCATAAAGAGCTCC TTGAAG | 23 | 101 |
| CD5-HA base HDRT | 3 | 0 | 1 | 1 | 0 | GCAGCGCTTCCTGCCTC GGACGG | 23 | 102 |
| CD5-HA base HDRT | 3 | 0 | 0 | 0 | 1 | GCATAAAGAGCTCCTTG AAG | 20 | 103 |
| IL2RA-CD25-GFP base HDRT | 5 | 1 | 1 | 1 | 1 | GCACTCTCTTCTCTCATC TCCCGGCTGATGTGGGG ACTGGAGTCGCCA | 48 | 104 |
| IL2RA-CD25-GFP base HDRT | 5 | 1 | 1 | 1 | 0 | CCGGCTGATGTGGGGAC TGGAGTCGCCA | 28 | 105 |
| IL2RA-CD25-GFP base HDRT | 5 | 1 | 1 | 0 | 0 | GCTGATGTGGGGACTGG AGTCGCCA | 25 | 106 |
| IL2RA-CD25-GFP base HDRT | 5 | 0 | 1 | 0 | 0 | GCTGATGTGGGGACTGG AGT | 20 | 107 |
| IL2RA-CD25-GFP base HDRT | 5 | 0 | 1 | 1 | 1 | GCACTCTCTTCTCTCATC TCCCGGCTGATGTGGGG ACTGGAGT | 43 | 108 |
| IL2RA-CD25-GFP base HDRT | 5 | 0 | 0 | 1 | 1 | GCACTCTCTTCTCTCATC TCCCG | 23 | 109 |
| IL2RA-CD25-GFP base HDRT | 5 | 0 | 1 | 1 | 0 | CCGGCTGATGTGGGGAC TGGAGT | 23 | 110 |

TABLE 3-continued

| Base HDRT | 5'/ 3' end | rC overlap? 5' Buffer | gRNA | PAM | HA | RC Seq | Length | SEQ ID NO |
|---|---|---|---|---|---|---|---|---|
| IL2RA-CD25-GFP base HDRT | 5 | 0 | 0 | 0 | 1 | GAGATGAGAGAAGAGAGTGC | 20 | 111 |
| IL2RA-CD25-GFP base HDRT | 3 | 1 | 1 | 1 | 1 | CACCACATACAGTCCCCACATCAGCCGGTGAGAAACCTGCTCATCGGG | 48 | 112 |
| IL2RA-CD25-GFP base HDRT | 3 | 1 | 1 | 1 | 0 | CACCACATACAGTCCCCACATCAGCCGG | 28 | 113 |
| IL2RA-CD25-GFP base HDRT | 3 | 1 | 1 | 0 | 0 | CACCACATACAGTCCCCACATCAGC | 25 | 114 |
| IL2RA-CD25-GFP base HDRT | 3 | 0 | 1 | 0 | 0 | CATACAGTCCCCACATCAGC | 20 | 115 |
| IL2RA-CD25-GFP base HDRT | 3 | 0 | 1 | 1 | 1 | CATACAGTCCCCACATCAGCCGGTGAGAAACCTGCTCATCGGG | 43 | 116 |
| IL2RA-CD25-GFP base HDRT | 3 | 0 | 0 | 1 | 1 | CGGTGAGAAACCTGCTCATCGGG | 23 | 117 |
| IL2RA-CD25-GFP base HDRT | 3 | 0 | 1 | 1 | 0 | CATACAGTCCCCACATCAGCCGG | 23 | 118 |
| IL2RA-CD25-GFP base HDRT | 3 | 0 | 0 | 0 | 1 | TGAGAAACCTGCTCATCGGG | 20 | 119 |

*1: yes;
0: no.

ssDNA with dsDNA shuttle ends including the gRNA sequence, PAM sequence, and varied amount of overlap with the flanking 5' homology arm were tested and compared. Increasing knock-in efficiency was seen with more homology arm overlap up to a maximum of ~20 bp (FIGS. 9G and 9H).

Cas9 variants with a Nuclear Localization Sequence (NLS) provided additional improvements to knock-in efficiency, suggesting protein modifications can further enhance the ssDNA shuttle effects (FIGS. 9I and 9J).

Anionic polymers such as poly-glutamic acid (PGA) showed additional reduction of toxicity in combination with ssDNA shuttle sequences (FIGS. 9K and 9L).

Example 7—ssDNA Shuttle Technology is Applicable to a Wide Variety of Target Sites HDRTs and corresponding RNP were generated for 22 target sites in the human genome and used to knock-in a detectable surface marker in primary human T cells from 2 donors. Primer donor constructs ("ssDNA+shuttle") demonstrated increased knock-in efficiency and absolute count of knock-in cells (FIGS. 10A and 10C).

Figure 11A:
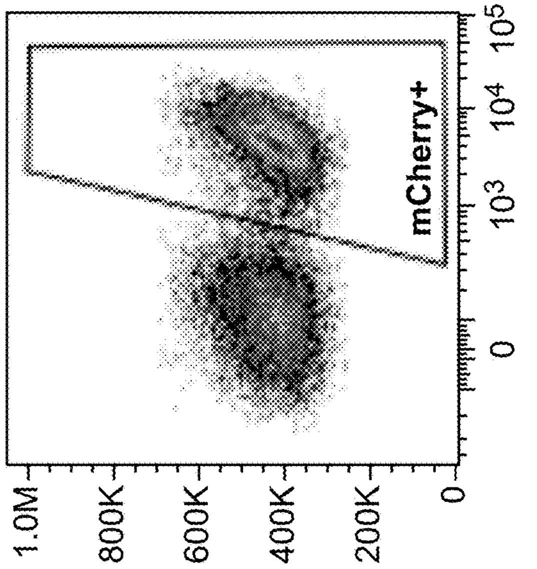
Figure 11B:
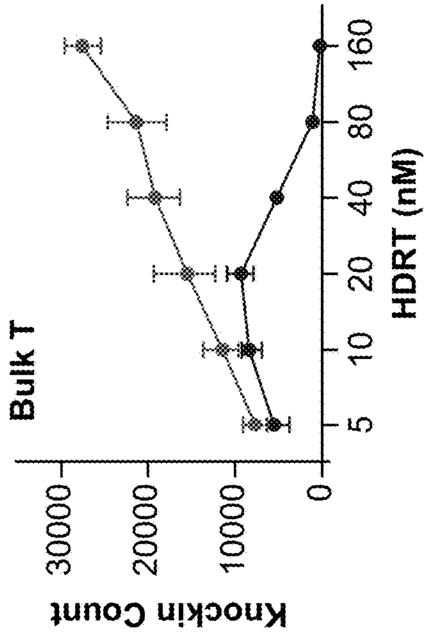
Figure 11C:
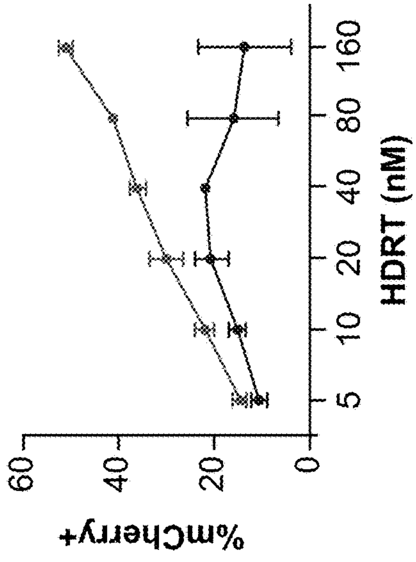
Figure 11D:
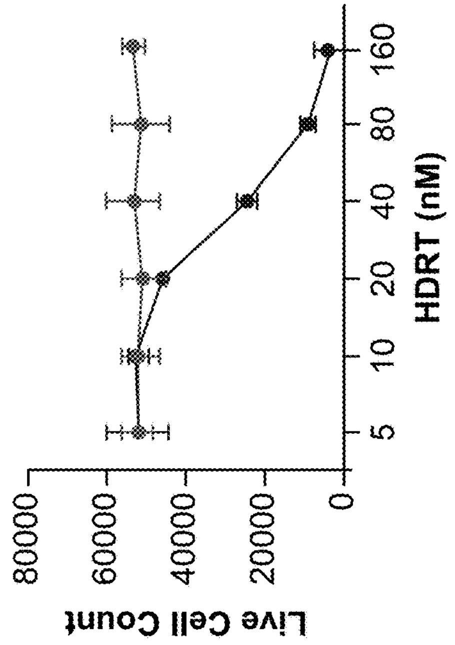
Figure 11E:
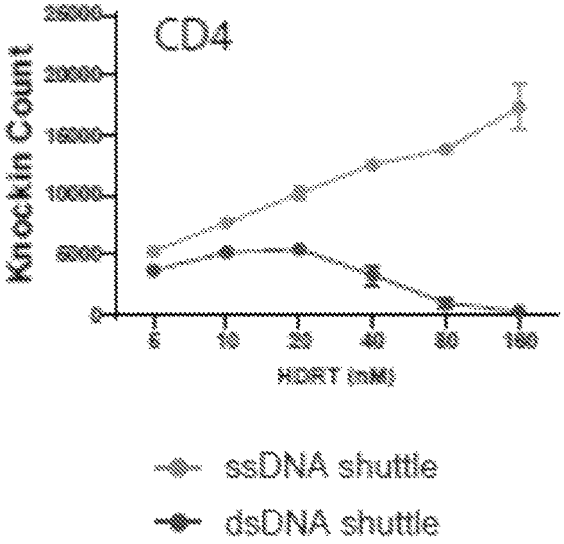
Figure 11F:
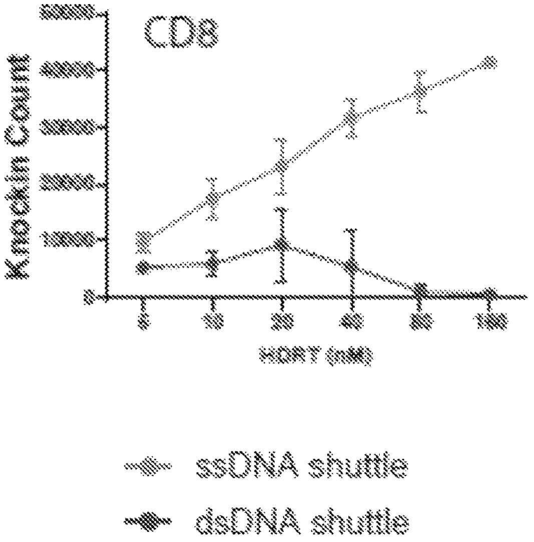
Figure 11G:
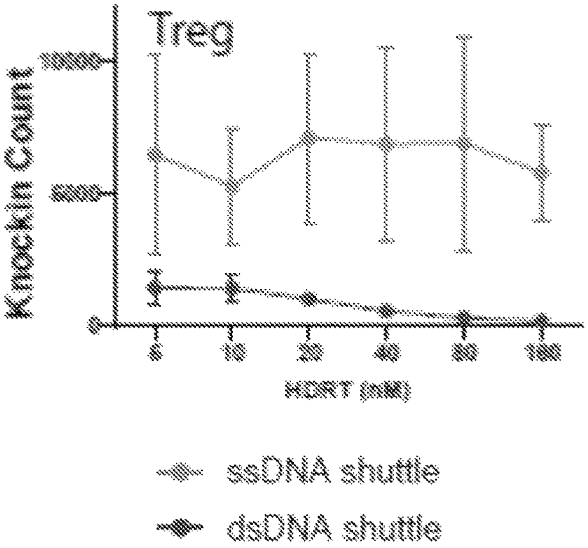
Figure 11H:
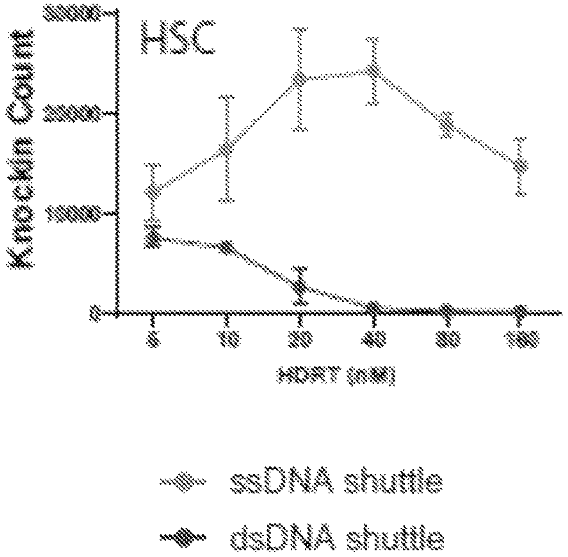
Figure 11I:
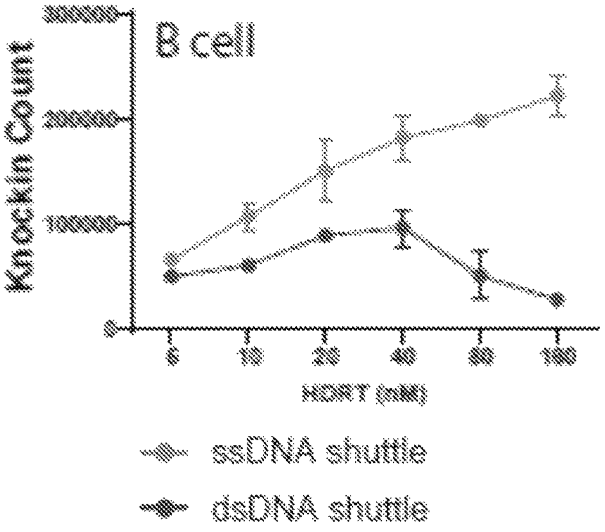
Figure 11J:
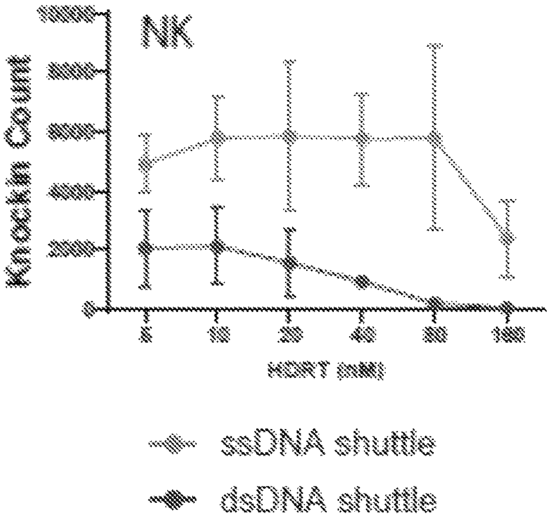
Figure 11K:
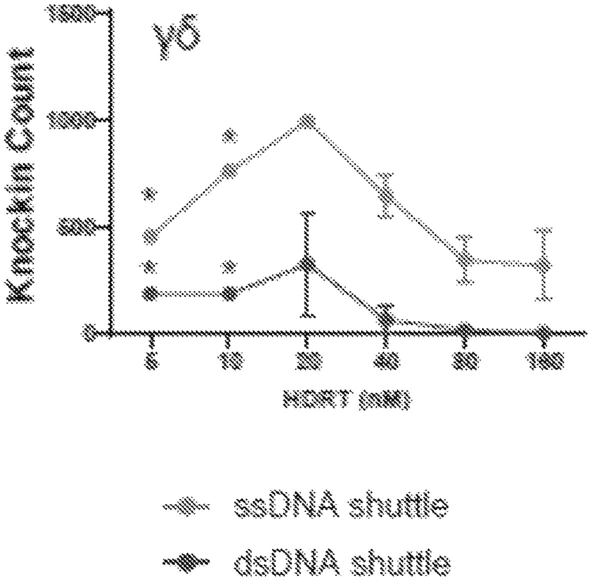
Figure 11L:
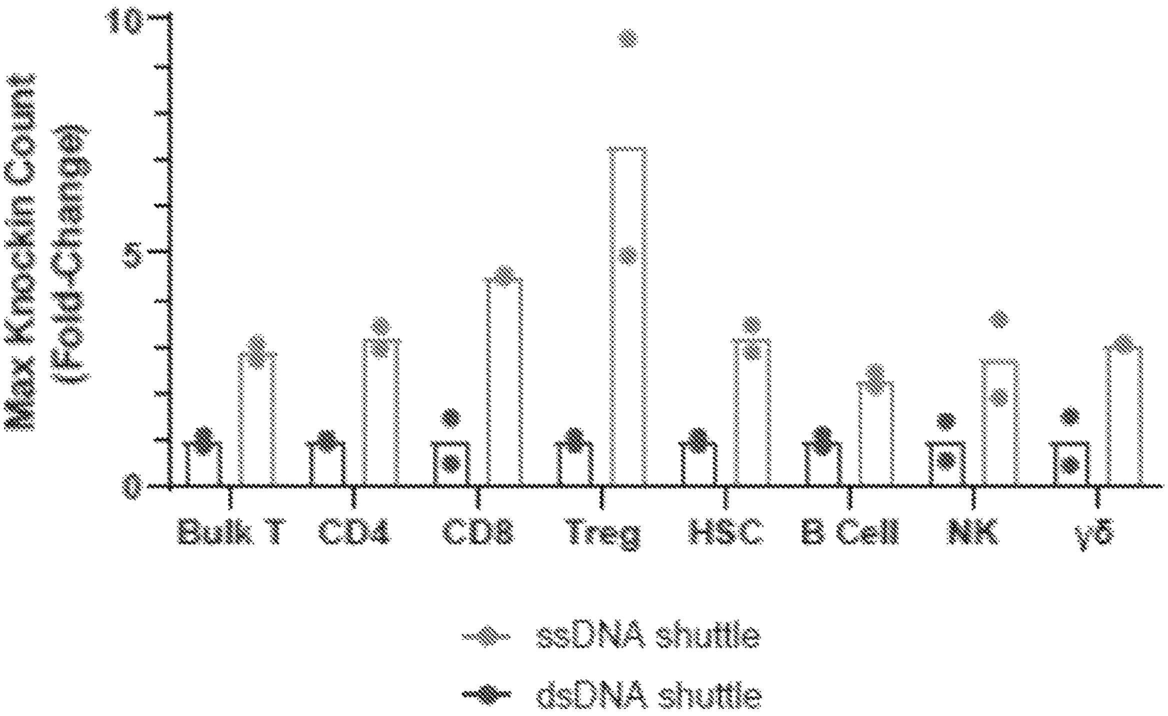
Figure 11M:
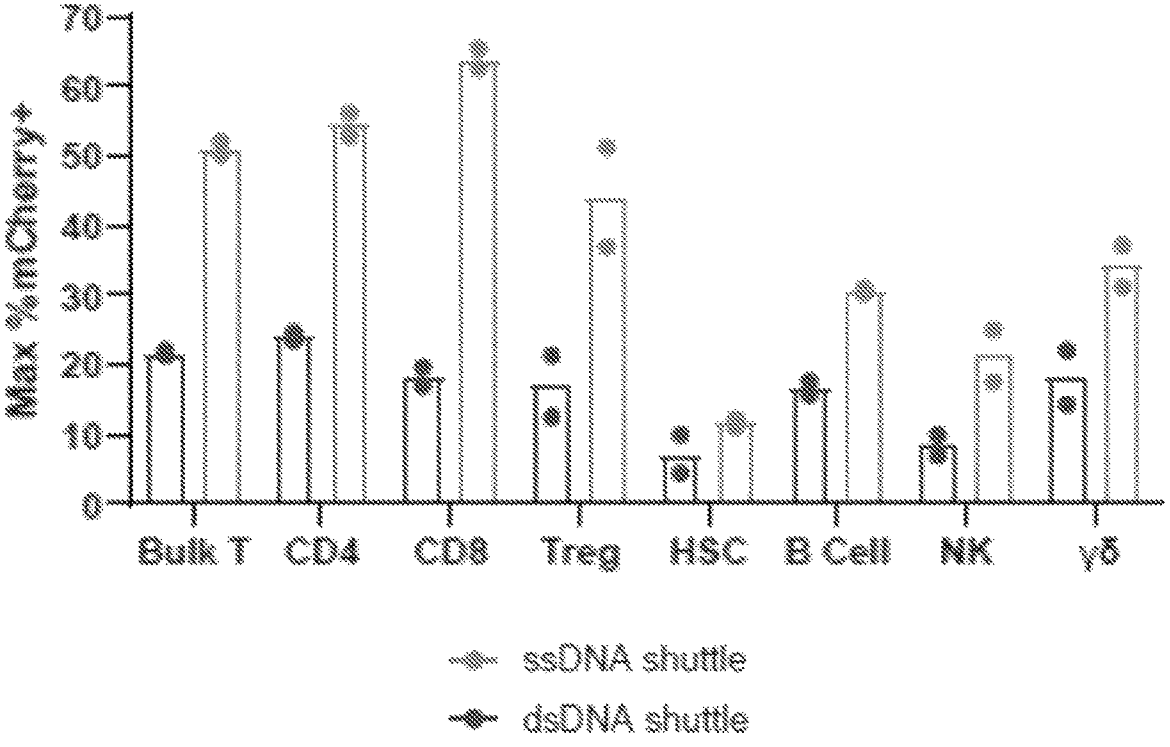

Example 8—ssDNA Shuttle Technology is Applicable to a Wide Variety of Primary Human Cell Types Primer donor constructs ("ssDNA+shuttle") and dsDNA shuttle were generated to knock-in a fluorescent mCherry marker within the Clathrin gene. mCherry+cells were gated as shown in the flow plot in FIG. 11A. Absolute knock-in count, knock-in efficiency, and total cell counts were compared over a range of HDRT concentrations in primary human bulk T cells (FIGS. 11B-11D), and a variety of other primary human cell types including CD4+ T cells (FIG. 11E), CD8+ T cells (FIG. 11F), regulatory T cells (Treg) (FIG. 11G), CD34+ hematopoietic stem cells (HSCs) (FIG. 11H), B cells (FIG. 11I), NK cells (FIG. 11J), and Gammadelta T cells ($\gamma\bar{\delta}$)(FIG. 11K). Absolute knock-in count (FIG. 11L), knock-in efficiency (FIG. 11M), and toxicity were improved across all cell types.

Example 9—Application Towards the Generation of CAR-T Cell and TCR Knock-In Cells Chimeric Antigen Receptor (CAR) and T Cell Receptor (TCR) constructs were knocked-in to the endogenous TCR alpha chain (TRAC) genomic locus in primary human T cells. A representative gating strategy for a BCMA antigen specific CAR knock-in is shown in FIGS. 12A-12C. Knock-in efficiency (FIG. 12D) and viability (FIG. 12E) are shown for 2 different primer donor constructs ("ssDNA+shuttle") using 2 different gRNA target sequences (G526 (TCAGGGTTCTGGATATCTGT (SEQ ID NO:121)) and G527 (CTGGATATCTGTGGGACAAG (SEQ ID NO:120)). Both primer donor constructs outperformed the corresponding dsDNA shuttle, dsDNA, and ssDNA HDRTs, reaching a knock-in efficiency of 30-40% at non-toxic doses. FIGS. 12F-12H show similar knock-in rates with a variety of different TCR knock-in constructs using the same G526 ssDNA shuttle system.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

INFORMAL SEQUENCE LISTING

| SEQ ID NO | | Notes |
|---|---|---|
| | Sequence of donor template in primer donor construct | |
| 1 | AACAA**GCAGCGCTTCCTGCCTCGGACGG**ACCCTCCTCTCTTCTTTCTGCAGTCGCTTC<br>CTGCCTCGGATACCCATACGATGTGCCTGATTACGCAGGATCACGGCTCAGCTGGTATG<br>ACCCAGGTAAGGAAGAGCCACATGCCGTCCGAGGCAGGAAGCGCTGCTTGTT | |
| 2 | AACAA**GCAGCGCTTCCTGCCTCGGACGG**CTCCACCTCCCAGGTTCAAGCAATTCTCC<br>TGCCTCAGCCTCCAGAGGAGCTGGGATTACAGGCATGCATCACCACGCCGAGCTAATTT<br>TTGTTATTTTTAGTAGAGACAGGGTTTCACCATATTGGCTAGGCCAGTCTCAAACTCCTG<br>ACCTCAAGTGATCCCCCCACCTCGGCCTCCCAAAGTGCTTGGATTATAGGCATGGGCCA<br>CCGTGCCCGGCCCCTTTCTGGATCATTTCTCCATTCTCTAGAACTAAGGAGCTCAAACTT<br>TTTTGAGTGGAAACATGCGGGACATTTTTACATTGCAACCCCCAACACACAAAAAGTGA<br>TCAGTGCATTCTGACATTCTCTTTTTTATTTATTTAAAACAAAACAAACAAAAAAAAAC<br>AGGGTCTTACTCTGTCACCCAGCTAGAGTGCTGTGGCATAATCATAGCTCACTGCAGGG<br>TCCAACTTCTGGGCTCAAGCGGTCCTCCCACCTTGGCCCCCTTAAGTGCTGGGATTGCA<br>GTCATAAGCCACCGTGCACGGCCTCTCTATTCTACTCCATTTCATTTTTAAAAAAATTGA<br>TGGCCTGAGTGCTGTGGCTCACACATGTGAATCCCAGCACTTCAGGAAGCTGATGCACG<br>AGGATCACTTGAGCCCAGGAGTTCAAAACCAGCCTGGACAACATAGTGAGACCCCATC<br>TCTACATACACACACACATACATGCATACATACATACATACACACATACATAGTAAAA<br>AAATTAGCCAGGCATAGTGGCTCATGCCTGTAATCCTAGCTACTCAAGAGGCTGAGGTG<br>GGAGGATTCTTTGAGCCAGGGAGGTTGAGGCTGCAGTGAGCTGTGATCATGCCACTGC<br>ACTCCAGCCTGGGTGAGGAGAGTGATATCCTGTCTCAAAAAGTAATAATAATAATAATT<br>GATGGTTACATTATTACAAAGGTTAGCATGAGGGAATTTGAGGTAGGGAGTAATGGAA<br>CTGGTGTATACCTTGATTGTGATGGTGGTCACACACATCTATATATGTGACATTCACGG<br>AATCATGCAGTAAAGAAAAATCAATTTCACGTCTGTTCATTTTAAAAGTAACGTTTTTT<br>AAGAAGAAAAAAAAATCGATAGTTGCAGCCCACTAGATAGAATTCATATCACTCAGGGG<br>TTCCAACCTGGAGTATGAAAATTCCTGTCCCTAAAACCCATGATAGTGGATAGGGGGA<br>GGCAGAAAGGGCCATTGCTCGGGCTGTGGGTGGGTGAGCTGGGGAGAAGGGAGAGAG<br>TGGGAGGTTTCACTTCCTGACCCTCCTCTCTTCTTTCTGCAGTCGCTTCCTGCCTCGGAT<br>ACCCATACGATGTGCCTGATTACGCAGGATCACGGCTCAGCTGGTATGACCCAGGTAA<br>GGAAGAGCCACATGGAGAAAGGCCTGGGGCAGGGGGAGAGTGGGGCTGTGGTTTCAT<br>CAGGCCATCGGGGACCTCTCGATGAAGCCATCACTTCTGCCAGAGTGAACCCCACCCTA<br>TAGAGAGAGTGAACCCCAGCATACACACAGGCACATAGATGCAGACACTGCACATTAA<br>GATGCTCACATGCAGGTGGGTGCCCTCGACAGCCGTAAATCACCCACAAATGCCAGAT<br>CTCATGATAATTATTATGACCCGCTCACCATGCACAGAAGACATCCCAGCTCATAAATG<br>TACCTTGCAAAGTCTTATTTCCCACCCAATCCTGACAGATGCTCCATGGTCAAAGATGT<br>TTAGAGCGGAGTCTGCAGAGAGAGGCCGCAGACTGATGGTAAAGTGTGTGGAACGTCC<br>AGCCTTAGACGTTGGAGTTTAGTCGTAGAGGCTGTTTCCCAAATAGGGTTCCATGGAGC<br>ATGTTGGACAAAGGGCAGGCAACACCGCATCTCCCACTGAAGACTGACAGTGTACACC<br>GGCCCAGTAAAGGATCTGAGAAATCCTGCAGCGAAGAAATACATGACACTTTTTAACC<br>CAGCACTTTGCACCCTTATTTCACCACAGACCTCTCCTTCACATTGACTGGGATAACATC<br>GTGCTGAATGTACCTGGGGAGAATTGTGGCTGAAGGGTCTTGAGATGCCACTGTGCAG<br>CCAGAGGGGGTGACAGGGGCCTTGGCAGGCCCTAAGCACGATCTGGGCCCTGCACTGA<br>CATCCTAGCTCCAAGCTTTGGCACACTGCTTGACCTCTTGAGCCCGTTTCCCCAGCTGTG<br>AAATGGGAAGAAAATCTCTTGCCTGGTGAAGCGGCAACGAGCCAGCTCGCTGGGCGGA<br>CAGCCTGCAAATCACCCCACCAATGTTAGGTGTTGAGACGCGCTCGTTCTCCCTCTAAC<br>CAGCCAAGTGCCCTTGGCGAGCCCTGGCCCTGAGCTTTGGCCCCAGAGTGTCCTCGTCG<br>GAAGAAAAGGGTAGCCTGACCCGTGGTTCCCGACCAGGGAAAACCTCCCCCTCAGAAT<br>CACCTGGGAGAGCCTTTCACATTTCTAAAAATTTCTTGAATCAGTGACACATTCATCCA<br>GCTCAAAAATTTAAAAAAATATAAAAAGATCTGTAGTGAAGAGTCTCACTTCCATCTCT<br>ATTCCCGTCTATCCCAGTCGCCCCCGACGTCGACCCCAACACCCCAGGTAATGACTACG<br>TTTATTTGTTTCTTGCATATTCTTCAAGGAGCTCTTTATGCCCGTCCGAGGCAGGAAGCG<br>CTGCAACAA | |
| 3 | GGCGGGACTAGTGGC**GAGACAGCTGGTACACGGCACGG**GAAACTCTCTGGGTGGCC<br>CCAACATGCTAATCCTCCGGCAAACCTCTGTTTCCTCCTCAAAAGGCAGGAGGTCGGAA<br>AGAATAAACAATGAGAGTCACATTAAAAACACAAAATCCTACGGAAATACTGAAGAAT<br>GAGTCTCAGCACTAAGGAAAAGCCTCCAGCAGCTCCTGCTTTCTGAGGGTGAAGGATA<br>GACGCTGTGGCTCTGCATGACTCACTAGCACTCTATCACGGCCATATTCTGGCAGGGTC<br>AGTGGCTCCAACTAACATTTGTTTGGTACTTTACAGTTTATTAAATAGATGTTTATATGG<br>AGAAGCTCTCATTTCTTTCTCAGAAGAGCCTGGCTAGGAAGGTGGATGAGGCACCATAT<br>TCATTTTGCAGGTGAAATTCCTGAGATGTAAGGAGCTGCTGTGACTTGCTCAAGGCCTT<br>ATATCGAGTAAACGGTAGTGCTGGGGCTTAGACGCAGGTGTTCTGATTTATAGTTCAAA<br>ACCTCTATCAATGAGAGAGCAATCTCCTGGTAATGTGATAGATTTCCCAACTTAATGCC<br>AACATACCATAAACCTCCCATTCTGCTAATGCCCAGCCTAAGTTGGGGAGACCACTCCA<br>GATTCCAAGATGTACAGTTTGCTTTGCTGGGCCTTTTTCCCATGCCTGCCTTTACTCTGC<br>CAGAGTTATATTGCTGGGGTTTTGAAGAAGATCCTATTAAATAAAAGAATAAGCAGTAT<br>TATTAAGTAGCCCTGCATTTCAGGTTTCCTTGAGTGGCAGGCCAGGCCTGGCCGTGAAC<br>GTTCACTGAAATCATGGCCTCTTGGCCAAGATTGATAGCTTGTGCCTGTCCCTGAGTCC<br>CAGTCCATCACGAGCAGCTGGTTTCTAAGATGCTATTTCCCGTATAAAGCATGAGACCG<br>TGACTTGCCAGCCCCACAGAGCCCCGCCCTTGTCCATCACTGGCATCTGGACTCCAGCC<br>TGGGTTGGGGCAAAGAGGGAAATGAGATCATGTCCTAACCCTGATCCTCTTGTCCCACA<br>GATATCCAGAACCCTGACCCTGCCGGAGAGGGCAGGGGATCTCTCCTTACTTGTGGCGA<br>CGTGGAGGAGAACCCCGGCCCCATGGCCTTACCAGTGACCGCCTTGCTCCTGCCGCTGG<br>CCTTGCTGCTCCACGCCGCCAGGCCGGAGCAGAAGCTGATCAGCGAGGAGGACCTGGA | |

-continued

INFORMAL SEQUENCE LISTING

| SEQ ID NO | | Notes |
|---|---|---|
| | CATCCAGATGACGCAAACCACCTCAAGTCTGAGTGCCAGTTTGGGTGACCGCGTTACGA<br>TCAGCTGTCGCGCGTCTCAGGATATAAGCAAGTACCTGAATTGGTACCAACAGAAACC<br>CGATGGTACGGTCAAGTTGCTGATCTATCACACCAGCAGGCTCCATTCAGGGGTTCCGT<br>CCCGGTTTTCCGGGTCAGGCAGTGGCACTGACTACAGCCTTACTATCTCTAACCTCGAA<br>CAGGAGGACATAGCTACCTATTTTTGTCAACAAGGTAACACCTTGCCATACACTTTCGG<br>GGGTGGTACGAAACTCGAGATCACAGGGGGCGGGGGGTCCGGTGGTGGTGGATCAGGT<br>GGAGGTGGAAGCGAGGTGAAACTTCAAGAGAGCGGCCCGGGGTTGGTTGCTCCATCTC<br>AAAGCCTGTCAGTGACTTGCACGGTCTCCGGAGTTAGCCTCCCGGATTATGGGGTTTCA<br>TGGATAAGGCAGCCCCCACGAAAAGGTTTGGAGTGGCTCGGCGTGATTTGGGGCAGCG<br>AGACGACCTACTATAACTCTGCGCTTAAATCACGACTGACTATAATAAAAGATAATTCT<br>AAAAGTCAAGTATTTCTGAAAATGAATAGCCTGCAAACTGATGACACGGCTATATATTA<br>TTGTGCAAAACATTACTATTACGGTGGGTCCTATGCGATGGATTATTGGGGCCAGGGCA<br>CATCTGTCACGGTATCATCAACCACTACACCAGCACCCCGGCCACCTACGCCAGCCCCA<br>ACAATCGCTTCACAGCCATTGTCTTTGAGGCCCGAGGCTTGTCGCCCTGCAGCGGGAGG<br>AGCTGTGCATACGAGGGGTCTGGACTTTGCCTGTGACATTTACATTTGGGCACCGCTCG<br>CCGGGACGTGTGGAGTGTTGCTGCTCAGTCTCGTTATCACCCTTTACTGCTCCCTAAAAC<br>GGGGTCGCAAGAAACTGCTGTATATTTTCAAACAGCCATTCATGCGACCTGTGCAAACG<br>ACACAAGAAGAGGACGGATGTTCATGCAGATTCCCGGAGGAAGAAGAAGGAGGGTGC<br>GAGCTGAGAGTCAAATTCTCTCGCAGCGCCGATGCACCAGCTTATCAACAAGGTCAGA<br>ACCAGTTGTACAATGAACTGAACCTGGGGAGGCGAGAGGAGTACGACGTTCTTGACAA<br>GCGCCGGGGACGGGACCCCGAAATGGGGGGTAAACCAAGACGAAAGAACCCCCAGGA<br>GGGGCTCTACAACGAACTTCAGAAGGACAAAATGGCGGAAGCATATTCAGAGATAGGC<br>ATGAAAGGTGAACGCAGAAGAGGGAAAGGACATGACGGCCTCTATCAAGGGTTGAGC<br>ACTGCAACAAAAGACACCTACGATGCGCTGCACATGCAGGCCCTGCCACCACGCTGAA<br>ACTTGTTTATTGCAGCTTATAATGGTTACAAATAAAGCAATAGCATCACAAATTTCACA<br>AATAAAGCATTTTTTTCACTGCATTCTAGTTGTGGTTTGTCCAAACTCATCAATGTATCT<br>TATCATGTCTGGTGTACCAGCTGAGAGACTCTAAATCCAGTGACAAGTCTGTCTGCCTA<br>TTCACCGATTTTGATTCTCAAACAAATGTGTCACAAAGTAAGGATTCTGATGTGTATAT<br>CACAGACAAAACTGTGCTAGACATGAGGTCTATGGACTTCAAGAGCAACAGTGCTGTG<br>GCCTGGAGCAACAAATCTGACTTTGCATGTGCAAACGCCTTCAACAACAGCATTATTCC<br>AGAAGAGACCTTCTTCCCCAGCCCAGGTAAGGGCAGCTTTGGTGCCTTCGCAGGCTGTT<br>TCCTTGCTTCAGGAATGGCCAGGTTCTGCCCAGAGCTCTGGTCAATGATGTCTAAAACT<br>CCTCTGATTGGTGGTCTCGGCCTTATCCATTGCCACCAAAACCCTCTTTTTACTAAGAAA<br>CAGTGAGCCTTGTTCTGGCAGTCCAGAGAATGACACGGGAAAAAAGCAGATGAAGAGA<br>AGGTGGCAGGAGAGGGCACGTGGCCCAGCCTCAGTCTCTCCAACTGAGTTCCTGCCTGC<br>CTGCCTTTGCTCAGACTGTTTGCCCCTTACTGCTCTTCTAGGCCTCATTCTAAGCCCCTTC<br>TCCAAGTTGCCTCTCCTTATTTCTCCCTGTCTGCCAAAAAATCTTTCCCAGCTCACTAAG<br>TCAGTCTCACGCAGTCACTCATTAACCCACCAATCACTGATTGTGCCGGCACATGAATG<br>CACCAGGTGTTGAAGTGGAGGAATTAAAAAGTCAGATGAGGGGTGTGCCCAGAGGAA<br>GCACCATTCTAGTTGGGGGAGCCCATCTGTCAGCTGGGAAAAGTCCAAATAACTTCAG<br>ATTGGAATGTGTTTTAACTCAGGGTTGAGAAAACAGCTACCTTCAGGACAAAAGTCAG<br>GGAAGGGCTCTCTGAAGAAATGCTACTTGAAGATACCAGCCCTACCAAGGGCAGGGAG<br>AGGACCCTATAGAGGCCTGGGACAGGAGCTCAATGAGAAAGGAGAAGAGCAGCAGGC<br>ATGAGTTGAATGAAGGAGGCAGGGCCGGGTCACAGGCCGTGCCGTGTACCAGCTGTCT<br>CGGTGCTGGAAGTGGT | |
| 4 | TGGCG**ACTCCAGTCCCCACATCAGC**CGGGAGATGAGAGAAGAGAGTGCTAGGCAGTT<br>TCCTGGCTGAACACGCCAGCCCAATACTTAAAGAGAGCAACTCCTGACTCCGATAGAG<br>ACTGGATGGACCCACAAGGGTGACAGCCCAGGCGGACCGATCTTCCCATCCCACATCC<br>TCCGGCGCGATGCCAAAAAGAGGCTGACGGCAACTGGGCCTTCTGCAGAGAAAGACCT<br>CCGCTTCACTGCCCCGGCTGGTCCCAAGGGTCAGGAAGATGGATTCATATTTGCTCATG<br>TGGGGCCTCCTGACCTTTATTATGGTCCCTGGCTGTCAAGCAGAGCTCTGTGACGATGA<br>CCCGCCAGAGATCCCACACGCCACATTCAAAGCCATGGCCTACAAGGAAGGAACCATG<br>TTGAACTGTGAATGCAAGAGAGGTTTCCGCAGAATAAAAAGCGGGTCACTCTATATGC<br>TCTGTACAGGAAACTCTAGCCACTCGTCCTGGGACAACCAATGTCAATGCACAAGCTCT<br>GCCACTCGGAACACAACGAAACAAGTGACACCTCAACCTGAAGAACAGAAAGAAAGG<br>AAAACCACAGAAATGCAAAGTCCAATGCAGCCAGTGGACCAAGCGAGCCTTCCAGGTC<br>ACTGCAGGGAACCTCCACCATGGGAAAATGAAGCCACAGAGAGAATTTATCATTTCGT<br>GGTGGGGCAGATGGTTTATTATCAGTGCGTCCAGGGATACAGGGCTCTACACAGAGGT<br>CCTGCTGAGAGCGTCTGCAAAATGACCCACGGGAAGACAAGGTGGACCCAGCCCCAGC<br>TCATATGCACAGGTGAAATGGAGACCAGTCAGTTTCCAGGTGAAGAGAAGCCTCAGGC<br>AAGCCCCGAAGGCCGTCCTGAGAGTGAGACTTCCTGCCTCGTCACAACAACAGATTTTC<br>AAATACAGACAGAAATGGCTGCAACCATGGAGACGTCCATATTTACAACAGAGTACCA<br>GGTAGCAGTGGCCGGCTGTGTTTTCCTGCTGATCAGCGTCCTCCTCCTGAGTGGGCTCA<br>CCTGGCAGCGGAGACAGAGGAAGAGTAGAAGAACAATCGGATCGGGTGGGACTAGTG<br>GCAGCAAGGGCGAGGAGCTGTTCACCGGGGTGGTGCCCATCCTGGTCGAGCTGGACGG<br>CGACGTAAACGGCCACAAGTTCAGCGTGCGCGGCGAGGGCGAGGGCGATGCCACCAAC<br>GGCAAGCTGACCCTGAAGTTCATCTGCACCACCGGCAAGCTGCCCGTGCCCTGGCCCAC<br>CCTCGTGACCACCCTGACCTACGGCGTGCAGTGCTTCAGCCGCTACCCCGACCACATGA<br>AGCGCCACGACTTCTTCAAGTCCGCCATGCCCGAAGGCTACGTCCAGGAGCGCACCATC<br>AGCTTCAAGGACGACGGCACCTACAAGACCCGCGCCGAGGTGAAGTTCGAGGGCGACA<br>CCCTGGTGAACCGCATCGAGCTGAAGGGCATCGACTTCAAGGAGGACGGCAACATCCT<br>GGGGCACAAGCTGGAGTACAACTTCAACAGCCACAACGTCTATATCACCGCCGACAAG | |

-continued

INFORMAL SEQUENCE LISTING

| SEQ ID NO | | Notes |
|---|---|---|
| | CAGAAGAACGGCATCAAGGCCAACTTCAAGATCCGCCACAACGTGGAGGACGGCAGC<br>GTGCAGCTCGCCGACCACTACCAGCAGAACACCCCCATCGGCGACGGCCCCGTGCTGC<br>TGCCCGACAACCACTACCTGAGCACCCAGTCCGTGCTGAGCAAAGACCCCAACGAGAA<br>GCGCGATCACATGGTCCTGCTGGAGTTCGTGACCGCCGCCGGGATCACTTAGAACTTGT<br>TTATTGCAGCTTATAATGGTTACAAATAAAGCAATAGCATCACAAATTTCACAAATAAA<br>GCATTTTTTTCACTGCATTCTAGTTGTGGTTTGTCCAAACTCATCAATGTATCTTATCAT<br>GTCTGGTAAGGGCCTGTGGCTGCCCCCGGAATTCCGGGAAGGCTGATGGGCATCCCTCT<br>TCCCAGCCACAGAACCAGAGGGAGTCCCCAGGTAGATGGTTCCAAGAAGGGAGTTGAA<br>TCTTGGGTTCCACCTCTTGCCTGTGACCCACGGGGACCCCAGTTTATGCCTCACTGTTCC<br>TTGGTCTGTCAAGAGAGCCTGAAATAGCATTAGGTTCTCCTGTCCTTCTCAGTCCTTGAC<br>AATTAATTCTGGGAAGAATAGTGTGGCATGATATTTGGGATATTTGGATGTTAACAGGG<br>TCCCGATGAGCAGGTTTCTCACCGGCTGATGTGGGGACTGTATGTGGTG | |
| | Sequence of donor template in mixed chain donor construct | |
| 5 | AACAA**GCAGCGCTTCCTGCCTCGGACGG**ACCCTCCTCTCTTCTTTCTGCAGTCGCTTC<br>CTGCCTCGGATACCCATACGATGTGCCTGATTACGCAGGATCACGGCTCAGCTGGTATG<br>ACCCAGGTAAGGAAGAGCCACATGAACAAGCAGCGCTTCCTGCCTCGGACGG | |
| 6 | **CCGTCCGAGGCAGGAAGCGCTGC**TTGTTACCCTCCTCTCTTCTTTCTGCAGTCGCTTC<br>CTGCCTCGGATACCCATACGATGTGCCTGATTACGCAGGATCACGGCTCAGCTGGTATG<br>ACCCAGGTAAGGAAGAGCCACATGCCGTCCGAGGCAGGAAGCGCTGCTTGTT | |
| | Sequence of donor template in half loop donor construct | |
| 7 | AACAA**GCAGCGCTTCCTGCCTCGGACGG**ACCCTCCTCTCTTCTTTCTGCAGTCGCTTC<br>CTGCCTCGGATACCCATACGATGTGCCTGATTACGCAGGATCACGGCTCAGCTGGTATG<br>ACCCAGGTAAGGAAGAGCCACATGCCGTCCGAGGCAGGAAGCGCTGCTTGTT | |
| | Sequence of donor template in hairpin donor construct | |
| 8 | GGT**CCGTCCGAGGCAGGAAGCGCTGC**AACAAGCAGCGCTTCCTGCCTCGGACGGACC<br>CTCCTCTCTTCTTTCTGCAGTCGCTTCCTGCCTCGGATACCCATACGATGTGCCTGATTA<br>CGCAGGATCACGGCTCAGCTGGTATGACCCAGGTAAGGAAGAGCCACATG | |
| 9 | ACCCTCCTCTCTTCTTTCTGCAGTCGCTTCCTGCCTCGGATACCCATACGATGTGCCTGA<br>TTACGCAGGATCACGGCTCAGCTGGTATGACCCAGGTAAGGAAGAGCCACATGCCGTC<br>CGAGGCAGGAAGCGCTGCAACAA**GCAGCGCTTCCTGCCTCGGACGG**ATG | |
| | Sequence of donor template in hairpin/primer donor construct | |
| 10 | GGT**CCGTCCGAGGCAGGAAGCGCTGC**AACAAGCAGCGCTTCCTGCCTCGGACGGACC<br>CTCCTCTCTTCTTTCTGCAGTCGCTTCCTGCCTCGGATACCCATACGATGTGCCTGATTA<br>CGCAGGATCACGGCTCAGCTGGTATGACCCAGGTAAGGAAGAGCCACATG**CCGTCCG**<br>**AGGCAGGAAGCGCTGC**TTGTT | |
| 11 | AACAA**GCAGCGCTTCCTGCCTCGGACGG**ACCCTCCTCTCTTCTTTCTGCAGTCGCTTC<br>CTGCCTCGGATACCCATACGATGTGCCTGATTACGCAGGATCACGGCTCAGCTGGTATG<br>ACCCAGGTAAGGAAGAGCCACATG**CCGTCCGAGGCAGGAAGCGCTGC**AACAAGCAG<br>CGCTTCCTGCCTCGGACGGATG | |
| | Sequence of donor template in mixed loop donor construct | |
| 12 | AACAA**GCAGCGCTTCCTGCCTCGGACGG**ACCCTCCTCTCTTCTTTCTGCAGTCGCTTC<br>CTGCCTCGGATACCCATACGATGTGCCTGATTACGCAGGATCACGGCTCAGCTGGTATG<br>ACCCAGGTAAGGAAGAGCCACATGCCGTCCGAGGCAGGAAGCGCTGCTTGTTTTTGAA<br>GCTACCATGGATGA | |
| 13 | AACAA**GCAGCGCTTCCTGCCTCGGACGG**ACCCTCCTCTCTTCTTTCTGCAGTCGCTTC<br>CTGCCTCGGATACCCATACGATGTGCCTGATTACGCAGGATCACGGCTCAGCTGGTATG<br>ACCCAGGTAAGGAAGAGCCACATGCCGTCCGAGGCAGGAAGCGCTGCTTGTTTCATCC<br>ATGGTAGCTTCAAA | |
| 14 | TTTGAAGCTACCATGGATGAACCCTCCTCTCTTCTTTCTGCAGTCGCTTCCTGCCTCGGA<br>TACCCATACGATGTGCCTGATTACGCAGGATCACGGCTCAGCTGGTATGACCCAGGTAA<br>GGAAGAGCCACATGTCATCCATGGTAGCTTCAAA**CCGTCCGAGGCAGGAAGCGCTGC**<br>TTGTT | |
| 15 | TTTGAAGCTACCATGGATGAACCCTCCTCTCTTCTTTCTGCAGTCGCTTCCTGCCTCGGA<br>TACCCATACGATGTGCCTGATTACGCAGGATCACGGCTCAGCTGGTATGACCCAGGTAA<br>GGAAGAGCCACATGTCATCCATGGTAGCTTCAAAAACAA**GCAGCGCTTCCTGCCTCG**<br>**GACGG** | |

-continued

| INFORMAL SEQUENCE LISTING | | |
|---|---|---|
| SEQ ID NO | | Notes |
| | Sequence of donor template in double hairpin donor construct | |
| 16 | GGT**CCGTCCGAGGCAGGAAGCGCTGC**AACAAGCAGCGCTTCCTGCCTCGGACGGACC CTCCTCTCTTCTTTCTGCAGTCGCTTCCTGCCTCGGATACCCATACGATGTGCCTGATTA CGCAGGATCACGGCTCAGCTGGTATGACCCAGGTAAGGAAGAGCCACATG | |
| 17 | GGT**CCGTCCGAGGCAGGAAGCGCTGC**AACAAGCAGCGCTTCCTGCCTCGGACGGCAT GTGGCTCTTCCTTACCTGGGTCATACCAGCTGAGCCGTGATCCTGCGTAATCAGGCACA TCGTATGGGTATCCGAGGCAGGAAGCGACTGCAGAAAGAAGAGAGGAGGGT | |
| | Sequence of donor template in cap donor construct | |
| 18 | ACCCTCCTCTCTTCTTTCTGCAGTCGCTTCCTGCCTCGGATACCCATACGATGTGCCTGA TTACGCAGGATCACGGCTCAGCTGGTATGACCCAGGTAAGGAAGAGCCACATG | |
| 19 | CAGAAAGAAGAGAGGAGGGT**CCGTCCGAGGCAGGAAGCGCTGC**AACAAGCAGCGCT TCCTGCCTCGGACGG | |
| 20 | **CCGTCCGAGGCAGGAAGCGCTGC**AACAAGCAGCGCTTCCTGCCTCGGACGGCATGTG GCTCTTCCTTACCT | |
| | Sequence of donor template in internal cap donor construct | |
| 21 | ACCCTCCTCTCTTCTTTCTGCAGTCGCTTCCTGCCTCGGATACCCATACGATGTGCCTGA TTACGCAGGATCA**CGGCTCAGCTGGTATGACCC**AGGTAAGGAAGAGCCACATG | |
| 22 | GGT**CCGTCCGAGGCAGGAAGCGCTGC**AACAAGCAGCGCTTCCTGCCTCGGACGGACC GGGTCATACCAGCTGAGCCG | |
| 23 | TCCGAGGCAGGAAGCGACTGGGT**CCGTCCGAGGCAGGAAGCGCTGC**TTGTTGCAGC GCTTCCTGCCTCGGACGGACC | |
| 24 | TGCGTAATCAGGCACATCGTGGT**CCGTCCGAGGCAGGAAGCGCTGC**TTGTTGCAGCG CTTCCTGCCTCGGACGGACC | |
| | NLS sequences | |
| 25 | AVKRPAATKKAGQAKKKKLD | |
| 26 | MSRRRKANPTKLSENAKKLAKEVEN | |
| 27 | PAAKRVKLD | |
| 28 | KLKIKRPVK | |
| 29 | PKKKRKV | |
| | DNA-binding protein target sequences | |
| 30 | GCAGCGCTTCCTGCCTCGGACGG | |
| 31 | CCGTCCGAGGCAGGAAGCGCTGC | |
| 32 | GAGACAGCTGGTACACGGCACGG | |
| 33 | CCGTGCCGTGTACCAGCTGTCTC | |
| 34 | ACTCCAGTCCCCACATCAGC | |
| 35 | GCTGATGTGGGGACTGTATG | |
| | Example 5 sequences | |
| 36 | AACAAGCAGCGCTTCCTGCCTCGGACGGctccacctcccaggttcaagcaattctcctgc ctcagcctccagaggagctgggattacaggcatgcatcaccacgccgagctaatttttgt tatttttagtagagacagggtttcaccatattggctaggccagtctcaaactcctgacct caagtgatcccccacctcggcctcccaaagtgcttggattataggcatgggccaccgtg cccggccCCTTTCTGGATCATTTCTCCATTCTCTAGAACTAAGGAGCTCAAACTTTTTTG AGTGGAAACATGCGGGACATTTTTACATTGCAACCCCCAACACACAAAAAGTGATCAGTG CATTCTGACATTCTCTTTTTTATTTATTTaaaacaaaacaaacaaaaaaaaaacagggtct tactctgtcacccagctagagtgctgtggcataatcatagctcactgcagggtccaactt ctgggctcaagcggtcctcccaccttggccccttaagtgctgggattgcagtcataagc caccgtgcacggcCTCTCTATTCTACTCCATTTCATTTTTAAAAAAATTGATGGCctgag | CD5-HA base HDRT |

-continued

INFORMAL SEQUENCE LISTING

| SEQ ID NO | | Notes |
|---|---|---|
| | tgctgtggctcacacatgtgaatcccagcacttcaggaagctgatgcacgaggatcactt<br>gagcccaggagttcaaaaccagcctggacaacatagtgagaccccatctctacatacaca<br>cacacatacatgcatacatacatacatacacacatacatagtaaaaaaattagccaggca<br>tagtggctcatgcctgtaatcctagctactcaagaggctgaggtgggaggattctttga<br>gccagggaggttgaggctgcagtgagctgtgatcatgccactgcactccagcctgggtg<br>aggagagtgatatcctgtctcaaaaagtaataataataaTAATTGATGGTTACATTatta<br>caaaggttagcatgagggaatttgaggtagggagtaatggaactggtgtataccttga<br>ttgtgatggtggtcacacacatctatatatgtgacattcacggaatcatgcagtaaaga<br>aaaatcaatttcacgtctgttcattttaAAAGTAACGTTTTTTAAGAAGaaaaaaaatc<br>gatagttgcagcccactagatagaattcatatcactcaggggttccaacctggagtatg<br>aaaaTTCCTGTCCCTAAAACCCATGATAGTGGATAGGGGGAGGCAGAAAGGGCCATTGCT<br>CGGGCTGTGGGTGGGTGAGCTGGGGAGAAGGGAGAGAGTGGGAGGTTTCACTTCCTGA<br>CCCTCCTCTCTTCTTTCTGCAGTCGCTTCCTGCCTCGGATACCCATACGATGTGCCTGAT<br>TACGCAGGATCACGGCTCAGCTGGTATGACCCAGGTAAGGAAGAGCCACATGGAGAAA<br>GGCCTGGGGCAGGGGGAGAGTGGGGCTGTGGTTTCATCAGGCCATCGGGGACCTCTCG<br>ATGAAGCCATCACTTCTGCCAGAGTGAACCCCACCCTATAGAGAGAGTGAACCCCAGC<br>ATACACACAGGCACATAGATGCAGACACTGCACATTAAGATGCTCACATGCAGGTGGG<br>TGCCCTCGACAGCCGTAAATCACCCACAAATGCCAGATCTCATGATAATTATTATGACC<br>CGCTCACCATGCACAGAAGACATCCCAGCTCATAAATGTACCTTGCAAAGTCTTATTTC<br>CCACCCAATCCTGACAGATGCTCCATGGTCAAAGATGTTTAGAGCGGAGTCTGCAGAG<br>AGAGGCCGCAGACTGATGGTAAAGTGTGTGGAACGTCCAGCCTTAGACGTTGGAGTTT<br>AGTCGTAGAGGCTGTTTCCCaaatagggttccatggagcatgttggacaaagggcaggc<br>aacaccgcatctcccactgaagactgacagtgtacaccggcccagtaaaggatctgaga<br>aatcctgcagcgaagaaatacatgacactttttaacccagcactttgcacccttattt<br>caccacagacctctccttcacattgactgggataacatcgtgctgaaTGTACCTGGGGA<br>GAATTGTGGCTGAAGGGTCTTGAGATGCCACTGTGCAGCCAGAGGGGGTGAcaggggcc<br>ttggcaggccctaagcacgatctgggccctgcactgacatcctagctccaagctttgg<br>cacactgcttgacctcttgagcccgtttccccagctgtgaaatgggaagaaaatctctT<br>GCCTGGTGAAGCGGCAACGAGCCAGCTCGCTGGGCGGACAGCCTGCAAATCACCCCACC<br>AATGTTAGGTGTTGAGACGCGCTCGTTCTCCCTCTAACCAGCCAAGTGCCCTTGGCGAGC<br>CCTGGCCCTGAGCTTTGGCCCCAGAGTGTCCTCGTCGGAAGAAAAGGGTAGCCTGACCC<br>GTGGTTCCCGACCAGGGAAAACCTCCCCCTCAGAATCACCTGGGAGAGCCTTTCACAT<br>TTCTAAAAatttcttgaatcagtgacacattcatccagctcaaaaatttaaaaaaatat<br>aaaaagatctgtagtgaagagtctcacttccatctctattcccGTCTATCCCAGTCGC<br>CCCCGACGTCGACCCCAACACCCCAGGTAATGACTACGTTTATTTGTTTCTTGCATATT<br>CTTCAAGGAGCTCTTTATGCCCGTCCGAGGCAGGAAGCGCTGCAACAA | |
| 37 | cttgaacctgggaggtggagCCGTCCGAGGCAGGAAGCGCTGCTTGTT | CD5-HA 5' RC |
| 38 | TTGTTGCAGCGCTTCCTGCCTCGGACGGGCATAAAGAGCTCCTTGAAG | CD5-HA 3' RC |
| 39 | TGGCGACTCCAGTCCCCACATCAGCCGGGAGATGAGAGAAGAGAGTGCTAGGCAGTTT<br>CCTGGCTGAACACGCCAGCCCAATACTTAAAGAGAGCAACTCCTGACTCCGATAGAGA<br>CTGGATGGACCCACAAGGGTGACAGCCCAGGCGGACCGATCTTCCCATCCCACATCCTC<br>CGGCGCGATGCCAAAAAGAGGCTGACGGCAACTGGGCCTTCTGCAGAGAAAGACCTCC<br>GCTTCACTGCCCCGGCTGGTCCCAAGGGTCAGGAAGATGGATTCATATTTGCTCATGTG<br>GGGCCTCCTGACCTTTATTATGGTCCCTGGCTGTCAAGCAAAGGAGGCATGCCCCACAG<br>GCCTGTACACACACAGCGGTGAGTGCTGCAAAGCCTGCAACCTGGGCGAGGGTGTGGC<br>CCAGCCTTGTGGAGCCAACCAGACCGTGTGTGAGCCCTGCCTGGACAGCGTGACGTTCT<br>CCGACGTGGTGAGCGCGACCGAGCCGTGCAAGCCGTGCACCGAGTGCGTGGGGCTCCA<br>GAGCATGTCGGCGCCATGCGTGGAGGCCGACGACGCCGTGTGCCGCTGCGCCTACGGC<br>TACTACCAGGATGAGACGACTGGGCGCTGCGAGGCGTGCCGCGTGTGCGAGGCGGGCT<br>CGGGCCTCGTGTTCTCCTGCCAGGACAAGCAGAACACCGTGTGCGAGGAGTGCCCCGA<br>CGGCACGTATTCCGACGAGGCCAACCACGTGGACCCGTGCCTGCCCTGCACCGTGTGCG<br>AGGACACCGAGCGCCAGCTCCGCGAGTGCACACGCTGGGCCGACGCCGAGTGCGAGGA<br>GATCCCTGGCCGTTGGATTACACGGTCCACACCCCCAGAGGGCTCGGACAGCACAGCC<br>CCCAGCACCCAGGAGCCTGAGGCACCTCCAGAACAAGACCTCATAGCCAGCACGGTGG<br>CAGGTGTGGTGACCACAGTGATGGGCAGCTCCCAGCCCGTGGTGACCCGAGGCACCAC<br>CGACAACCTCATCCCTGTCTATTGCTCCATCCTGGCTGCTGTGGTTGTGGGTCTTGTGGC<br>CTACATAGCCTTCAAGAGGTGGAACAGCCGCGCCAAGCGCTCGGGTTCGGGTGCCACC<br>AACTTCAGCCTGCTGAAGCAGGCCGGCGACGTGGAGGAGAACCCCGGCCCCGTAAGGG<br>CCTGTGGCTGCCCCCGGAATTCCGGGAAGGCTGATGGGCATCCCTCTTCCCAGCCACAG<br>AACCAGAGGGAGTCCCCAGGTAGATGGTTCCAAGAAGGGAGTTGAATCTTGGGTTCCA<br>CCTCTTGCCTGTGACCCACGGGGACCCCAGTTTATGCCTCACTGTTCCTTGGTCTGTCAA<br>GAGAGCCTGAAATAGCATTAGGTTCTCCTGTCCTTCTCAGTCCTTGACAATTAATTCTGG<br>GAAGAATAGTGTGGCATGATATTTGGGATATTTGGATGTTAACAGGGTCCCGATGAGC<br>AGGTTTCTCACCGGCTGATGTGGGGACTGTATGTGGTG | IL2RA-tNGFR base HDRT |
| 40 | GCACTCTCTTCTCTCATCTCCCGGCTGATGTGGGGACTGGAGTCGCCA | IL2RA-tNGFR 5' RC |
| 41 | CACCACATACAGTCCCCACATCAGCCGGTGAGAAACCTGCTCATCGGG | IL2RA-tNGFR 3' RC |

-continued

INFORMAL SEQUENCE LISTING

| SEQ ID NO | | Notes |
|---|---|---|
| | TGGCGACTCCAGTCCCCACATCAGCCGGGAGATGAGAGAAGAGAGTGCTAGGCAGTTT<br>CCTGGCTGAACACGCCAGCCCAATACTTAAAGAGAGCAACTCCTGACTCCGATAGAGA<br>CTGGATGGACCCACAAGGGTGACAGCCCAGGCGGACCGATCTTCCCATCCCACATCCTC<br>CGGCGCGATGCCAAAAAGAGGCTGACGGCAACTGGGCCTTCTGCAGAGAAAGACCTCC<br>GCTTCACTGCCCCGGCTGGTCCCAAGGGTCAGGAAGATGGATTCATATTTGCTCATGTG<br>GGGCCTCCTGACCTTTATTATGGTCCCTGGCTGTCAAGCAGAGCTCTGTGACGATGACC<br>CGCCAGAGATCCCACACGCCACATTCAAAGCCATGGCCTACAAGGAAGGAACCATGTT<br>GAACTGTGAATGCAAGAGAGGTTTCCGCAGAATAAAAAGCGGGTCACTCTATATGCTC<br>TGTACAGGAAACTCTAGCCACTCGTCCTGGGACAACCAATGTCAATGCACAAGCTCTGC<br>CACTCGGAACACAACGAAACAAGTGACACCTCAACCTGAAGAACAGAAAGAAAGGAA<br>AACCACAGAAATGCAAAGTCCAATGCAGCCAGTGGACCAAGCGAGCCTTCCAGGTCAC<br>TGCAGGGAACCTCCACCATGGAAAATGAAGCCACAGAGAGAATTTATCATTTCGTGG<br>TGGGGCAGATGGTTTATTATCAGTGCGTCCAGGGATACAGGGCTCTACACAGAGGTCCT<br>GCTGAGAGCGTCTGCAAAATGACCCACGGGAAGACAAGGTGGACCCAGCCCCAGCTCA<br>TATGCACAGGTGAAATGGAGACCAGTCAGTTTCCAGGTGAAGAGAAGCCTCAGGCAAG<br>CCCCGAAGGCCGTCCTGAGAGTGAGACTTCCTGCCTCGTCACAACAACAGATTTTCAAA<br>TACAGACAGAAATGGCTGCAACCATGGAGACGTCCATATTTACAACAGAGTACCAGGT<br>AGCAGTGGCCGGCTGTGTTTTCCTGCTGATCAGCGTCCTCCTCCTGAGTGGGCTCACCT<br>GGCAGCGGAGACAGAGGAAGAGTAGAAGAACAATCGGATCGGGTGGGACTAGTGGCA<br>GCAAGGGCGAGGAGCTGTTCACCGGGGTGGTGCCCATCCTGGTCGAGCTGGACGGCGA<br>CGTAAACGGCCACAAGTTCAGCGTGCGCGGCGAGGGCGAGGGCGATGCCACCAACGGC<br>AAGCTGACCCTGAAGTTCATCTGCACCACCGGCAAGCTGCCCGTGCCCTGGCCCACCCT<br>CGTGACCACCCTGACCTACGGCGTGCAGTGCTTCAGCCGCTACCCCGACCACATGAAGC<br>GCCACGACTTCTTCAAGTCCGCCATGCCCGAAGGCTACGTCCAGGAGCGCACCATCAGC<br>TTCAAGGACGACGGCACCTACAAGACCCGCGCCGAGGTGAAGTTCGAGGGCGACACCC<br>TGGTGAACCGCATCGAGCTGAAGGGCATCGACTTCAAGGAGGACGGCAACATCCTGGG<br>GCACAAGCTGGAGTACAACTTCAACAGCCACAACGTCTATATCACCGCCGACAAGCAG<br>AAGAACGGCATCAAGGCCAACTTCAAGATCCGCCACAACGTGGAGGACGGCAGCGTGC<br>AGCTCGCCGACCACTACCAGCAGAACACCCCCATCGGCGACGGCCCCGTGCTGCTGCC<br>CGACAACCACTACCTGAGCACCCAGTCCGTGCTGAGCAAAGACCCCAACGAGAAGCGC<br>GATCACATGGTCCTgCTGGAgTTCGTGACCGCCGCCGGGATCACTTAGaacttgttta<br>ttgcagcttataatggttacaaataaagcaatagcatcacaaatttcacaaataaagc<br>attttttcactgcattctagttgtggttttgtccaaactcatcaatgtatcttatca<br>tgtctgGTAAGGGCCTGTGGCTGCCCCCGGAATTCCGGGAAGGCTGATGGGCATCCCTCT<br>TCCCAGCCACAGAACCAGAGGGAGTCCCCAGGTAGATGGTTCCAAGAAGGGAGTTGAA<br>TCTTGGGTTCCACCTCTTGCCTGTGACCCACGGGGACCCCAGTTTATGCCTCACTGTTCC<br>TTGGTCTGTCAAGAGAGCCTGAAATAGCATTAGGTTCTCCTGTCCTTCTCAGTCCTTGAC<br>AATTAATTCTGGGAAGAATAGTGTGGCATGATATTTGGGATATTTGGATGTTAACAGGG<br>TCCCGATGAGCAGGTTTCTCACCGGCTGATGTGGGGACTGTATGTGGTG | IL2RA-CD25-GFP base HDRT |
| 42 | GCACTCTCTTCTCTCATCTCCCGGCTGATGTGGGGACTGGAGTCGCCA | IL2RA-CD25-GFP 5' RC |
| 43 | CACCACATACAGTCCCCACATCAGCCGGTGAGAAACCTGCTCATCGGG | IL2RA-CD25-GFP 3' RC |

What is claimed is:

1. A donor construct comprising at least one donor template comprising a single-stranded homology directed repair template (HDRT) and one or more DNA-binding protein target sequences, wherein at least one DNA-binding protein target sequence forms a double-stranded DNA duplex with a complementary polynucleotide sequence.

2. The donor construct of claim 1, wherein the donor construct comprises (a) a first polynucleotide comprising a single donor template, and (b) at least one second polynucleotide comprising a complementary polynucleotide sequence, wherein the donor template is a single-stranded linear template.

3. The donor construct of claim 2, wherein the donor template comprises only one DNA-binding protein target sequence, and wherein the DNA-binding protein target sequence hybridizes to the complementary polynucleotide sequence.

4. The donor construct of claim 3, wherein the DNA-binding protein target sequence is located at or proximal to the 5' terminus or 3' terminus of the donor template.

5. The donor construct of claim 2, wherein the donor template comprises:

a first DNA-binding protein target sequence located at or proximal to the 5' terminus of the donor template;

a second DNA-binding protein target sequence located at or proximal to the 3' terminus of the donor template;

a first complementary polynucleotide sequence; and a second complementary polynucleotide sequence, wherein the first DNA-binding protein target sequence hybridizes to the first complementary polynucleotide sequence and the second DNA-binding protein target sequence hybridizes to the second complementary polynucleotide sequence.

6. The donor construct of claim 1, wherein the donor construct comprises (a) a first donor template comprising a first DNA-binding protein target sequence located at or proximal to the 3' terminus of the first donor template, and (b) a second donor template comprising a second DNA-binding protein target sequence located at or proximal to the 3' terminus of the second donor template, wherein the first DNA-binding protein target sequence hybridizes to the second DNA-binding protein target sequence.

7. The donor construct of claim 6, wherein the second donor template further comprises a third DNA-binding protein target sequence located at or proximal to the 5' terminus of the second donor template, and the donor construct further comprises (c) a third donor template comprising a fourth DNA-binding protein target sequence located at or proximal to the 5' terminus of the third template, wherein the third DNA-binding protein target sequence hybridizes to the fourth DNA-binding protein target sequence.

8. The donor construct of claim 1, wherein the DNA-binding protein target sequence and the complementary polynucleotide sequence form a hairpin.

9. The donor construct of claim 8, wherein the donor construct comprises a single donor template and the donor template comprises a single hairpin formed by a first DNA-binding protein target sequence and a second DNA-binding protein target sequence as the complementary polynucleotide sequence.

10. The donor construct of claim 9, wherein the donor template further comprises a third DNA-binding protein target sequence, and the donor construct further comprises a polynucleotide comprising a second complementary polynucleotide sequence, wherein the third DNA-binding protein target sequence hybridize to the second complementary polynucleotide sequence.

11. The donor construct of claim 8, wherein the donor construct comprises a single donor template, and the donor template comprises two hairpins and:

(a) a first DNA-binding protein target sequence;

(b) a second DNA-binding protein target sequence as a first complementary polynucleotide sequence;

(c) a third DNA-binding protein target sequence; and (d) a fourth DNA-binding protein target sequence as a second complementary polynucleotide sequence, wherein the first DNA-binding protein target sequence hybridizes to the second DNA-binding protein target sequence to form a first hairpin at or proximal to the 5' terminus of the donor template, and the third DNA-binding protein target sequence hybridizes to the fourth DNA-binding protein target sequence to form a second hairpin at or proximal to the 3' terminus of the donor template.

12. The donor construct of claim 8, wherein the donor construct comprises a first donor template and a second donor template, each comprising a first DNA-binding protein target sequence and a second DNA-binding protein target sequence as the complementary polynucleotide sequence, and wherein a portion of the first donor template and a portion of the second donor template hybridize to each other.

13. The donor construct of claim 8, wherein the donor construct comprises a single donor template and the donor template comprises:

(a) a first fragment comprising a first hairpin formed by a first DNA-binding protein target sequence and a second DNA-binding protein target sequence as the complementary polynucleotide sequence;

(b) a second fragment comprising a second hairpin formed by a third DNA-binding protein target sequence and a fourth DNA-binding protein target sequence as the complementary polynucleotide sequence; and C a third fragment comprising the HDRT, wherein a portion of the first fragment hybridize to a 5' portion of the third fragment, and a portion of the second fragment hybridize to a 3' portion of the third fragment.

14. The donor construct of claim 1, wherein the DNA-binding protein target sequence comprises a sequence of any one of SEQ ID NOS: 30-35.

15. The donor construct of claim 1, wherein the donor template comprises one or more protospacer adjacent motifs (PAMs).

16. A composition for modifying a target nucleic acid, comprising:

(a) a targetable nuclease;

(b) a DNA-binding protein;

(c) a donor construct of claim 1.

17. The composition of claim 16, wherein the composition comprises a target guide RNA (gRNA) and a donor gRNA.

18. The composition of claim 16, wherein the targetable nuclease has nuclease activity.

19. The composition of claim 18, wherein the active targetable nuclease is a Cas nuclease.

20. The composition of claim 16, wherein the DNA-binding protein is an RNA-guided nuclease having nuclease activity.

21. The composition of claim 20, wherein the DNA-binding protein is a Cas nuclease.

22. A composition for modifying a target nucleic acid, comprising:

(a) a DNA-binding protein; and (b) a donor construct of claim 1.

23. The composition of claim 22, wherein the DNA-binding protein is an RNA-guided nuclease having nuclease activity.

24. The composition of claim 23, wherein the DNA-binding protein is a Cas nuclease.

25. A method for modifying a target nucleic acid in a cell, comprising introducing into the cell a composition of claim 16, wherein the HDRT is integrated into the target nucleic acid.

26. The method of claim 25, wherein an exogenous nucleotide sequence is introduced into the cell and wherein the modifying comprises inserting the exogenous nucleotide sequence into the target nucleic acid.

27. The method of claim 25, wherein the modifying comprises excising the target nucleic acid or targeting an exogenous protein to the target nucleic acid.

* * * * *

SEQUENCE LISTING

<160> NUMBER OF SEQ ID NOS: 122

<210> SEQ ID NO 1
<211> LENGTH: 169
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
aacaagcagc gcttcctgcc tcggacggac cctcctctct tctttctgca gtcgcttcct 60
gcctcggata cccatacgat gtgcctgatt acgcaggatc acggctcagc tggtatgacc 120
caggtaagga agagccacat gccgtccgag gcaggaagcg ctgcttgtt 169

<210> SEQ ID NO 2

<211> LENGTH: 2708
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 2
aacaagcagc gcttcctgcc tcggacggct ccacctccca ggttcaagca attctcctgc 60
ctcagcctcc agaggagctg ggattacagg catgcatcac cacgccgagc taatttttgt 120
tatttttagt agagacaggg tttcaccata ttggctaggc cagtctcaaa ctcctgacct 180
caagtgatcc ccccacctcg gcctcccaaa gtgcttggat tataggcatg ggccaccgtg 240
cccggcccct ttctggatca tttctccatt ctctagaact aaggagctca aactttttttg 300 agtggaaaca tgcgggacat ttttacattg caaccccccaa cacacaaaaa gtgatcagtg 360
cattctgaca ttctcttttt tatttattta aaacaaaaca aacaaaaaaa aacagggtct 420
tactctgtca cccagctaga gtgctgtggc ataatcatag ctcactgcag ggtccaactt 480
ctgggctcaa gcggtcctcc caccttggcc cccttaagtg ctgggattgc agtcataagc 540
caccgtgcac ggcctctcta ttctactcca tttcattttt aaaaaaattg atggcctgag 600
tgctgtggct cacacatgtg aatcccagca cttcaggaag ctgatgcacg aggatcactt 660
gagcccagga gttcaaaacc agcctggaca acatagtgag accccatctc tacatacaca 720
cacacataca tgcatacata catacataca cacatacata gtaaaaaaat tagccaggca 780
tagtggctca tgcctgtaat cctagctact caagaggctg aggtgggagg attctttgag 840
ccagggaggt tgaggctgca gtgagctgtg atcatgccac tgcactccag cctgggtgag 900
gagagtgata tcctgtctca aaaagtaata ataataataa ttgatggtta cattattaca 960
aaggttagca tgagggaatt tgaggtaggg agtaatggaa ctggtgtata ccttgattgt 1020
gatggtggtc acacacatct atatatgtga cattcacgga atcatgcagt aaagaaaaat 1080
caatttcacg tctgttcatt ttaaaagtaa cgttttttaa gaagaaaaaa aatcgatagt 1140
tgcagcccac tagatagaat tcatatcact caggggttcc aacctggagt atgaaaattc 1200
ctgtccctaa aacccatgat agtggatagg gggaggcaga aagggccatt gctcgggctg 1260
tgggtgggtg agctggggag aagggagaga gtgggaggtt tcacttcctg accctcctct 1320
cttctttctg cagtcgcttc ctgcctcgga tacccatacg atgtgcctga ttacgcagga 1380
tcacggctca gctggtatga cccaggtaag gaagagccac atggagaaag gcctggggca 1440
gggggagagt ggggctgtgg tttcatcagg ccatcgggga cctctcgatg aagccatcac 1500
ttctgccaga gtgaacccca ccctatagag agagtgaacc ccagcataca cacaggcaca 1560
tagatgcaga cactgcacat taagatgctc acatgcaggt gggtgccctc gacagccgta 1620
aatcacccac aaatgccaga tctcatgata attattatga cccgctcacc atgcacagaa 1680
gacatcccag ctcataaatg taccttgcaa agtcttattt cccacccaat cctgacagat 1740
gctccatggt caaagatgtt tagagcggag tctgcagaga gaggccgcag actgatggta 1800
aagtgtgtgg aacgtccagc cttagacgtt ggagtttagt cgtagaggct gtttcccaaa 1860
tagggttcca tggagcatgt tggacaaagg gcaggcaaca ccgcatctcc cactgaagac 1920
tgacagtgta caccggccca gtaaaggatc tgagaaatcc tgcagcgaag aaatacatga 1980
cactttttaa cccagcactt tgcaccctta tttcaccaca gacctctcct tcacattgac 2040
tgggataaca tcgtgctgaa tgtacctggg gagaattgtg gctgaagggt cttgagatgc 2100

```
cactgtgcag ccagaggggg tgacaggggc cttggcaggc cctaagcacg atctgggccc   2160

tgcactgaca tcctagctcc aagctttggc acactgcttg acctcttgag cccgtttccc   2220

cagctgtgaa atgggaagaa aatctcttgc ctggtgaagc ggcaacgagc cagctcgctg   2280

ggcggacagc ctgcaaatca ccccaccaat gttaggtgtt gagacgcgct cgttctccct   2340

ctaaccagcc aagtgccctt ggcgagccct ggccctgagc tttggcccca gagtgtcctc   2400

gtcggaagaa aagggtagcc tgacccgtgg ttcccgacca gggaaaacct ccccctcaga   2460

atcacctggg agagcctttc acatttctaa aaatttcttg aatcagtgac acattcatcc   2520

agctcaaaaa tttaaaaaaa tataaaaaga tctgtagtga agagtctcac ttccatctct   2580

attcccgtct atcccagtcg cccccgacgt cgaccccaac accccaggta atgactacgt   2640

ttatttgttt cttgcatatt cttcaaggag ctctttatgc ccgtccgagg caggaagcgc   2700

tgcaacaa                                                             2708
```

<210> SEQ ID NO 3
<211> LENGTH: 3829
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
ggcgggacta gtggcgagac agctggtaca cggcacggga aactctctgg gtggccccaa     60

catgctaatc ctccggcaaa cctctgtttc ctcctcaaaa ggcaggaggt cggaaagaat    120

aaacaatgag agtcacatta aaaacacaaa atcctacgga aatactgaag aatgagtctc    180

agcactaagg aaaagcctcc agcagctcct gctttctgag ggtgaaggat agacgctgtg    240

gctctgcatg actcactagc actctatcac ggccatattc tggcagggtc agtggctcca    300

actaacattt gtttggtact ttacagttta ttaaatagat gtttatatgg agaagctctc    360

atttctttct cagaagagcc tggctaggaa ggtggatgag gcaccatatt cattttgcag    420

gtgaaattcc tgagatgtaa ggagctgctg tgacttgctc aaggccttat atcgagtaaa    480

cggtagtgct ggggcttaga cgcaggtgtt ctgatttata gttcaaaacc tctatcaatg    540

agagagcaat ctcctggtaa tgtgatagat ttcccaactt aatgccaaca taccataaac    600

ctcccattct gctaatgccc agcctaagtt ggggagacca ctccagattc caagatgtac    660

agtttgcttt gctgggcctt tttcccatgc ctgcctttac tctgccagag ttatattgct    720

ggggttttga agaagatcct attaaataaa agaataagca gtattattaa gtagccctgc    780

atttcaggtt tccttgagtg gcaggccagg cctggccgtg aacgttcact gaaatcatgg    840

cctcttggcc aagattgata gcttgtgcct gtccctgagt cccagtccat cacgagcagc    900

tggtttctaa gatgctattt cccgtataaa gcatgagacc gtgacttgcc agccccacag    960

agccccgccc ttgtccatca ctggcatctg gactccagcc tgggttgggg caaagaggga   1020

aatgagatca tgtcctaacc ctgatcctct tgtcccacag atatccagaa ccctgaccct   1080

gccggagagg gcaggggatc tctccttact tgtggcgacg tggaggagaa ccccggcccc   1140

atggccttac cagtgaccgc cttgctcctg ccgctggcct tgctgctcca cgccgccagg   1200

ccggagcaga agctgatcag cgaggaggac ctggacatcc agatgacgca aaccacctca   1260

agtctgagtg ccagtttggg tgaccgcgtt acgatcagct gtcgcgcgtc tcaggatata   1320

agcaagtacc tgaattggta ccaacagaaa cccgatggta cggtcaagtt gctgatctat   1380
```

```
cacaccagca ggctccattc aggggttccg tcccggtttt ccgggtcagg cagtggcact   1440
gactacagcc ttactatctc taacctcgaa caggaggaca tagctaccta tttttgtcaa   1500
caaggtaaca ccttgccata cactttcggg ggtggtacga aactcgagat cacagggggc   1560
ggggggtccg gtggtggtgg atcaggtgga ggtggaagcg aggtgaaact tcaagagagc   1620
ggcccggggt tggttgctcc atctcaaagc ctgtcagtga cttgcacggt ctccggagtt   1680
agcctcccgg attatggggt ttcatggata aggcagcccc cacgaaaagg tttggagtgg   1740
ctcggcgtga tttggggcag cgagacgacc tactataact ctgcgcttaa atcacgactg   1800
actataataa aagataattc taaaagtcaa gtatttctga aatgaatag cctgcaaact    1860
gatgacacgg ctatatatta ttgtgcaaaa cattactatt acggtgggtc ctatgcgatg   1920
gattattggg gccagggcac atctgtcacg gtatcatcaa ccactacacc agcaccccgg   1980
ccacctacgc cagccccaac aatcgcttca cagccattgt ctttgaggcc cgaggcttgt   2040
cgccctgcag cgggaggagc tgtgcatacg aggggtctgg actttgcctg tgacatttac   2100
atttgggcac cgctcgccgg gacgtgtgga gtgttgctgc tcagtctcgt tatcaccctt   2160
tactgctccc taaaacgggg tcgcaagaaa ctgctgtata ttttcaaaca gccattcatg   2220
cgacctgtgc aaacgacaca agaagaggac ggatgttcat gcagattccc ggaggaagaa   2280
gaaggagggt gcgagctgag agtcaaattc tctcgcagcg ccgatgcacc agcttatcaa   2340
caaggtcaga accagttgta caatgaactg aacctgggga ggcgagagga gtacgacgtt   2400
cttgacaagc gccggggacg ggaccccgaa atggggggta aaccaagacg aaagaacccc   2460
caggaggggc tctacaacga acttcagaag gacaaaatgg cggaagcata ttcagagata   2520
ggcatgaaag gtgaacgcag aagagggaaa ggacatgacg gcctctatca agggttgagc   2580
actgcaacaa aagacaccta cgatgcgctg cacatgcagg ccctgccacc acgctgaaac   2640
ttgtttattg cagcttataa tggttacaaa taaagcaata gcatcacaaa tttcacaaat   2700
aaagcatttt tttcactgca ttctagttgt ggtttgtcca aactcatcaa tgtatcttat   2760
catgtctggt gtaccagctg agagactcta aatccagtga caagtctgtc tgcctattca   2820
ccgattttga ttctcaaaca aatgtgtcac aaagtaagga ttctgatgtg tatatcacag   2880
acaaaactgt gctagacatg aggtctatgg acttcaagag caacagtgct gtggcctgga   2940
gcaacaaatc tgactttgca tgtgcaaacg ccttcaacaa cagcattatt ccagaagaga   3000
ccttcttccc cagcccaggt aagggcagct ttggtgcctt cgcaggctgt ttccttgctt   3060
caggaatggc caggttctgc ccagagctct ggtcaatgat gtctaaaact cctctgattg   3120
gtggtctcgg ccttatccat tgccaccaaa accctctttt tactaagaaa cagtgagcct   3180
tgttctggca gtccagagaa tgacacggga aaaaagcaga tgaagagaag gtggcaggag   3240
agggcacgtg gcccagcctc agtctctcca actgagttcc tgcctgcctg cctttgctca   3300
gactgtttgc cccttactgc tcttctaggc ctcattctaa gccccttctc caagttgcct   3360
ctccttattt ctccctgtct gccaaaaaat ctttcccagc tcactaagtc agtctcacgc   3420
agtcactcat taacccacca atcactgatt gtgccggcac atgaatgcac caggtgttga   3480
agtggaggaa ttaaaaagtc agatgagggg tgtgcccaga ggaagcacca ttctagttgg   3540
gggagcccat ctgtcagctg ggaaaagtcc aaataacttc agattggaat gtgttttaac   3600
tcagggttga gaaaacagct accttcagga caaaagtcag ggaagggctc tctgaagaaa   3660
tgctacttga agataccagc cctaccaagg gcagggagag gaccctatag aggcctggga   3720
```

caggagctca atgagaaagg agaagagcag caggcatgag ttgaatgaag gaggcagggc 3780
cgggtcacag gccgtgccgt gtaccagctg tctcggtgct ggaagtggt 3829

<210> SEQ ID NO 4
<211> LENGTH: 2267
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4
tggcgactcc agtccccaca tcagccggga gatgagagaa gagagtgcta ggcagtttcc 60
tggctgaaca cgccagccca atacttaaag agagcaactc ctgactccga tagagactgg 120
atggacccac aagggtgaca gcccaggcgg accgatcttc ccatcccaca tcctccggcg 180
cgatgccaaa aagaggctga cggcaactgg gccttctgca gagaaagacc tccgcttcac 240
tgccccggct ggtcccaagg gtcaggaaga tggattcata tttgctcatg tggggcctcc 300
tgacctttat tatggtccct ggctgtcaag cagagctctg tgacgatgac ccgccagaga 360
tcccacacgc cacattcaaa gccatggcct acaaggaagg aaccatgttg aactgtgaat 420
gcaagagagg tttccgcaga ataaaaagcg ggtcactcta tatgctctgt acaggaaact 480
ctagccactc gtcctgggac aaccaatgtc aatgcacaag ctctgccact cggaacacaa 540
cgaaacaagt gacacctcaa cctgaagaac agaaagaaag gaaaaccaca gaaatgcaaa 600
gtccaatgca gccagtggac caagcgagcc ttccaggtca ctgcagggaa cctccaccat 660
gggaaaatga agccacagag agaatttatc atttcgtggt ggggcagatg gtttattatc 720
agtgcgtcca gggatacagg gctctacaca gaggtcctgc tgagagcgtc tgcaaaatga 780
cccacgggaa gacaaggtgg acccagcccc agctcatatg cacaggtgaa atggagacca 840
gtcagtttcc aggtgaagag aagcctcagg caagccccga aggccgtcct gagagtgaga 900
cttcctgcct cgtcacaaca acagattttc aaatacagac agaaatggct gcaaccatgg 960
agacgtccat atttacaaca gagtaccagg tagcagtggc cggctgtgtt ttcctgctga 1020
tcagcgtcct cctcctgagt gggctcacct ggcagcggag acagaggaag agtagaagaa 1080
caatcggatc gggtgggact agtggcagca agggcgagga gctgttcacc ggggtggtgc 1140
ccatcctggt cgagctggac ggcgacgtaa acggccacaa gttcagcgtg cgcggcgagg 1200
gcgagggcga tgccaccaac ggcaagctga ccctgaagtt catctgcacc accggcaagc 1260
tgcccgtgcc ctggcccacc ctcgtgacca ccctgaccta cggcgtgcag tgcttcagcc 1320
gctaccccga ccacatgaag cgccacgact tcttcaagtc cgccatgccc gaaggctacg 1380
tccaggagcg caccatcagc ttcaaggacg acggcaccta caagacccgc gccgaggtga 1440
agttcgaggg cgacaccctg gtgaaccgca tcgagctgaa gggcatcgac ttcaaggagg 1500
acggcaacat cctggggcac aagctggagt acaacttcaa cagccacaac gtctatatca 1560
ccgccgacaa gcagaagaac ggcatcaagg ccaacttcaa gatccgccac aacgtggagg 1620
acggcagcgt gcagctcgcc gaccactacc agcagaacac ccccatcggc gacggccccg 1680
tgctgctgcc cgacaaccac tacctgagca cccagtccgt gctgagcaaa gaccccaacg 1740
agaagcgcga tcacatggtc ctgctggagt tcgtgaccgc cgccgggatc acttagaact 1800
tgtttattgc agcttataat ggttacaaat aaagcaatag catcacaaat ttcacaaata 1860
aagcattttt ttcactgcat tctagttgtg gtttgtccaa actcatcaat gtatcttatc 1920

```
atgtctggta agggcctgtg gctgcccccg gaattccggg aaggctgatg ggcatccctc   1980

ttcccagcca cagaaccaga gggagtcccc aggtagatgg ttccaagaag ggagttgaat   2040

cttgggttcc acctcttgcc tgtgacccac ggggacccca gtttatgcct cactgttcct   2100

tggtctgtca agagagcctg aaatagcatt aggttctcct gtccttctca gtccttgaca   2160

attaattctg ggaagaatag tgtggcatga tatttgggat atttggatgt taacagggtc   2220

ccgatgagca ggtttctcac cggctgatgt ggggactgta tgtggtg                 2267


<210> SEQ ID NO 5
<211> LENGTH: 169
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

aacaagcagc gcttcctgcc tcggacggac cctcctctct tctttctgca gtcgcttcct     60

gcctcggata cccatacgat gtgcctgatt acgcaggatc acggctcagc tggtatgacc    120

caggtaagga agagccacat gaacaagcag cgcttcctgc ctcggacgg                169


<210> SEQ ID NO 6
<211> LENGTH: 169
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

ccgtccgagg caggaagcgc tgcttgttac cctcctctct tctttctgca gtcgcttcct     60

gcctcggata cccatacgat gtgcctgatt acgcaggatc acggctcagc tggtatgacc    120

caggtaagga agagccacat gccgtccgag gcaggaagcg ctgcttgtt                169


<210> SEQ ID NO 7
<211> LENGTH: 169
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

aacaagcagc gcttcctgcc tcggacggac cctcctctct tctttctgca gtcgcttcct     60

gcctcggata cccatacgat gtgcctgatt acgcaggatc acggctcagc tggtatgacc    120

caggtaagga agagccacat gccgtccgag gcaggaagcg ctgcttgtt                169


<210> SEQ ID NO 8
<211> LENGTH: 167
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 8
ggtccgtccg aggcaggaag cgctgcaaca agcagcgctt cctgcctcgg acggaccctc 60
ctctcttctt tctgcagtcg cttcctgcct cggataccca tacgatgtgc ctgattacgc 120
aggatcacgg ctcagctggt atgacccagg taaggaagag ccacatg 167

<210> SEQ ID NO 9
<211> LENGTH: 167
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9
accctcctct cttctttctg cagtcgcttc ctgcctcgga tacccatacg atgtgcctga 60
ttacgcagga tcacggctca gctggtatga cccaggtaag gaagagccac atgccgtccg 120
aggcaggaag cgctgcaaca agcagcgctt cctgcctcgg acggatg 167

<210> SEQ ID NO 10
<211> LENGTH: 195
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10
ggtccgtccg aggcaggaag cgctgcaaca agcagcgctt cctgcctcgg acggaccctc 60
ctctcttctt tctgcagtcg cttcctgcct cggataccca tacgatgtgc ctgattacgc 120
aggatcacgg ctcagctggt atgacccagg taaggaagag ccacatgccg tccgaggcag 180
gaagcgctgc ttgtt 195

<210> SEQ ID NO 11
<211> LENGTH: 195
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11
aacaagcagc gcttcctgcc tcggacggac cctcctctct tctttctgca gtcgcttcct 60
gcctcggata cccatacgat gtgcctgatt acgcaggatc acggctcagc tggtatgacc 120
caggtaagga agagccacat gccgtccgag gcaggaagcg ctgcaacaag cagcgcttcc 180
tgcctcggac ggatg 195

<210> SEQ ID NO 12
<211> LENGTH: 189
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12
aacaagcagc gcttcctgcc tcggacggac cctcctctct tctttctgca gtcgcttcct 60
gcctcggata cccatacgat gtgcctgatt acgcaggatc acggctcagc tggtatgacc 120

```
caggtaagga agagccacat gccgtccgag gcaggaagcg ctgcttgttt ttgaagctac    180

catggatga                                                            189


<210> SEQ ID NO 13
<211> LENGTH: 189
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

aacaagcagc gcttcctgcc tcggacggac cctcctctct tctttctgca gtcgcttcct     60

gcctcggata cccatacgat gtgcctgatt acgcaggatc acggctcagc tggtatgacc    120

caggtaagga agagccacat gccgtccgag gcaggaagcg ctgcttgttt catccatggt    180

agcttcaaa                                                            189


<210> SEQ ID NO 14
<211> LENGTH: 181
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

tttgaagcta ccatggatga accctcctct cttctttctg cagtcgcttc ctgcctcgga     60

tacccatacg atgtgcctga ttacgcagga tcacggctca gctggtatga cccaggtaag    120

gaagagccac atgtcatcca tggtagcttc aaaccgtccg aggcaggaag cgctgcttgt    180

t                                                                    181


<210> SEQ ID NO 15
<211> LENGTH: 181
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

tttgaagcta ccatggatga accctcctct cttctttctg cagtcgcttc ctgcctcgga     60

tacccatacg atgtgcctga ttacgcagga tcacggctca gctggtatga cccaggtaag    120

gaagagccac atgtcatcca tggtagcttc aaaaacaagc agcgcttcct gcctcggacg    180

g                                                                    181


<210> SEQ ID NO 16
<211> LENGTH: 167
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

ggtccgtccg aggcaggaag cgctgcaaca agcagcgctt cctgcctcgg acggaccctc     60

ctctcttctt tctgcagtcg cttcctgcct cggataccca tacgatgtgc ctgattacgc    120

aggatcacgg ctcagctggt atgacccagg taaggaagag ccacatg                  167
```

<210> SEQ ID NO 17
<211> LENGTH: 167
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 17
ggtccgtccg aggcaggaag cgctgcaaca agcagcgctt cctgcctcgg acggcatgtg 60
gctcttcctt acctgggtca taccagctga gccgtgatcc tgcgtaatca ggcacatcgt 120
atgggtatcc gaggcaggaa gcgactgcag aaagaagaga ggagggt 167

<210> SEQ ID NO 18
<211> LENGTH: 113
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 18
accctcctct cttctttctg cagtcgcttc ctgcctcgga tacccatacg atgtgcctga 60
ttacgcagga tcacggctca gctggtatga cccaggtaag gaagagccac atg 113

<210> SEQ ID NO 19
<211> LENGTH: 71
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 19
cagaaagaag agaggagggt ccgtccgagg caggaagcgc tgcaacaagc agcgcttcct 60
gcctcggacg g 71

<210> SEQ ID NO 20
<211> LENGTH: 71
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 20
ccgtccgagg caggaagcgc tgcaacaagc agcgcttcct gcctcggacg gcatgtggct 60
cttccttacc t 71

<210> SEQ ID NO 21
<211> LENGTH: 113
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 21
accctcctct cttctttctg cagtcgcttc ctgcctcgga tacccatacg atgtgcctga 60
ttacgcagga tcacggctca gctggtatga cccaggtaag gaagagccac atg 113

<210> SEQ ID NO 22
<211> LENGTH: 77

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 22
ggtccgtccg aggcaggaag cgctgcaaca agcagcgctt cctgcctcgg acggaccggg 60
tcataccagc tgagccg 77

<210> SEQ ID NO 23
<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 23
tccgaggcag gaagcgactg ggtccgtccg aggcaggaag cgctgcttgt tgcagcgctt 60
cctgcctcgg acggacc 77

<210> SEQ ID NO 24
<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 24
tgcgtaatca ggcacatcgt ggtccgtccg aggcaggaag cgctgcttgt tgcagcgctt 60
cctgcctcgg acggacc 77

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 25

Ala Val Lys Arg Pro Ala Ala Thr Lys Lys Ala Gly Gln Ala Lys Lys
1 5 10 15

Lys Lys Leu Asp
20

<210> SEQ ID NO 26
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 26

Met Ser Arg Arg Arg Lys Ala Asn Pro Thr Lys Leu Ser Glu Asn Ala
1 5 10 15

Lys Lys Leu Ala Lys Glu Val Glu Asn
20 25

<210> SEQ ID NO 27
<211> LENGTH: 9

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Pro Ala Ala Lys Arg Val Lys Leu Asp
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Leu Lys Ile Lys Arg Pro Val Lys
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Pro Lys Lys Lys Arg Lys Val
1               5

<210> SEQ ID NO 30
<211> LENGTH: 23
<212> TYPE: DNA
<213> ORGANISM: Unknown
<220> FEATURE:
<223> OTHER INFORMATION: Description of Unknown:
      target sequence

<400> SEQUENCE: 30
gcagcgcttc ctgcctcgga cgg 23

<210> SEQ ID NO 31
<211> LENGTH: 23
<212> TYPE: DNA
<213> ORGANISM: Unknown
<220> FEATURE:
<223> OTHER INFORMATION: Description of Unknown:
      target sequence

<400> SEQUENCE: 31
ccgtccgagg caggaagcgc tgc 23

<210> SEQ ID NO 32
<211> LENGTH: 23
<212> TYPE: DNA
<213> ORGANISM: Unknown
<220> FEATURE:
<223> OTHER INFORMATION: Description of Unknown:
      target sequence

<400> SEQUENCE: 32
gagacagctg gtacacggca cgg 23

<210> SEQ ID NO 33
<211> LENGTH: 23
<212> TYPE: DNA
<213> ORGANISM: Unknown
<220> FEATURE:
<223> OTHER INFORMATION: Description of Unknown:
target sequence

<400> SEQUENCE: 33
ccgtgccgtg taccagctgt ctc 23

<210> SEQ ID NO 34
<211> LENGTH: 20
<212> TYPE: DNA
<213> ORGANISM: Unknown
<220> FEATURE:
<223> OTHER INFORMATION: Description of Unknown:
target sequence

<400> SEQUENCE: 34
actccagtcc ccacatcagc 20

<210> SEQ ID NO 35
<211> LENGTH: 20
<212> TYPE: DNA
<213> ORGANISM: Unknown
<220> FEATURE:
<223> OTHER INFORMATION: Description of Unknown:
target sequence

<400> SEQUENCE: 35
gctgatgtgg ggactgtatg 20

<210> SEQ ID NO 36
<211> LENGTH: 2708
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 36
aacaagcagc gcttcctgcc tcggacggct ccacctccca ggttcaagca attctcctgc 60
ctcagcctcc agaggagctg ggattacagg catgcatcac cacgccgagc taatttttgt 120
tatttttagt agagacaggg tttcaccata ttggctaggc cagtctcaaa ctcctgacct 180
caagtgatcc ccccacctcg gcctcccaaa gtgcttggat tataggcatg ggccaccgtg 240
cccggcccct ttctggatca tttctccatt ctctagaact aaggagctca aactttttttg 300 agtggaaaca tgcgggacat ttttacattg caaccccccaa cacacaaaaa gtgatcagtg 360
cattctgaca ttctcttttt tatttattta aaacaaaaca aacaaaaaaa aacagggtct 420
tactctgtca cccagctaga gtgctgtggc ataatcatag ctcactgcag ggtccaactt 480
ctgggctcaa gcggtcctcc caccttggcc cccttaagtg ctgggattgc agtcataagc 540
caccgtgcac ggcctctcta ttctactcca tttcattttt aaaaaaattg atggcctgag 600
tgctgtggct cacacatgtg aatcccagca cttcaggaag ctgatgcacg aggatcactt 660
gagcccagga gttcaaaacc agcctggaca acatagtgag accccatctc tacatacaca 720
cacacataca tgcatacata catacataca cacatacata gtaaaaaaat tagccaggca 780
tagtggctca tgcctgtaat cctagctact caagaggctg aggtgggagg attctttgag 840
ccagggaggt tgaggctgca gtgagctgtg atcatgccac tgcactccag cctgggtgag 900

```
gagagtgata tcctgtctca aaaagtaata ataataataa ttgatggtta cattattaca    960

aaggttagca tgagggaatt tgaggtaggg agtaatggaa ctggtgtata ccttgattgt   1020

gatggtggtc acacacatct atatatgtga cattcacgga atcatgcagt aaagaaaaat   1080

caatttcacg tctgttcatt ttaaaagtaa cgttttttaa gaagaaaaaa aatcgatagt   1140

tgcagcccac tagatagaat tcatatcact caggggttcc aacctggagt atgaaaattc   1200

ctgtccctaa aacccatgat agtggatagg gggaggcaga aagggccatt gctcgggctg   1260

tgggtgggtg agctggggag aagggagaga gtgggaggtt tcacttcctg accctcctct   1320

cttctttctg cagtcgcttc ctgcctcgga tacccatacg atgtgcctga ttacgcagga   1380

tcacggctca gctggtatga cccaggtaag gaagagccac atggagaaag gcctggggca   1440

gggggagagt ggggctgtgg tttcatcagg ccatcgggga cctctcgatg aagccatcac   1500

ttctgccaga gtgaacccca ccctatagag agagtgaacc ccagcataca cacaggcaca   1560

tagatgcaga cactgcacat taagatgctc acatgcaggt gggtgccctc gacagccgta   1620

aatcacccac aaatgccaga tctcatgata attattatga cccgctcacc atgcacagaa   1680

gacatcccag ctcataaatg taccttgcaa agtcttattt cccacccaat cctgacagat   1740

gctccatggt caaagatgtt tagagcggag tctgcagaga gaggccgcag actgatggta   1800

aagtgtgtgg aacgtccagc cttagacgtt ggagtttagt cgtagaggct gtttcccaaa   1860

tagggttcca tggagcatgt tggacaaagg gcaggcaaca ccgcatctcc cactgaagac   1920

tgacagtgta caccggccca gtaaaggatc tgagaaatcc tgcagcgaag aaatacatga   1980

cactttttaa cccagcactt tgcaccctta tttcaccaca gacctctcct tcacattgac   2040

tgggataaca tcgtgctgaa tgtacctggg gagaattgtg gctgaagggt cttgagatgc   2100

cactgtgcag ccagaggggg tgacaggggc cttggcaggc cctaagcacg atctgggccc   2160

tgcactgaca tcctagctcc aagctttggc acactgcttg acctcttgag cccgtttccc   2220

cagctgtgaa atgggaagaa aatctcttgc ctggtgaagc ggcaacgagc cagctcgctg   2280

ggcggacagc ctgcaaatca ccccaccaat gttaggtgtt gagacgcgct cgttctccct   2340

ctaaccagcc aagtgccctt ggcgagccct ggccctgagc tttggcccca gagtgtcctc   2400

gtcggaagaa aagggtagcc tgacccgtgg ttcccgacca gggaaaacct ccccctcaga   2460

atcacctggg agagcctttc acatttctaa aaatttcttg aatcagtgac acattcatcc   2520

agctcaaaaa tttaaaaaaa tataaaaaga tctgtagtga agagtctcac ttccatctct   2580

attcccgtct atcccagtcg cccccgacgt cgaccccaac accccaggta atgactacgt   2640

ttatttgttt cttgcatatt cttcaaggag ctctttatgc ccgtccgagg caggaagcgc   2700

tgcaacaa                                                            2708
```

```
<210> SEQ ID NO 37
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37

cttgaacctg ggaggtggag ccgtccgagg caggaagcgc tgcttgtt                  48


<210> SEQ ID NO 38
<211> LENGTH: 48
<212> TYPE: DNA
```

<213> ORGANISM: Artificial Sequence
<220> FEATURE:
<223> OTHER INFORMATION: Description of Artificial Sequence: Synthetic
oligonucleotide

<400> SEQUENCE: 38
ttgttgcagc gcttcctgcc tcggacgggc ataaagagct ccttgaag 48

<210> SEQ ID NO 39
<211> LENGTH: 1500
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 39
tggcgactcc agtccccaca tcagccggga gatgagagaa gagagtgcta ggcagtttcc 60
tggctgaaca cgccagccca atacttaaag agagcaactc ctgactccga tagagactgg 120
atggacccac aagggtgaca gcccaggcgg accgatcttc ccatcccaca tcctccggcg 180
cgatgccaaa aagaggctga cggcaactgg gccttctgca gagaaagacc tccgcttcac 240
tgccccggct ggtcccaagg gtcaggaaga tggattcata tttgctcatg tggggcctcc 300
tgacctttat tatggtccct ggctgtcaag caaaggaggc atgccccaca ggcctgtaca 360
cacacagcgg tgagtgctgc aaagcctgca acctgggcga gggtgtggcc cagccttgtg 420
gagccaacca gaccgtgtgt gagccctgcc tggacagcgt gacgttctcc gacgtggtga 480
gcgcgaccga gccgtgcaag ccgtgcaccg agtgcgtggg gctccagagc atgtcggcgc 540
catgcgtgga ggccgacgac gccgtgtgcc gctgcgccta cggctactac caggatgaga 600
cgactgggcg ctgcgaggcg tgccgcgtgt gcgaggcggg ctcgggcctc gtgttctcct 660
gccaggacaa gcagaacacc gtgtgcgagg agtgccccga cggcacgtat tccgacgagg 720
ccaaccacgt ggacccgtgc ctgccctgca ccgtgtgcga ggacaccgag cgccagctcc 780
gcgagtgcac acgctgggcc gacgccgagt gcgaggagat ccctggccgt tggattacac 840
ggtccacacc cccagagggc tcggacagca cagcccccag cacccaggag cctgaggcac 900
ctccagaaca agacctcata gccagcacgg tggcaggtgt ggtgaccaca gtgatgggca 960
gctcccagcc cgtggtgacc cgaggcacca ccgacaacct catccctgtc tattgctcca 1020
tcctggctgc tgtggttgtg ggtcttgtgg cctacatagc cttcaagagg tggaacagcc 1080
gcgccaagcg ctcgggttcg ggtgccacca acttcagcct gctgaagcag gccggcgacg 1140
tggaggagaa ccccggcccc gtaagggcct gtggctgccc ccggaattcc gggaaggctg 1200
atgggcatcc ctcttcccag ccacagaacc agagggagtc cccaggtaga tggttccaag 1260
aagggagttg aatcttgggt tccacctctt gcctgtgacc cacggggacc ccagtttatg 1320
cctcactgtt ccttggtctg tcaagagagc ctgaaatagc attaggttct cctgtccttc 1380
tcagtccttg acaattaatt ctgggaagaa tagtgtggca tgatatttgg gatatttgga 1440
tgttaacagg gtcccgatga gcaggtttct caccggctga tgtggggact gtatgtggtg 1500

<210> SEQ ID NO 40
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 40
gcactctctt ctctcatctc ccggctgatg tggggactgg agtcgcca 48

<210> SEQ ID NO 41
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 41
caccacatac agtccccaca tcagccggtg agaaacctgc tcatcggg 48

<210> SEQ ID NO 42
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 42
gcactctctt ctctcatctc ccggctgatg tggggactgg agtcgcca 48

<210> SEQ ID NO 43
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 43
caccacatac agtccccaca tcagccggtg agaaacctgc tcatcggg 48

<210> SEQ ID NO 44
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 44
aacaagcagc gcttcctgcc tcggacgg 28

<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 45
ttgttgcagc gcttcctgcc tcggacgg 28

<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 46
tggcgactcc agtccccaca tcagccgg 28

<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 47
caccacatac agtccccaca tcagccgg 28

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 48
aacaagtcag cgaacgacag agcgtctt 28

<210> SEQ ID NO 49
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 49
ttgttgtcag cgaacgacag agcgtctt 28

<210> SEQ ID NO 50
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 50
tggcgactcc agtccccaca tcagccgg 28

<210> SEQ ID NO 51
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 51
caccacatac agtccccaca tcagccgg 28

<210> SEQ ID NO 52
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 52
aacaagcagc gcttcctgcc tcggacgg 28

<210> SEQ ID NO 53
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 53
ttgttgcagc gcttcctgcc tcggacgg 28

<210> SEQ ID NO 54
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 54
aacaagtcag cgaacgacag agcgtctt 28

<210> SEQ ID NO 55
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 55
ttgttgtcag cgaacgacag agcgtctt 28

<210> SEQ ID NO 56
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 56
cttgaacctg ggaggtggag ccgtccgagg caggaagcga ctgttgtt 48

<210> SEQ ID NO 57
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 57
ttgttcagtc gcttcctgcc tcggacgggc ataaagagct ccttgaag 48

<210> SEQ ID NO 58
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 58
cttgaacctg ggaggtggag ccgtccgagg caggaagcga cacttgtt 48

<210> SEQ ID NO 59
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 59
ttgttgtgtc gcttcctgcc tcggacgggc ataaagagct ccttgaag 48

<210> SEQ ID NO 60
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 60
cttgaacctg ggaggtggag ccgtccgagg caggaagcgt gacttgtt 48

<210> SEQ ID NO 61
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 61
ttgttgtcac gcttcctgcc tcggacgggc ataaagagct ccttgaag 48

<210> SEQ ID NO 62
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 62
cttgaacctg ggaggtggag ccgtccgagg caggaaggct gacttgtt 48

<210> SEQ ID NO 63
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 63
ttgttgtcag ccttcctgcc tcggacgggc ataaagagct ccttgaag 48

<210> SEQ ID NO 64
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 64
cttgaacctg ggaggtggag ccgtccgagg caggatcgct gacttgtt 48

<210> SEQ ID NO 65
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 65
ttgttgtcag cgatcctgcc tcggacgggc ataaagagct ccttgaag 48

<210> SEQ ID NO 66
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 66
cttgaacctg ggaggtggag ccgtccgagg ctccttcgct gacttgtt 48

<210> SEQ ID NO 67
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 67
ttgttgtcag cgaaggagcc tcggacgggc ataaagagct ccttgaag 48

<210> SEQ ID NO 68
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 68
cttgaacctg ggaggtggag ccgtccgtcc gtccttcgct gacttgtt 48

<210> SEQ ID NO 69
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 69
ttgttgtcag cgaaggacgg acggacgggc ataaagagct ccttgaag 48

<210> SEQ ID NO 70
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 70
cttgaacctg ggaggtggag ccgaggctcc gtccttcgct gacttgtt 48

<210> SEQ ID NO 71
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 71
ttgttgtcag cgaaggacgg agcctcgggc ataaagagct ccttgaag 48

<210> SEQ ID NO 72
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 72
gcactctctt ctctcatctc ccggctgatg tggggactgc tcacgcca 48

<210> SEQ ID NO 73
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 73
caccatgagc agtccccaca tcagccggtg agaaacctgc tcatcggg 48

<210> SEQ ID NO 74
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 74
gcactctctt ctctcatctc ccggctgatg tggggactgc tgtcgcca 48

<210> SEQ ID NO 75
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 75
caccaacagc agtccccaca tcagccggtg agaaacctgc tcatcggg 48

<210> SEQ ID NO 76
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 76
gcactctctt ctctcatctc ccggctgatg tggggactgg agtcgcca 48

<210> SEQ ID NO 77
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 77
caccaactcc agtccccaca tcagccggtg agaaacctgc tcatcggg 48

<210> SEQ ID NO 78
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 78
gcactctctt ctctcatctc ccggctgatg tggggacacg agtcgcca 48

<210> SEQ ID NO 79
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 79
caccaactcg tgtccccaca tcagccggtg agaaacctgc tcatcggg 48

<210> SEQ ID NO 80
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 80
gcactctctt ctctcatctc ccggctgatg tggggtgacg agtcgcca 48

<210> SEQ ID NO 81
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 81
caccaactcg tcaccccaca tcagccggtg agaaacctgc tcatcggg 48

<210> SEQ ID NO 82
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 82
gcactctctt ctctcatctc ccggctgatg tcccctgacg agtcgcca 48

<210> SEQ ID NO 83
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 83
caccaactcg tcaggggaca tcagccggtg agaaacctgc tcatcggg 48

<210> SEQ ID NO 84
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 84
gcactctctt ctctcatctc ccggctgtac acccctgacg agtcgcca 48

<210> SEQ ID NO 85
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 85
caccaactcg tcaggggtgt acagccggtg agaaacctgc tcatcggg 48

<210> SEQ ID NO 86
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 86
gcactctctt ctctcatctc ccgcgactac acccctgacg agtcgcca 48

<210> SEQ ID NO 87
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 87
caccaactcg tcaggggtgt agtcgcggtg agaaacctgc tcatcggg 48

<210> SEQ ID NO 88
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 88
cttgaacctg ggaggtggag ccgtccgagg caggaagcgc tgcttgtt 48

<210> SEQ ID NO 89
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 89
ccgtccgagg caggaagcgc tgcttgtt 28

<210> SEQ ID NO 90
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 90
tccgaggcag gaagcgctgc ttgtt 25

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 91
tccgaggcag gaagcgctgc 20

<210> SEQ ID NO 92
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 92
cttgaacctg ggaggtggag ccgtccgagg caggaagcgc tgc 43

<210> SEQ ID NO 93
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 93
cttgaacctg ggaggtggag ccg 23

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 94
ccgtccgagg caggaagcgc tgc 23

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 95
cttgaacctg ggaggtggag 20

<210> SEQ ID NO 96
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 96
ttgttgcagc gcttcctgcc tcggacgggc ataaagagct ccttgaag 48

<210> SEQ ID NO 97
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 97
ttgttgcagc gcttcctgcc tcggacgg 28

<210> SEQ ID NO 98
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 98
ttgttgcagc gcttcctgcc tcgga 25

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 99
gcagcgcttc ctgcctcgga 20

<210> SEQ ID NO 100
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 100
gcagcgcttc ctgcctcgga cgggcataaa gagctccttg aag 43

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 101
cgggcataaa gagctccttg aag 23

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 102
gcagcgcttc ctgcctcgga cgg 23

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 103
gcataaagag ctccttgaag 20

<210> SEQ ID NO 104
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 104
gcactctctt ctctcatctc ccggctgatg tggggactgg agtcgcca 48

<210> SEQ ID NO 105
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 105
ccggctgatg tggggactgg agtcgcca 28

<210> SEQ ID NO 106
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 106
gctgatgtgg ggactggagt cgcca 25

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 107
gctgatgtgg ggactggagt 20

<210> SEQ ID NO 108
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 108
gcactctctt ctctcatctc ccggctgatg tggggactgg agt 43

<210> SEQ ID NO 109
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 109
gcactctctt ctctcatctc ccg 23

<210> SEQ ID NO 110
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 110
ccggctgatg tggggactgg agt 23

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 111
gagatgagag aagagagtgc 20

<210> SEQ ID NO 112
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 112
caccacatac agtccccaca tcagccggtg agaaacctgc tcatcggg 48

<210> SEQ ID NO 113
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 113
caccacatac agtccccaca tcagccgg 28

<210> SEQ ID NO 114
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 114
caccacatac agtccccaca tcagc 25

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 115
catacagtcc ccacatcagc 20

<210> SEQ ID NO 116
<211> LENGTH: 43
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 116
catacagtcc ccacatcagc cggtgagaaa cctgctcatc ggg 43

<210> SEQ ID NO 117
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 117
cggtgagaaa cctgctcatc ggg 23

<210> SEQ ID NO 118
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 118
catacagtcc ccacatcagc cgg 23

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 119
tgagaaacct gctcatcggg 20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 120
ctggatatct gtgggacaag 20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 121
tcagggttct ggatatctgt 20

<210> SEQ ID NO 122
<211> LENGTH: 2267
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 122
tggcgactcc agtccccaca tcagccggga gatgagagaa gagagtgcta ggcagtttcc 60
tggctgaaca cgccagccca atacttaaag agagcaactc ctgactccga tagagactgg 120
atggacccac aagggtgaca gcccaggcgg accgatcttc ccatcccaca tcctccggcg 180
cgatgccaaa aagaggctga cggcaactgg gccttctgca gagaaagacc tccgcttcac 240
tgccccggct ggtcccaagg gtcaggaaga tggattcata tttgctcatg tggggcctcc 300
tgacctttat tatggtccct ggctgtcaag cagagctctg tgacgatgac ccgccagaga 360
tcccacacgc cacattcaaa gccatggcct acaaggaagg aaccatgttg aactgtgaat 420
gcaagagagg tttccgcaga ataaaaagcg ggtcactcta tatgctctgt acaggaaact 480
ctagccactc gtcctgggac aaccaatgtc aatgcacaag ctctgccact cggaacacaa 540
cgaaacaagt gacacctcaa cctgaagaac agaaagaaag gaaaaccaca gaaatgcaaa 600
gtccaatgca gccagtggac caagcgagcc ttccaggtca ctgcagggaa cctccaccat 660
gggaaaatga agccacagag agaatttatc atttcgtggt ggggcagatg gtttattatc 720

-continued

```
agtgcgtcca gggatacagg gctctacaca gaggtcctgc tgagagcgtc tgcaaaatga    780
cccacgggaa gacaaggtgg acccagcccc agctcatatg cacaggtgaa atggagacca    840
gtcagtttcc aggtgaagag aagcctcagg caagccccga aggccgtcct gagagtgaga    900
cttcctgcct cgtcacaaca acagattttc aaatacagac agaaatggct gcaaccatgg    960
agacgtccat atttacaaca gagtaccagg tagcagtggc cggctgtgtt ttcctgctga   1020
tcagcgtcct cctcctgagt gggctcacct ggcagcggag acagaggaag agtagaagaa   1080
caatcggatc gggtgggact agtggcagca agggcgagga gctgttcacc ggggtggtgc   1140
ccatcctggt cgagctggac ggcgacgtaa acggccacaa gttcagcgtg cgcggcgagg   1200
gcgagggcga tgccaccaac ggcaagctga ccctgaagtt catctgcacc accggcaagc   1260
tgcccgtgcc ctggcccacc ctcgtgacca ccctgaccta cggcgtgcag tgcttcagcc   1320
gctaccccga ccacatgaag cgccacgact tcttcaagtc cgccatgccc gaaggctacg   1380
tccaggagcg caccatcagc ttcaaggacg acggcaccta caagacccgc gccgaggtga   1440
agttcgaggg cgacaccctg gtgaaccgca tcgagctgaa gggcatcgac ttcaaggagg   1500
acggcaacat cctggggcac aagctggagt acaacttcaa cagccacaac gtctatatca   1560
ccgccgacaa gcagaagaac ggcatcaagg ccaacttcaa gatccgccac aacgtggagg   1620
acggcagcgt gcagctcgcc gaccactacc agcagaacac ccccatcggc gacggccccg   1680
tgctgctgcc cgacaaccac tacctgagca cccagtccgt gctgagcaaa gaccccaacg   1740
agaagcgcga tcacatggtc ctgctggagt tcgtgaccgc cgccgggatc acttagaact   1800
tgtttattgc agcttataat ggttacaaat aaagcaatag catcacaaat ttcacaaata   1860
aagcattttt ttcactgcat tctagttgtg gtttgtccaa actcatcaat gtatcttatc   1920
atgtctggta agggcctgtg gctgcccccg gaattccggg aaggctgatg ggcatccctc   1980
ttcccagcca cagaaccaga gggagtcccc aggtagatgg ttccaagaag ggagttgaat   2040
cttgggttcc acctcttgcc tgtgacccac ggggacccca gtttatgcct cactgttcct   2100
tggtctgtca agagagcctg aaatagcatt aggttctcct gtccttctca gtccttgaca   2160
attaattctg ggaagaatag tgtggcatga tatttgggat atttggatgt taacagggtc   2220
ccgatgagca ggtttctcac cggctgatgt ggggactgta tgtggtg                 2267
```